(12) United States Patent
Cui et al.

(10) Patent No.: US 9,987,370 B2
(45) Date of Patent: *Jun. 5, 2018

(54) SELF-ASSEMBLING DRUG AMPHIPHILES AND METHODS FOR SYNTHESIS AND USE

(71) Applicant: THE JOHNS HOPKINS UNIVERSITY, Baltimore, MD (US)

(72) Inventors: Honggang Cui, Lutherville, MD (US); Andrew G. Cheetham, Charlottesville, VA (US); Pengcheng Zhang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/934,660

(22) Filed: Nov. 6, 2015

(65) Prior Publication Data

US 2016/0220691 A1    Aug. 4, 2016

Related U.S. Application Data

(62) Division of application No. 14/044,329, filed on Oct. 2, 2013, now Pat. No. 9,180,203.

(60) Provisional application No. 61/717,447, filed on Oct. 23, 2012.

(51) Int. Cl.

| | |
|---|---|
| *A61K 47/48* | (2006.01) |
| *A61K 31/4745* | (2006.01) |
| *A61K 31/337* | (2006.01) |
| *A61K 38/04* | (2006.01) |
| *A61K 33/24* | (2006.01) |
| *A61K 47/55* | (2017.01) |
| *A61K 47/64* | (2017.01) |
| *A61K 47/69* | (2017.01) |

(52) U.S. Cl.
CPC ........ *A61K 47/48246* (2013.01); *A61K 33/24* (2013.01); *A61K 47/551* (2017.08); *A61K 47/64* (2017.08); *A61K 47/6929* (2017.08)

(58) Field of Classification Search
CPC .............. A61K 47/48246; A61K 33/24; A61K 47/551; A61K 47/64; A61K 47/6929
See application file for complete search history.

(56) References Cited

FOREIGN PATENT DOCUMENTS

| WO | WO 0042071 A2 * | 7/2000 | ......... A61K 31/4375 |
|---|---|---|---|
| WO | WO 2006/062779 A2 * | 6/2006 | ....... A61K 47/48384 |
| WO | WO 2007/113687 A2 * | 10/2007 | ......... A61K 31/4745 |

OTHER PUBLICATIONS

Tat-HIV1, from https://www.ncbi.nlm.nih.gov/protein/P35965, pp. 1-5, accessed Oct. 31, 2016.*
Water, from http://www.biology-online.org/dictionary/Water, pp. 1-3, accessed Apr. 24, 2014.*
Human insulin, from https://www.ncbi.nlm.nih.gov/protein/AAA59172.1, pp. 1-2, accessed Oct. 31, 2016.*
Cui et al, Self-Assembly of Peptide Amphiphiles: From Molecules to Nanostructures to Biomaterials, Biopolymers (Pept Sci), 2010, 94, pp. 1-18.*
Harada et al, Antitumor Activity of Palmitic Acid Found as a Selective Cytotoxic Substance in a Marine Red Alga, Anticancer Research, 2002, 22, pp. 2587-2590.*
Snyder et al, Enhanced Targeting and Killing of Tumor Cells Expressing the CXC Chemokine Receptor 4 by Transducible Anticancer Peptides, Cancer Res, 2005, 65, pp. 10646-10650.*
Ladino et al, Folate-Maytansinoids: Target-Selective Drugs of Low Molecular Weight, Int. J. Cancer, 1997, 73, pp. 859-864.*
Mangavel et al, Basic amphipathic model peptides: Structural investigations in solution, studied by circular dichroism, fluorescence, analytical ultracentrifugation and molecular modelling, J. Chim. Phys., 1999, 96, pp. 877-903.*
Tryptophan, from https://www.drugs.com/tryptophan.html, pp. 1-9, accessed May 18, 2017.*
von Bergen et al, Tau aggregation is driven by a transition from random coil to beta sheet structure, Biochimica et Biophysica Acta, 2005, 1739, pp. 158-166.*

* cited by examiner

*Primary Examiner* — Julie Ha
*Assistant Examiner* — Li N Komatsu
(74) *Attorney, Agent, or Firm* — John Hopkins Technology Transfer

(57) ABSTRACT

The present invention provides herein the design of monodisperse, amphiphilic anticancer drugs—which are now termed "drug amphiphiles" (DAs)—that can spontaneously associate into discrete, stable supramolecular nanostructures with the potential for self-delivery (no additional carriers are needed). The quantitative drug loading in the resulting nanostructures is ensured by the very nature of the molecular design. The DA is a composition comprising: D-L-PEP; wherein D is 1 to 4 hydrophobic drug molecules which can be the same or different; L is 1 to 4 biodegradable linkers which can be the same or different; and PEP is a peptide that can spontaneously associate into discrete, stable supramolecular nanostructures. In an alternate embodiment, the DA composition also comprises a targeting ligand (T). Methods of making DA molecules, as well as their use in treatment of disease are also provided.

6 Claims, 35 Drawing Sheets

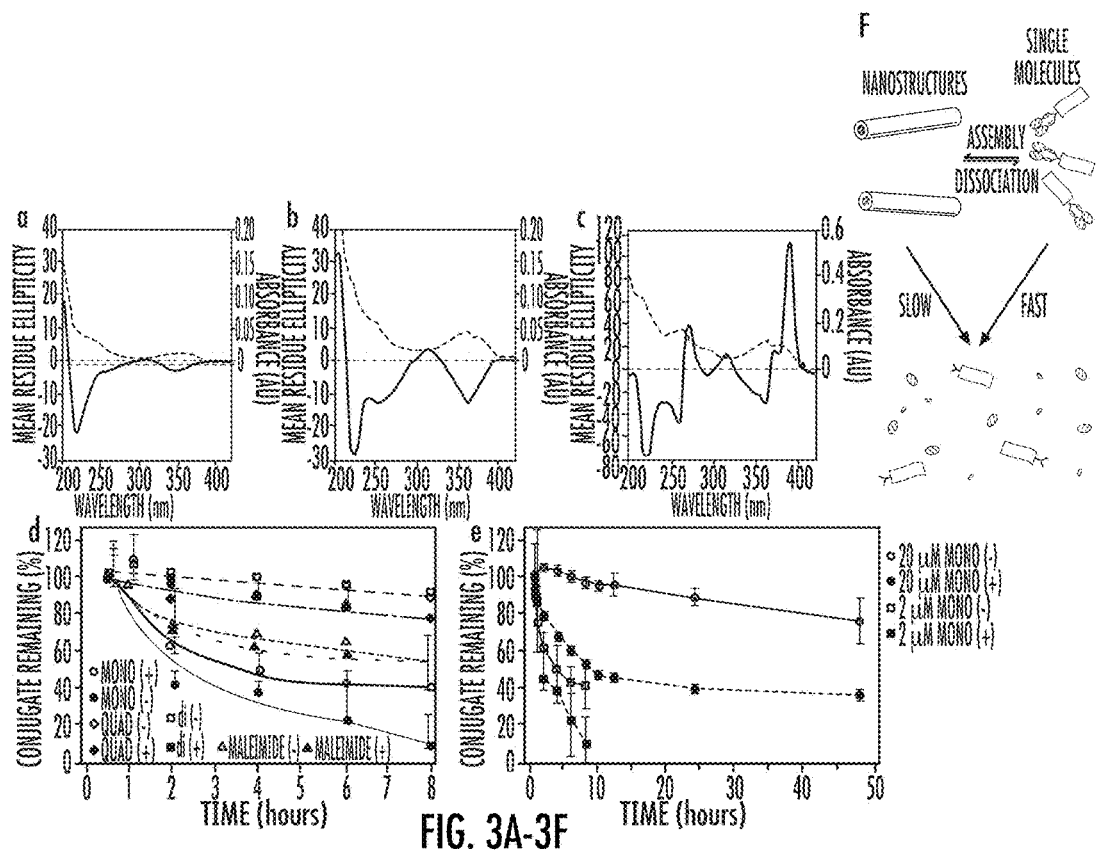
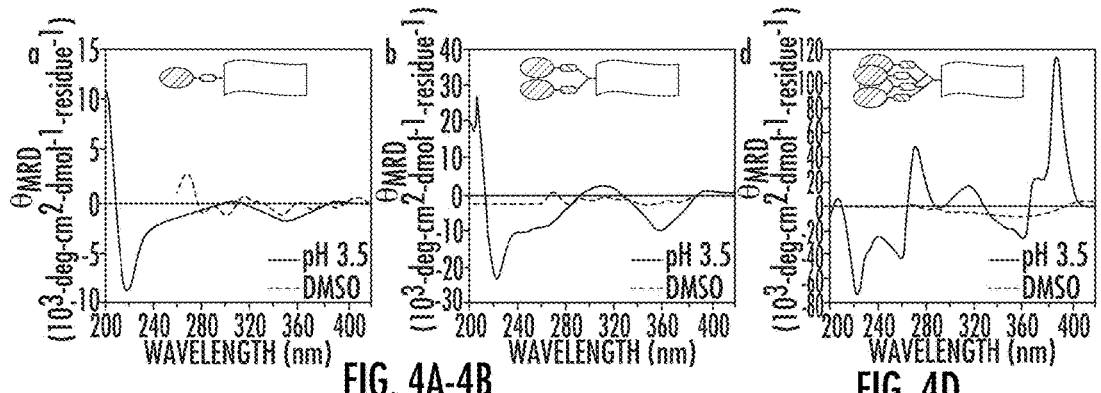
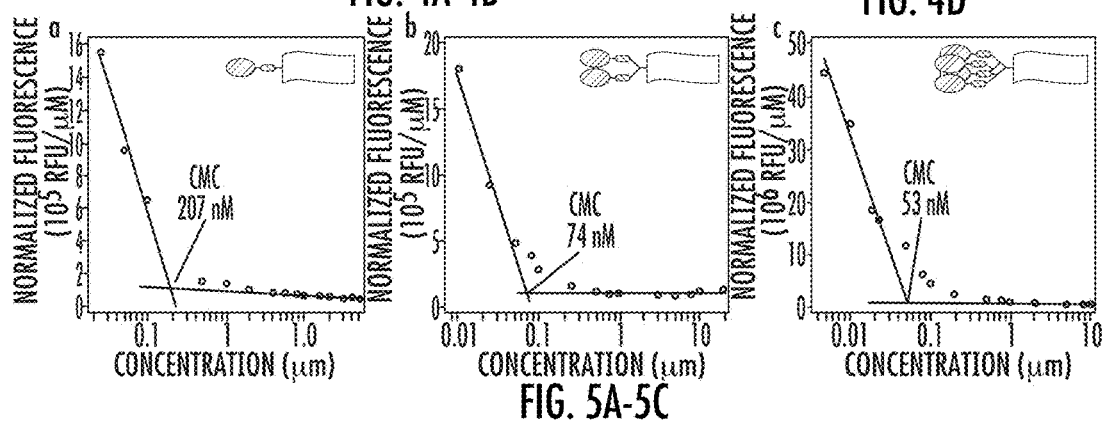
FIG. 3A-3F
FIG. 4A-4B    FIG. 4D
FIG. 5A-5C

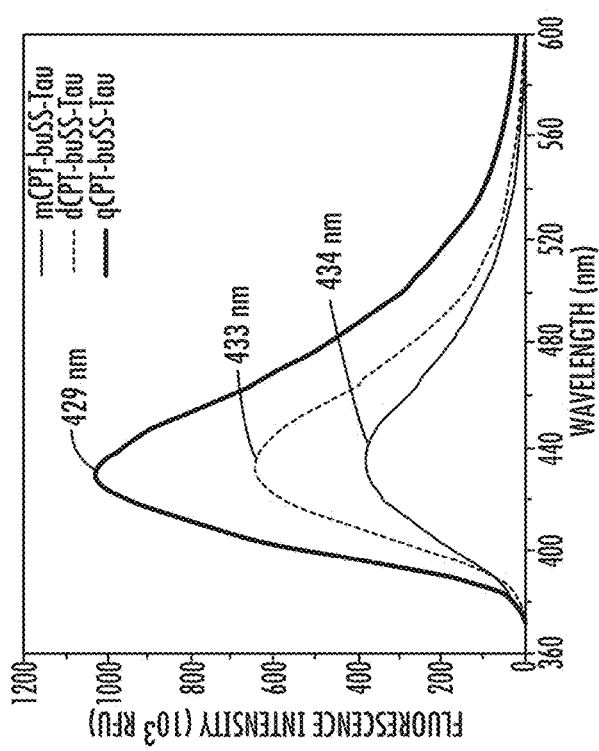
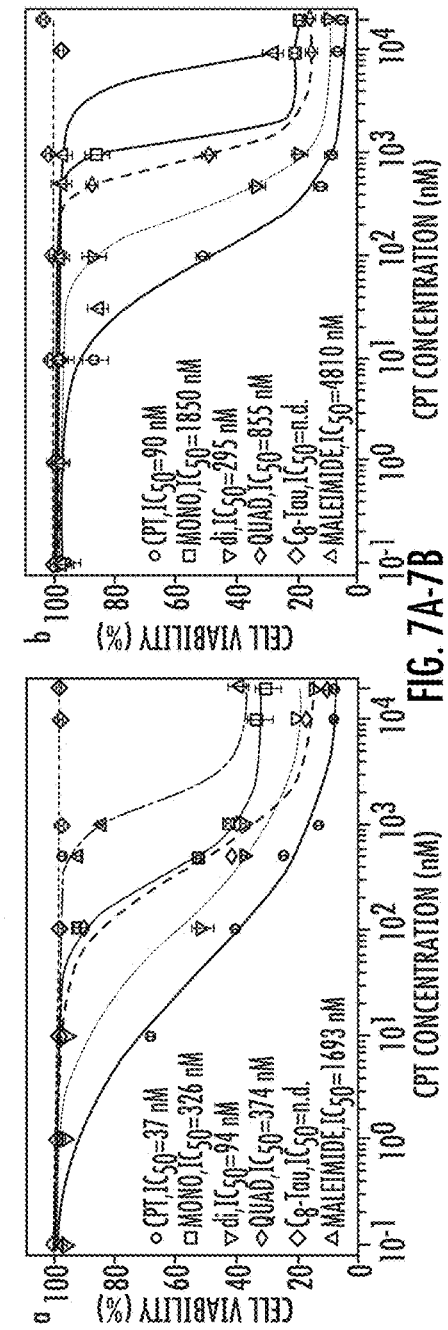
FIG. 6
FIG. 7A-7B (A)

(B)

SELF-ASSEMBLING DRUG AMPHIPHILES AND METHODS FOR SYNTHESIS AND USE

REFERENCE TO RELATED APPLICATIONS

This application is a divisional application of U.S. patent application Ser. No. 14/044,329, filed Oct. 2, 2013, which issued as U.S. Pat. No. 9,180,203, and which claims the benefit of U.S. Provisional Patent Application No. 61/717,447, filed on Oct. 23, 2012, the content of each of the aforementioned applications is herein incorporated by reference in their entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on May 10, 2017, is named P12082-05_ST25.txt, and is 3,117 bytes in size.

BACKGROUND OF THE INVENTION

The creation of vehicles for the effective delivery of hydrophobic anticancer drugs to tumor sites has garnered major attention in cancer chemotherapies for several decades. A successful strategy promises immense benefits to cancer sufferers through both the reduction of side-effects and a greater treatment efficacy. Current approaches focus on the use of nanocarriers, whereby the drug's pharmacokinetic properties and biodistribution profiles are manipulated by encapsulation within liposomes, polymeric nanoparticles or micelles, or by conjugation to hydrophilic polymers or inorganic nanomaterials. While these methods can be effective, there are concerns regarding the short-term and long-term toxicities arising from the synthetic nanomaterials other than the drug being delivered. This often leads to exhaustive preclinical evaluation and thus represents a difficult hurdle for the drug's translation into clinical use. Furthermore, there are inherent difficulties in achieving a quantitative and high drug loading per carrier, and the drug loading capacity varies depending not only on the carrier's properties but also on the type of drugs to be encapsulated or conjugated. Polydispersity, both in terms of polymer length and the amount of drug loaded or conjugated, is a critical issue susceptible to significant batch-to-batch variability. On the other hand, small molecule prodrugs are monodisperse but can be subject to rapid clearance and premature degradation Many drugs, including chemotherapeutic drugs for cancer are well known for having low water solubility, for example, camptothecin and paclitaxel. To circumvent this, two strategies have been adopted—chemical modification of the drug to increase solubility or the use of a delivery vehicle. Camptothecin, a DNA-Topoisomerase I inhibitor that prevents DNA re-ligation during transcription and ultimately causes cell apoptosis, is not currently used in clinical cancer chemotherapy due to its very low water solubility and toxic side effects; however, its more soluble derivatives have successfully made the transition into clinical use, such as Topetecan (HYCAMTIN, GlaxoSmithKline) and Irinotecan (CAMPTOSAR, Pfizer and CAMPTO, Yakult Honsha). These derivatives still cause significant side-effects due to non-selective modes of action, and would benefit from an improved delivery strategy. Paclitaxel, a mitotic inhibitor that stabilizes microtubules, preventing cell division and inducing apoptosis, has for many years been administered intravenously as a solution in Chremophor EL (CrEL), a formulation known as (TAXOL, Bristol-Myers Squibb). The Chremophor EL solvent, however, causes side-effects of its own in addition to those due to paclitaxel and alternatives are highly desired. In 2005, an injectable formulation of paclitaxel in which the drug is bound to the protein albumin was approved for use by the FDA. Known as (ABRAXANE, Celgene), this mode of delivery represents the first nanoparticle albumin bound (nab) technology platform. While the carrier causes little to no side-effects, those due to the paclitaxel are still present.

As such, there still exists a need for improved compositions and methods for solubilizing drug compounds that have low water solubility without inducing unwanted secondary biological effects due to the solubilization methods.

SUMMARY OF THE INVENTION

The present invention provides herein the design of monodisperse, amphiphilic anticancer prodrugs—which are now termed "drug amphiphiles" (DAs)—that can spontaneously associate into discrete, stable supramolecular nanostructures with the potential for self-delivery (no additional carriers are needed). The very nature of the molecular design ensures that a fixed and tunable drug loading can be achieved. Assembly of these DAs provides a basis for increasing the drug solubility and stability to non-specific degradation, and for improving specific targeting to tumor cells, with concomitant reduction in systemic toxicity towards healthy tissues and improved treatment efficacy.

In order to imbue these properties upon an anticancer drug, a hydrophilic peptide is conjugated to the drug via a biodegradable linker. The hydrophilic peptide increases the aqueous solubility of the drug and can promote the formation of well-defined nanostructure architectures including, but not limited to, cylindrical or spherical micelles, hollow nanotubes, toroids, discs and vesicles, through preferred secondary structure formation, e.g. beta sheet, alpha helix, poly proline type-II helix, beta turn. The peptide may also include moieties that will allow the assembled nanostructure to preferentially accumulate at tumor sites using established targeting strategies such as folate ligands or integrin-binding peptides (RGDS (SEQ ID NO: 13), for example), and/or that can improve overall pharmacokinetics, e.g. pegylation. The biodegradable linker can be sensitive to cleavage by a number of tumor-relevant stimuli including, but not limited to, reducing agents (glutathione, cysteine, etc.), proteolytic enzymes (Cathepsins, Matrix Metalloproteases, etc.) and low pH (endosomal/lysosomal pH). The drug-linker can be conjugated to the hydrophilic peptide via established protein conjugation methodologies including, but not limited to, disulfide formation via reaction of cysteine-thiol with an activated thiol, thioether formation via reaction of cysteine-thiol with a maleimide, triazole formation via copper-assisted azide-alkyne cycloaddition (CuAAC) and other "Click" reactions.

In one embodiment of the invention the Tau-protein derived sequence GVQIVYKK (SEQ ID NO: 1) was conjugated to two known chemotherapeutic agents, camptothecin (CPT) and paclitaxel (PXL), which are models for low water soluble chemotherapeutic agents, and which resulted in several benefits in antitumor treatment therapeutics. First, the DA was composed of hydrophobic CPT or PXL and hydrophilic Tau peptide, which enables the conjugate DA to form nanostructures for the delivery process. Furthermore, the preference of the Tau peptide for beta sheet formation promotes the formation of nanofiber-like structures. Second, by conjugating the drugs to a peptide sequence instead of encapsulating the drug into polymers, a highly improved drug loading was observed. Third, a biodegradable disulfide bond linker (e.g., disulfanylbutanoate (buSS)) was utilized, which can be degraded by glutathione and other reducing agents within tumor cells to allow controlled release during the drug delivery process. Fourth, the formation of nanostructures effectively shields the drug and linker moieties from the external environment, only displaying significant release of the active drug when in the monomeric form or when exposed to glutathione or other reducing agents. This property allows for increased extracellular stability, with cleavage occurring upon cellular internalization.

In accordance with an embodiment, the present invention provides a DA composition comprising: D-L-PEP; wherein D is 1 to 4 hydrophobic drug molecules; L is 1 to 4 biodegradable linkers; and PEP is a hydrophilic peptide that can promote the formation of specific nanostructure architectures.

In accordance with another embodiment, the present invention provides a composition comprising 1 to 4 hydrophobic chemotherapeutic molecules linked via 1 to 4 (disulfanylbutanoate) (buSS) linking molecules to cysteine-modified analogues of the Tau-protein derived peptide GVQIVYKK (SEQ ID NO: 1).

In accordance with a further embodiment, the present invention provides a method for making the compositions described above comprising reaction of the 4-(pyridin-2-yldisulfanyl)butanoate-functionalized CPT or PXL with a cysteine-functionalized hydrophilic peptide to furnish the described DA conjugates.

In accordance with an embodiment, the present invention provides a DA composition comprising: D-L-PEP-T; wherein D is 1 to 4 hydrophobic drug molecules; L is 1 to 4 biodegradable linkers; and PEP is a hydrophilic peptide that can promote the formation of specific nanostructure architectures, and T is a targeting ligand.

In accordance with yet another embodiment, the present invention provides a method of treating a disease in a mammal comprising administering to the mammal a therapeutically effective amount of the compositions described above, sufficient to slow, stop or reverse the disease in the mammal.

BRIEF DESCRIPTION OF THE DRAWINGS

FIGS. 3A-3F shows the spectroscopic analysis and release study of the drug amphiphiles. Circular dichroism (CD, solid line) and UV-Vis (dashed line) spectroscopic analysis of 1 μM mCPT-buSS-Tau (a), 1 μM dCPT-buSS-Tau (b) and 1 μM qCPT-buSS-Tau (c) in 10 mM sodium phosphate. Mean residue ellipticity values are given in $10^3 \cdot deg \cdot cm^2 \cdot dmol^{-1} \cdot residue^{-1}$. Release study of 2 μM DA and control molecules in the presence and absence of 10 mM glutathione (GSH) in 10 mM sodium phosphate at 37° C. (d). Comparison of mCPT-buSS-Tau release kinetics at 2 μM and 20 μM (e). Release experiments were performed in triplicate and values are given as mean±s.d. (Key: mono=mCPT-buSS-Tau, di=dCPT-buSS-Tau, quad=qCPT-buSS-Tau, maleimide=mCPT-mal-Tau). Schematic illustration of the proposed release mechanism showing the effect of self-assembly on the susceptibility of the DAs to degradation (f).

FIGS. 4A, 4B, 4D shows the CD spectra for mCPT-buSS-Tau (a), dCPT-buSS-Tau (b) and qCPT-buSS-Tau (d) at pH 3.5 (1 mM HCl) and in DMSO, showing persistence of the nanostructures under more acidic conditions and their existence as single molecules in DMSO. Both mCPT-buSS-Tau and dCPT-buSS-Tau show little to no signal in DMSO, whereas qCPT-buSS-Tau shows a relatively stronger signal. All solutions were 1 μM, with the exception of qCPT-buSS-Tau which was 500 nM in DMSO.

FIGS. 5A-5C depicts the fluorometric determination of the CMC values for mCPT-buSS-Tau (a), dCPT-buSS-Tau (b) and qCPT-buSS-Tau (c) in 10 mM sodium phosphate.

FIG. 6 shows the fluorescence spectra of 1 μM solutions of mCPT-buSS-Tau, dCPT-buSS-Tau and qCPT-buSS-Tau in 10 mM sodium phosphate ($\lambda_{em}$=350 nm).

FIGS. 7A-7B shows an in vitro dose-response relationship study of the DA molecules against human MCF-7 breast cancer (a) and rat 9L gliosarcoma (b) cells. All cancer cells were incubated with the appropriate DA molecules for 48 hours and cell viability was determined by SRB assay. Cytotoxicity experiments were performed in triplicate and values are given as mean±s.d. (n=3). Key: see FIG. 3

FIGS. 30 a) and b): 200 μM in water. FIGS. 30 c) and d): 10 μM in water.

FIG. 31 a) maximum wavelength showing that the CMC value lies between 10 μM and 50 μM. FIG. 31 b) CD spectrum of conjugate solution at 5 μM in water. FIG. 31 c) CD spectrum of conjugate solution at 100 μM in water.

DETAILED DESCRIPTION OF THE INVENTION

Figures 1A, 1B, 1C, 1D:
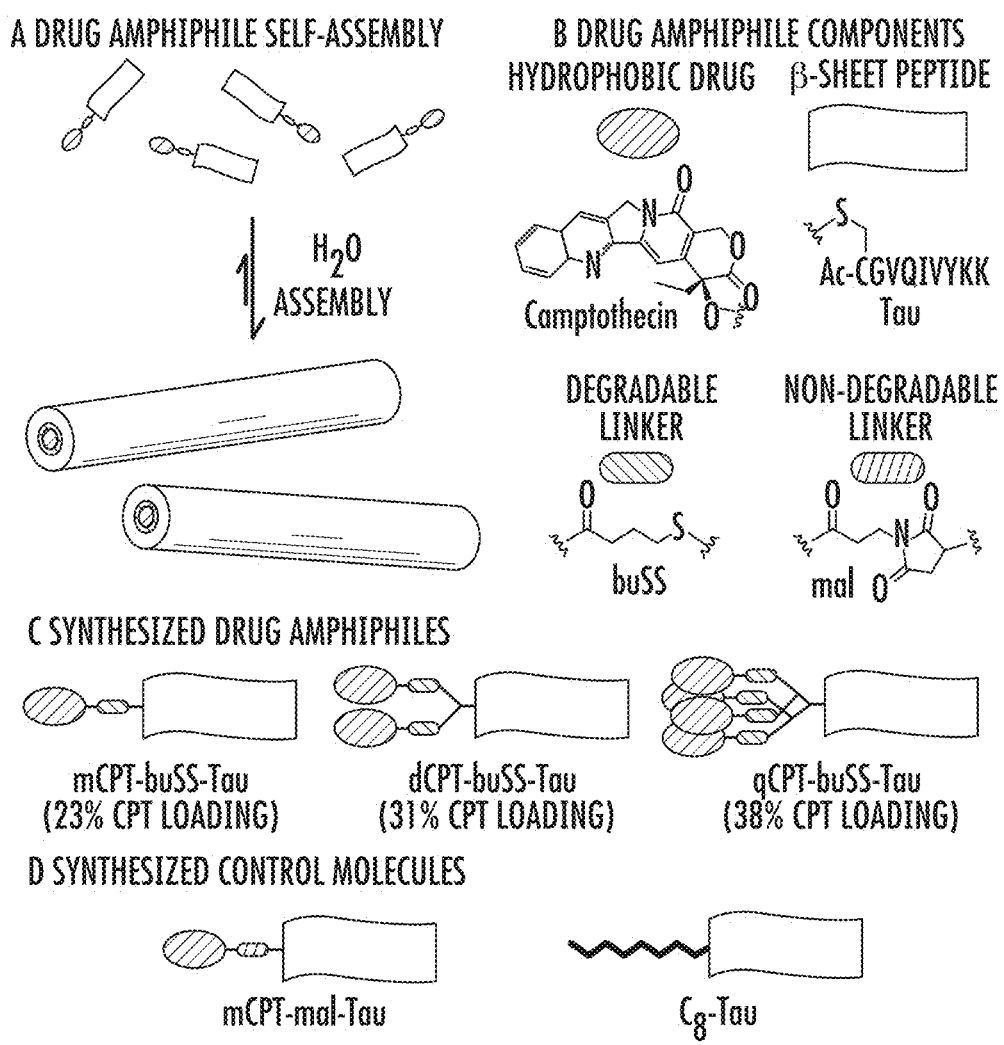
FIGS. 1A-1D illustrates an embodiment of the invention, including the structures of the drug amphiphiles (DAs) and control molecules. a). The self-assembled nanostructures contain the same drug fraction as the individual DA. b). The three key component parts of a drug amphiphile studied in this paper: the hydrophobic drug CPT, the Tau β-sheet forming peptide, and the buSS biodegradable linker. c). The synthesized CPT DAs with quantitative drug loadings of 23%, 31% and 38%. d. The two synthesized control molecules.

In accordance with an embodiment, the present invention provides a DA composition comprising: D-L-PEP; wherein D is 1 to 4 hydrophobic drug molecules; L is 1 to 4 biodegradable linkers; and PEP is a hydrophilic peptide that can promote the formation of specific nanostructure architectures.

As used herein, the term "hydrophobic drug molecules" roughly describes a heterogeneous group of molecules that exhibit poor solubility in water but that are typically, but certainly not always, soluble in various organic solvents. Often, the terms slightly soluble (1-10 mg/ml), very slightly soluble (0.1-1 mg/ml), and practically insoluble (<0.1 mg/ml) are used to categorize such substances. Drugs such as steroids and many anticancer drugs are important classes of poorly water-soluble drugs; however, their water solubility varies over at least two orders of magnitudes. Typically, such molecules require secondary solubilizers such as carrier molecules, liposomes, polymers, or macrocyclic molecules such as cyclodextrins to help the hydrophobic drug molecules dissolve in aqueous solutions necessary for drug delivery in vivo. Other types of hydrophobic drugs show even a lower aqueous solubility of only a few ng/ml. Since insufficient solubility commonly accompanies undesired pharmacokinetic properties, the high-throughput screening of kinetic and thermodynamic solubility as well as the prediction of solubility is of major importance in discovery (lead identification and optimization) and development.

As used herein, the term "biodegradable linkers" refers to a small molecule or peptide fragment that is capable of covalently linking the hydrophobic drug molecule to the hydrophilic peptide in the present invention. These covalent linkages must be sufficiently labile to be hydrolyzed or cleaved when in the target cell or organ of a subject. In certain embodiments, the linker bonds are preferably cleaved off in the target organ or cell by an enzyme or cellular component that is at a higher concentration in the target microenvironment than in the body or outside of the target cell or organ. Examples of such linker moieties include, but are not limited to amides, disulfides, polyamino acids, biopolymers, esters, aldehydes, hydrazones and the like.

In accordance with an embodiment, the biodegradable linkers of the present invention include (4-(pyridin-2-yldisulfanyl)butanoate) (buSS). The buSS linker has a disulfide moiety that allows it to be reductively cleaved primarily intracellularly by glutathione. In particular, the concentration of glutathione inside tumor cells is 100 to 1000 times higher than in the interstitial fluid, thus allowing the compositions of the present invention to act as a prodrug and enter the cell intact. Once inside the cell, the reduction of the linker bonds by glutathione occurs, and the free hydrophobic drug molecule can act on its target. It will be understood by those of ordinary skill in the art that other linker moieties can be used where they interact with the hydrophilic peptide in a similar manner.

As used herein, the term "tau peptide fragment" means a peptide fragment of the paired helical filament Tau protein. In an embodiment, the peptide fragment comprises the amino acid sequence GVQIVYKK (SEQ ID NO: 1). The tau peptide fragment is hydrophilic and a strong promoter of beta sheet formation, enabling the conjugate to adopt fibrous nanostructures in aqueous solutions. This provides a number of significant features to the composition, including (1) highly improved drug loading due to the fact that from 1 to 4 drug molecules can be bound to each tau peptide fragment; (2) increased solubility of the hydrophobic drugs due to the presence of the hydrophilic peptide; (3) the nanofiber or nanotube structure of the compositions of the present invention partially shields the drug and linker from the microenvironment, allowing the drug to be released from the conjugate in a controlled manner over time or under highly reducing conditions.

It will be understood by those of ordinary skill in the art that other peptide fragments which are hydrophilic and which can form a β-sheet or other secondary structure conformations can also be used in the compositions of the present invention. Examples of hydrophilic peptides include, but are not limited to, NNQQNY (SEQ ID NO: 2) (from the Sup35 yeast prion) and derivatives thereof, GRK-KRRQRRRPPQ (SEQ ID NO: 3) (from the HIV Tat protein) and derivatives thereof, LLKKLLKLLKKLLK (SEQ ID NO: 4) (alpha helical peptide) and derivatives thereof, and de novo sequences such as those that possess alternate hydrophobic and hydrophilic residues.

In one or more additional embodiments, the PEP portion of the drug amphiphile of the present invention is selected from the following peptide sequences: GVQIVYKK (SEQ ID NO: 1); NNQQNY (SEQ ID NO: 2); GRKKRRQR- RRPPQ (SEQ ID NO: 3); LLKKLLKLLKKLLK (SEQ ID NO: 4); CGNNQQNYKK (SEQ ID NO 5); CGVQIVYKK (SEQ ID NO: 6); GNNQQNYKK (SEQ ID NO: 7); GNNQQNY (SEQ ID NO: 8); VQIVYK (SEQ ID NO: 9) and CCKGNNQQNYKK (SEQ ID NO: 10) and derivatives thereof, wherein the derivatives comprise 1 to 10 additional amino acids on either the N-terminal or C-terminal end of PEP.

In accordance with an embodiment, the present invention provides a pharmaceutical composition comprising: D-L-PEP; wherein D is 1 to 4 hydrophobic drug molecules; L is 1 to 4 biodegradable linkers; PEP is a peptide comprising a fragment of the Tau protein comprising 6 to 19 amino acids of the paired helical filament Tau protein; and one or more additional therapeutically active compounds and a pharmaceutically acceptable carrier.

It will be understood by those of ordinary skill in the art, that in some embodiments, D can represent two or more different hydrophobic drug molecules. For example, D can include a first drug (D1) and second drug (D2) which can be, for example, chemotherapeutic agents which are not the same. In other embodiments, D can represent three or four different drug molecules (D1, D2, D3, D4) each linked by a biodegradable linker, which can be the same or different, to a PEP portion of the molecule of the present invention. Without being limited to any particular example, the pharmaceutical composition of the present invention can be a hetero-dual drug amphiphile comprising a first drug molecule of camptothecin (CPT) and a second drug molecule of paclitaxel (PXL) linked by the same or different linker, for example buSS, to the PEP portion, for example, Sup35.

In accordance with yet another embodiment, the present invention provides a method of treating a disease in a subject comprising administering to the mammal a therapeutically effective amount of the compositions described above, sufficient to slow, stop or reverse the disease in the mammal.

In accordance with an alternative embodiment, the drug amphiphiles of the present invention can be made with a targeting ligand (T) to bind a specific protein, receptor, or peptide, or other small molecule.

In accordance with an embodiment, the present invention provides a DA composition comprising: D-L-PEP-T; wherein D is 1 to 4 hydrophobic drug molecules; L is 1 to 4 biodegradable linkers; and PEP is a hydrophilic peptide that can promote the formation of specific nanostructure architectures, and T is a targeting ligand.

Without being limited to any particular example, targeting ligands can be incorporated into the molecular design of the DA conjugates using one of two approaches, dependent upon their nature. The first is incorporation during the synthesis of the peptide (solid phase) and the second is incorporation after the peptide has been purified or once the DA has been synthesized (both solution phase). If performed in solution, the chemistry chosen for incorporation would ideally be orthogonal to that used to conjugate the drug molecules.

Peptide-based ligands including, but not limited to, integrin binding peptides such as RGD, RGDS (SEQ ID NO: 13) and similar derivatives, prostate specific membrane antigen (PSMA) ligands, etc, can be directly introduced as part of the peptide sequence (PEP), using the same solid phase Fmoc peptide synthesis techniques.

For example, the following listing of peptides, proteins, and other large molecules may also be used, such as interleukins 1 through 18, including mutants and analogues; interferons a, y, hormone releasing hormone (LHRH) and analogues, gonadotropin releasing hormone transforming growth factor (TGF); fibroblast growth factor (FGF); tumor necrosis factor-α); nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, may be used as the targeting ligand in the DAs of the present invention. Members of the TGF supergene family include the beta transforming growth factors (for example, TGF-131, TGF-132, TGF-133); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (1GF)), (for example, lnhibin A, lnhibin B), growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Both peptide-based ligands (as described above) and small molecule targeting ligands, including but not limited to, folate-receptor binding molecules such as folate and methotrexate, can be incorporated using common conjugation techniques. These include, but are not limited to, amide bond formation (requiring a lysine, glutamic acid or aspartic acid group at the periphery of the peptide, the C-terminal for instance), reaction with a cysteine thiol (thiol-ene reaction, disulfide formation, thioether formation) or through Click reactions such as azide-alkyne cycloaddition. These conjugations may require suitable modification of the ligand to provide the required functionality, and may be performed on the solid-phase during synthesis of the peptide or in solution before or after the drug molecule(s) is attached.

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications. A particular example of a pharmaceutically active compound is a chemotherapeutic agent.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids. Further examples of chemotherapeutic agents include asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

It will be understood that any hydrophobic chemotherapeutic agents can be conjugated to the biodegradable linker as defined in the present invention. Examples include camptothecin, paclitaxel, anthracyclines, carboplatin, cisplatin, daunorubicin, doxorubicin, methotrexate, vinblastine, vincristine, etc.

For purposes of the invention, the amount or dose of the compositions of the present invention that is administered should be sufficient to effectively target the cell, or population of cells in vivo, such that cell apoptosis or death in the target cell or population of cells occurs in the subject over a reasonable time frame. The dose will be determined by the efficacy of the particular pharmaceutical formulation and the location of the target population of cells in the subject, as well as the body weight of the subject to be treated.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent" "pharmacologically active agent" and "drug" are used, then, it is to be understood that the invention includes the active agent per se, as well as pharmaceutically acceptable, pharmacologically active salts, esters, amides, prodrugs, metabolites, analogs etc.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the pharmaceutical compositions of the present invention can be at a concentration from about 1 nM to about 10,000 nM, preferably from about 10 nM to about 5,000 nM, more preferably from about 100 nM to about 500 nM.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In accordance with an embodiment of the present invention, the medicament for treating a disease in a subject can encompass many different formulations known in the pharmaceutical arts, including, for example, intravenous and sustained release formulations. With respect to the inventive methods, the disease can include cancer. Cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

In another embodiment, the term "administering" means that at least one or more pharmaceutical compositions of the present invention are introduced into a subject, preferably a subject receiving treatment for a disease, and the at least one or more compositions are allowed to come in contact with the one or more disease related cells or population of cells.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Other non-limiting examples of biologically active agents which can be included in the drug amphiphile compositions of the present invention include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: (a) anti-neoplastics such as androgen inhibitors, antimetabolites, cytotoxic agents, and immunomodulators.

The "therapeutically effective amount" of the pharmaceutical compositions to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as cancer.

In accordance with another embodiment, the present invention provides methods of treating cancer in a subject comprising administering to the mammal a therapeutically effective amount of the composition of the present invention sufficient to slow, stop or reverse the cancer in the subject.

In accordance with an embodiment, the present invention provides a pharmaceutical composition comprising a therapeutically effective amount of the compositions described herein, for use in a medicament, preferably for use in treating a proliferative disease in a subject.

In accordance with a further embodiment, the present invention provides a pharmaceutical composition comprising a therapeutically effective amount of the compositions described herein, for use in a medicament, preferably for use in treating a tumor in a subject sufficient to slow, stop or reverse the growth of the tumor in the subject.

In accordance with still another embodiment, the present invention provides pharmaceutical composition comprising a therapeutically effective amount of the compositions described herein, for use in a medicament, preferably for use in treating cancer in a subject sufficient to slow, stop or reverse the cancer in the subject.

In accordance with a further embodiment, the present invention provides a method for making the compositions described above comprising: a) dissolving the chemotherapeutic agent in a mixture comprising dichloromethane and dimethylaminopyridine; b) adding to the solution of a sufficient amount of 4-(pyridin-2-yldisulfanyl)butanoic acid and diisopropylcarbodiimide and stirring until the chemotherapeutic agent is dissolved; and c) extracting the solution of b) with saturated $NaHCO_3$ and drying.

It will be understood by those of skill in the art that the methods for making the compositions of the present invention can use any known solvents or mixtures thereof that will dissolve the chemotherapeutic agent. Moreover, other linkers can be used in the inventive methods to prepare the drug amphiphiles of the present invention. Known methods for extraction of the mixtures and drying can also be used.

These and other aspects of the present invention will be further appreciated upon consideration of the following Examples, which are intended to illustrate certain particular embodiments of the invention but are not intended to limit its scope, as defined by the claims.

Example 1

Self-Assembly and Properties of a CPT-buSS-Tau DA Conjugate

To illustrate the feasibility of the present invention, a series of camptothecin (CPT) DA conjugates were synthesized by reaction of an activated disulfide-functionalized CPT molecule with Tau protein-derived peptide that has 1, 2 or 4 cysteine residues (FIG. 1). These conjugates were purified to homogeneity by reversed phase HPLC and their identity confirmed by mass spectrometric methods.

Figure 2:
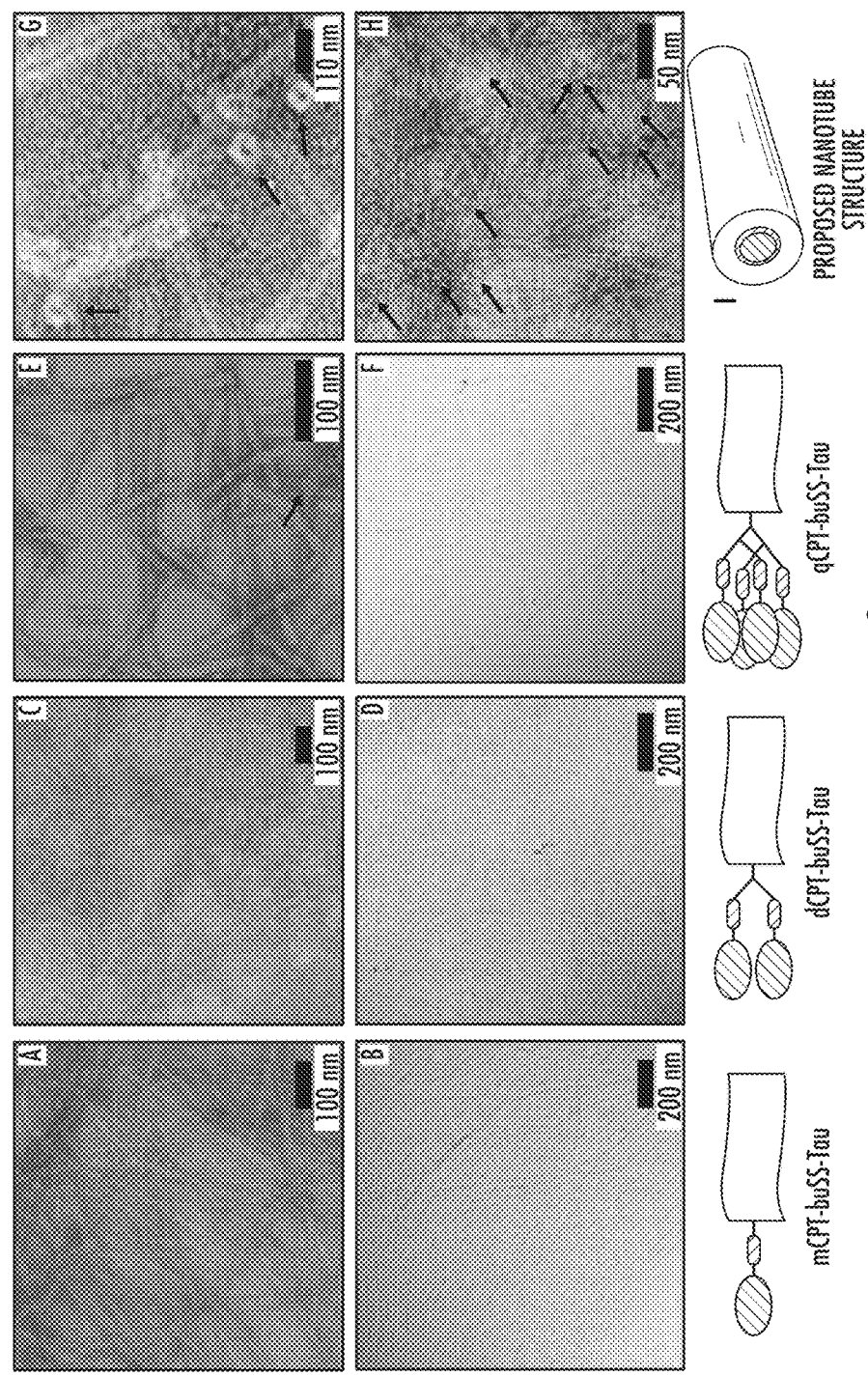
FIGS. 2A-2I show the TEM characterization of the drug amphiphiles. TEM (a) and cryo-TEM (b) images of long filaments of widths 6.7±1 nm formed by mCPT-buSS-Tau in water and a self-supporting gel formed at 5 mM in 1×PBS (inset). TEM (c) and cryo-TEM (d) images of shorter filaments of widths 7.2±1.4 nm formed by dCPT-buSS-Tau in water. TEM (e) and cryo-TEM (f) images of nanotubes of widths 9.5±1 nm formed by qCPT-buSS-Tau in water. The cryo-TEM (f) resolution is insufficient to show the tubular nature. (g) High resolution TEM image of the tubular morphology formed by qCPT-buSS-Tau. The circular shape of the terminal ends (marked with white arrows) confirms the tubular structures. (h) TEM images of long nanotubes formed by qCPT-buSS-Sup35. (i) Schematic illustration of the proposed nanotube morphology. TEM samples for images of (a), (c), (e), (g) and (h) were stained with 2% uranyl acetate aqueous solution to enhance the image contrast. Solution concentrations: 50 μM for (a), (c), (e), (g) and (h); 1 mM for (b) and (d); 100 μM for (f).

The assembly of these conjugates into fibrous nanostructures was confirmed by dissolution into aqueous solution and subsequent transmission electron microscopy (TEM) and cryo-TEM analysis (FIG. 2). Both mCPT-buSS-Tau (FIGS. 2a and 2b) and dCPT-buSS-Tau (FIGS. 2c and 2d) were observed to form long nanofibers of widths 6.7±1 and 7.2±1.4 nm, respectively. Given these diameters are close to the expected molecular lengths (3.5 and 3.8 nm, respectively), it indicates these are core-shell micellar structures with the CPT moiety sequestered at the core. qCPT-buSS-Tau(FIG. 2e-g) was observed to form filamentous structures of 9.5 nm in width, with a dark centerline observed throughout the nanostructures. This dark centreline is due to the deposition of the negative staining agent, uranyl acetate, and suggests the structures possess a hollow core that may have collapsed during TEM sample preparation. The similarity of these structures to those of the tobacco mosaic virus and other structures in the literature suggest that qCPT-buSS-Tau adopts a nanotube structure. This is further confirmed by the observation of circular ends at the termini ends (FIG. 2g). The comparable value of the nanotube wall thickness to the molecular length (4 nm vs. 4.1 nm) implies that the molecules are packed in a monolayered rather than bilayered fashion. These results demonstrate that the incorporation of different numbers of CPT units into the drug amphiphiles can tune both the drug loading content and the assembly morphologies.

The leading role of the Tau peptide in promoting the formation of 1-dimensional nanostructures was confirmed by circular dichroism (CD) spectroscopy, with all conjugates showing the characteristic negative signal of the beta sheet in the 220 nm region (FIG. 3a-c).

The morphological differences between the conjugates can be ascribed to the number of CPT molecules that each possesses. Both mCPT-buSS-Tau (FIG. 3a) and dCPT-buSS-Tau (FIG. 3b) show strong negative signals in the CPT absorption region (at 250 nm and between 330 and 400 nm), clearly indicated they are packed in a chiral environment. These signals were absent in DMSO (FIG. 4), where the conjugates are expected to exist as single monomers. qCPTbuSS-Tau (FIG. 3c) on the other hand displayed two bisignate CD signals at 265 and 366 nm and a strong positive signal at 389 nm. This bisignate Cotton effect is frequently observed in aggregated π-conjugated systems, resulting from excitonic coupling between two adjacent chromophores in a chiral orientation. The positive sign of the couplet signal at the higher wavelength suggests a positive chirality and a right-handed helical arrangement of the CPT molecules within the nanotubes.

The critical micellization concentrations of mCPT-buSS-Tau, dCPT-buSS-Tau and qCPT-buSS-Tau were determined to be 207 nM, 74 nM and 53 nM, respectively, by a fluorescence method (FIG. 5). These very low values are in the range of macromolecular amphiphiles and are an important property of these conjugates. A high value would lead to rapid dissociation of the nanostructure when diluted upon introduction into the bloodstream, whereas a low value would impart greater stability to the assembly during circulation.

Fluorescence analysis (FIG. 6) also shows that the CPT is present as the closed lactone form with emission maxima around 433 nm, rather than the open carboxylic acid (maxima around 446 nm). This is critical for it to exert a cytotoxic effect as the open carboxylic acid form is inactive. The combination of both conjugation to the hydroxyl and sequestering within a hydrophobic core act to shift the equilibrium between the closed and open forms towards the active closed (lactone) form.

The shielding of the degradable linker from the microenvironment afforded by assembly into the nanostructures was confirmed by a degradation study that showed the conjugates were stable in 10 mM phosphate solutions at 37° C., at concentrations far above their CMC values (FIGS. 3d and 3e). In the presence of the reducing agent glutathione, however, faster release was observed. The differences in release rates between the conjugates can be ascribed to their CMC values, with lower values resulting in a greater stability towards both reduction and hydrolysis. These observations suggest a release mechanism as depicted in FIG. 3f, indicating that the self-assembled nanostructures can serve as reservoirs to provide a consistent supply of CPT conjugate monomers that can be quickly converted to bioactive CPT in the presence of GSH and maintain an effective intracellular concentration.

Figures 8A, 8B, 8C, 8D, 8E, 8F:
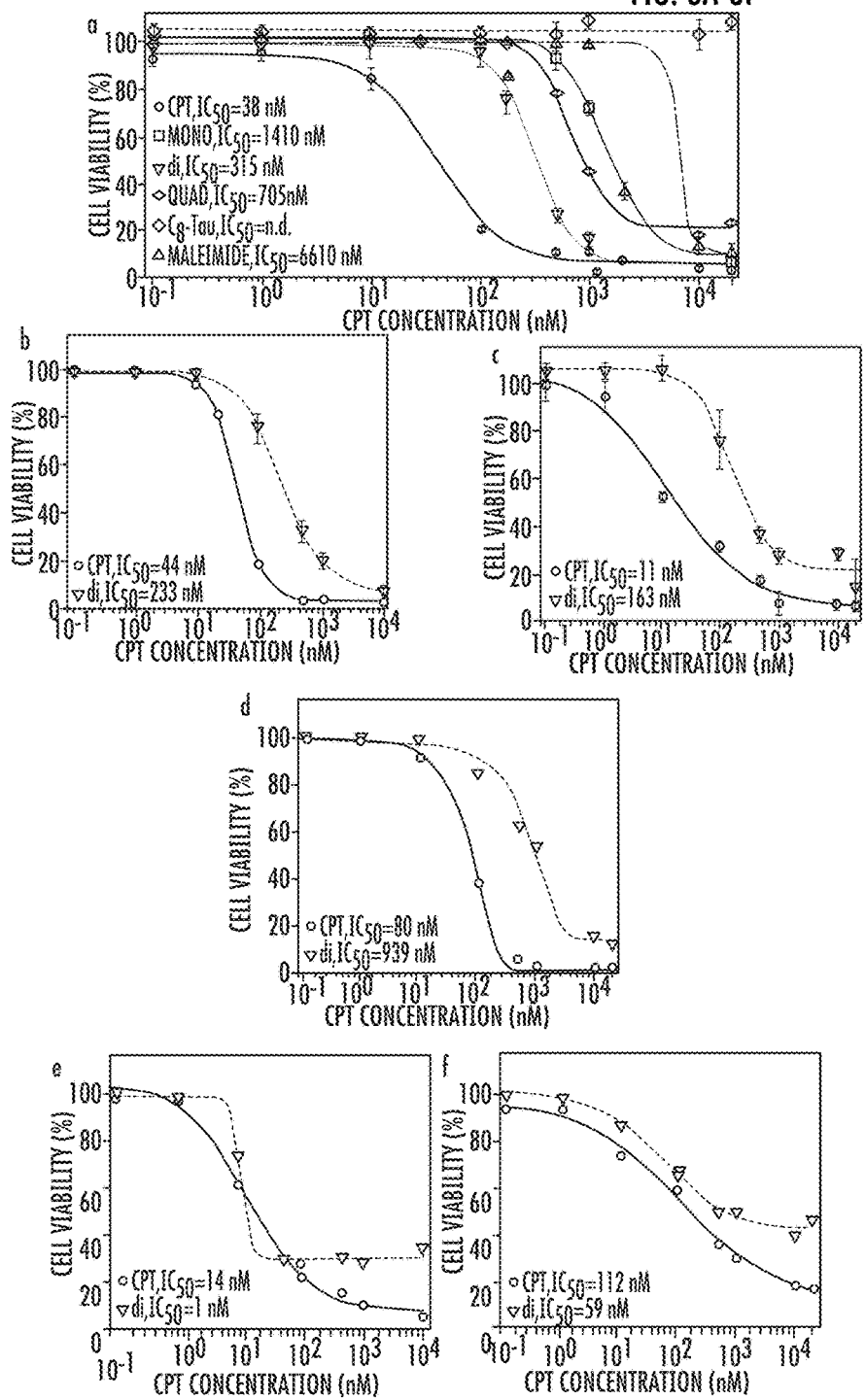
FIGS. 8A-8F shows an in vitro dose-response relationship study of the DA molecules against rat F98L gliosarcoma cells (a), and dCPT-buSS-Tau against murine ID-8 ovarian cancer (b), human NCI-H82—small cell lung cancer (c) and human TC-1 cervical cancer (d) cells human A459 non-small cell lung cancer (e) and human MDA-MB-231 breast cancer (f). All cancer cells were incubated with the appropriate DA molecules for 48 hours and cell viability was determined by SRB assay (n.d.=not determined).

In vitro efficacy of the synthesized DA conjugates towards a number of cancer cell lines (FIGS. 7 and 8) was determined by sulforhodamine (SRB) assay, showing that these amphiphiles can exert a cytotoxic effect.

Methods for Example 1

Figures 9A, 9B, 9C, 9D:
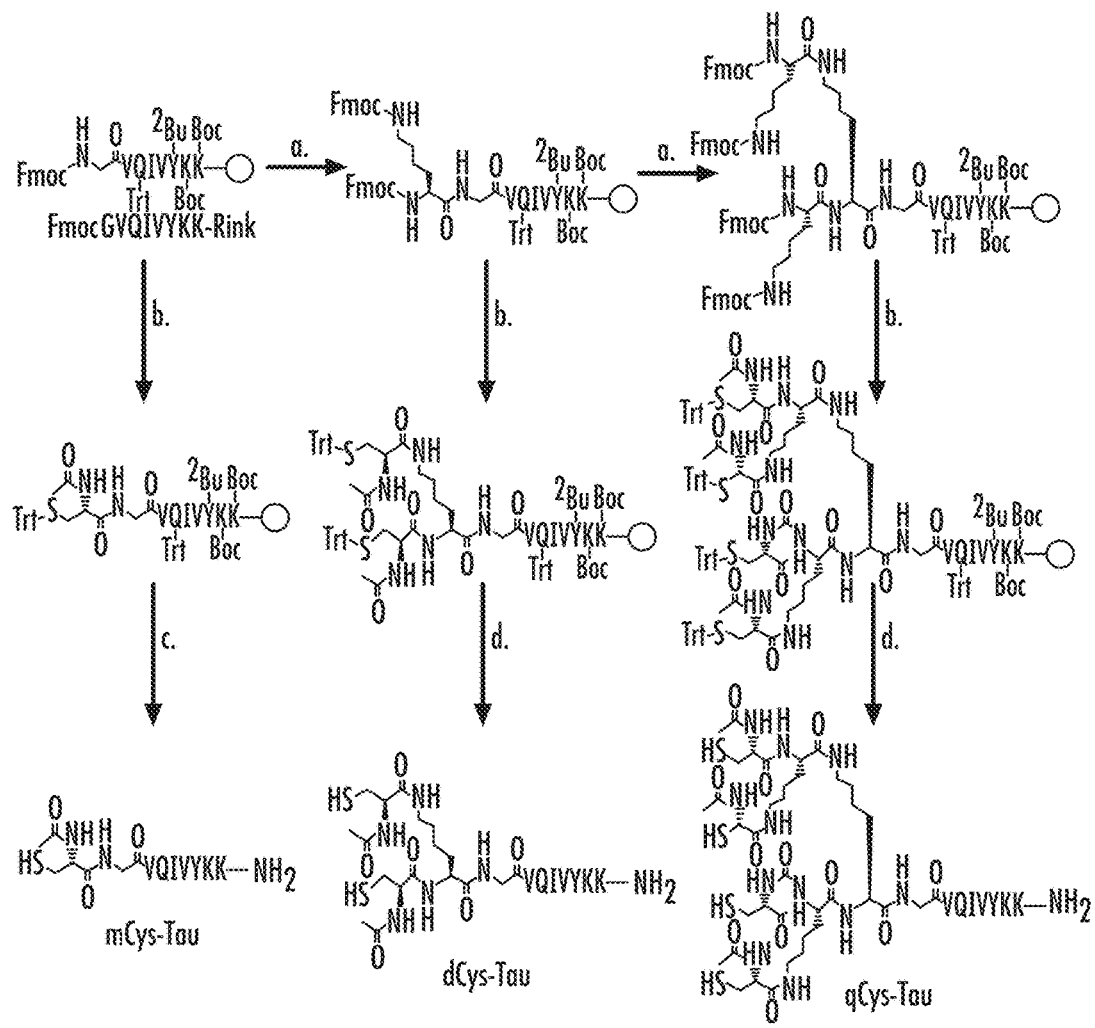
FIGS. 9A-9D illustrates the solid-phase synthesis of the cysteine-functionalized Tau precursor peptides. Fmoc-GVQIVYKK-Rink was created using an automated peptide synthesizer and further modified by manual synthesis techniques. Reaction conditions: (a) (i) 20% 4-methylpiperidine in DMF, (ii). Fmoc-Lys(Fmoc)-OH, HATU, DIEA (4:3.98:6 per amine); (b) (i). 20% 4-methylpiperidine in DMF, (ii) Fmoc-Cys(Trt)-OH, HATU, DIEA (4:3.98:6 per amine), (iii) 20% 4-methylpiperidine in DMF, (iv) 20% acetic anhydride in DMF, DIEA; (c) TFA, TIS, H2O (95:2.5:2.5); (d) TFA, TIS, H$_2$O, EDT (90:5:2.5:2.5).

All peptides were synthesized by a combination of automated and manual Fmoc solid-phase synthesis techniques. Automated synthesis of Fmoc-GVQIVYKK-Rink (SEQ ID NO: 1) was performed using the Focus XC automated peptide synthesizer (AAPPTEC, Louisville, Ky.) using the appropriate Fmoc amino acids (AAPPTEC) and HBTU/DIEA (4:3.98:6 relative to the amine). Terminal cysteines and branching lysines were added manually as appropriate, using HATU instead of HBTU as the coupling agent in the same ratio as described above. 20% 4-methylpiperidine in DMF was used for Fmoc deprotections and 20% acetic anhydride in DMF was used for N-terminal acetylation. Peptides were cleaved from the resin using trifluoroaceticacid (TFA)/triisopropylsilane(TIS)/H$_2$O (95:2.5:2.5) for mCys-Tau and TFA/TIS/H$_2$O/ethane-dithiol (EDT) (90:5:2.5:2.5) for dCys-Tau and qCys-Tau (FIG. 9).

Figure 10:
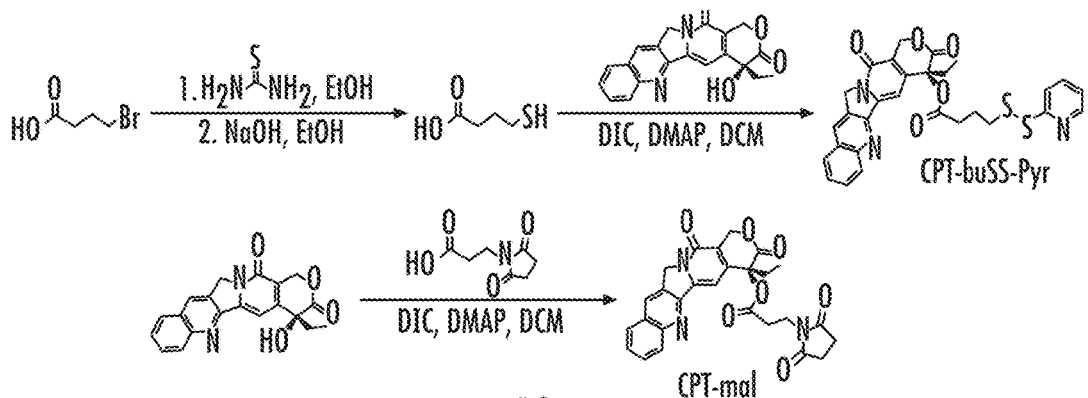
FIG. 10 illustrates the scheme for the synthesis of the CPT-linker molecules, CPT-buSS-Pyr and CPT-mal.

The syntheses of the CPT-linker derivatives CPT-buSS-Pyr and CPT-Malare shown in FIG. 10.

Synthesis of 4-(pyridin-2-yldisulfanyl)butanoic acid (buSS-Pyr). buSS-Pyr was prepared using a modified version of a previously reported method. Briefly, 4-Bromobutyric acid (2.00 g, 12.0 mmol) and thiourea (1.06 g, 14.0 mmol) were refluxed in EtOH (50 ml) for 4 hours. NaOH (4.85 g, 121 mmol) in EtOH (50 ml) was added and reflux was continued for 16 hours. After cooling to room temperature, the solution was filtered and the filtrate concentrated in vacuo and dissolved in H$_2$O (50 ml). Acidification to pH 5 with 4M HCl gave a cloudy solution that was then extracted with Et$_2$O. The organic extracts were dried over anhydrous Na$_2$SO$_4$ and concentrated to give 4-sulfanylbutyric acid as a clear oil (816 mg) that was used without further purification. 4-Sulfanylbutyric acid (816 mg, 6.68 mmol) was dissolved in MeOH (1 ml) and added dropwise to a solution of 2-aldrithiol (3.03 g, 13.7 mmol) in MeOH (5 ml), which developed a yellow color, and was allowed to react overnight. The mixture was purified by reversed phase HPLC, collecting the major peak. The fractions were combined and lyophilized to give buSS-Pyr as a pale yellow viscous oil (1.02 mg, 37% over two steps). $^1$H NMR (CDCl$_3$, 400 MHz, 298K): $\delta_H$ (ppm) 8.59 (d, $^3J_{HH}$=4.6, 1H), 7.91-7.81 (m, 2H), 7.30-7.25 (m, 1H), 2.88 (t, $^3J_{HH}$=7.1, 2H), 2.50 (t, $^3J_{HH}$=7.2, 2H), 2.09-2.00 (m, 2H).

Figures 11A, 11B:
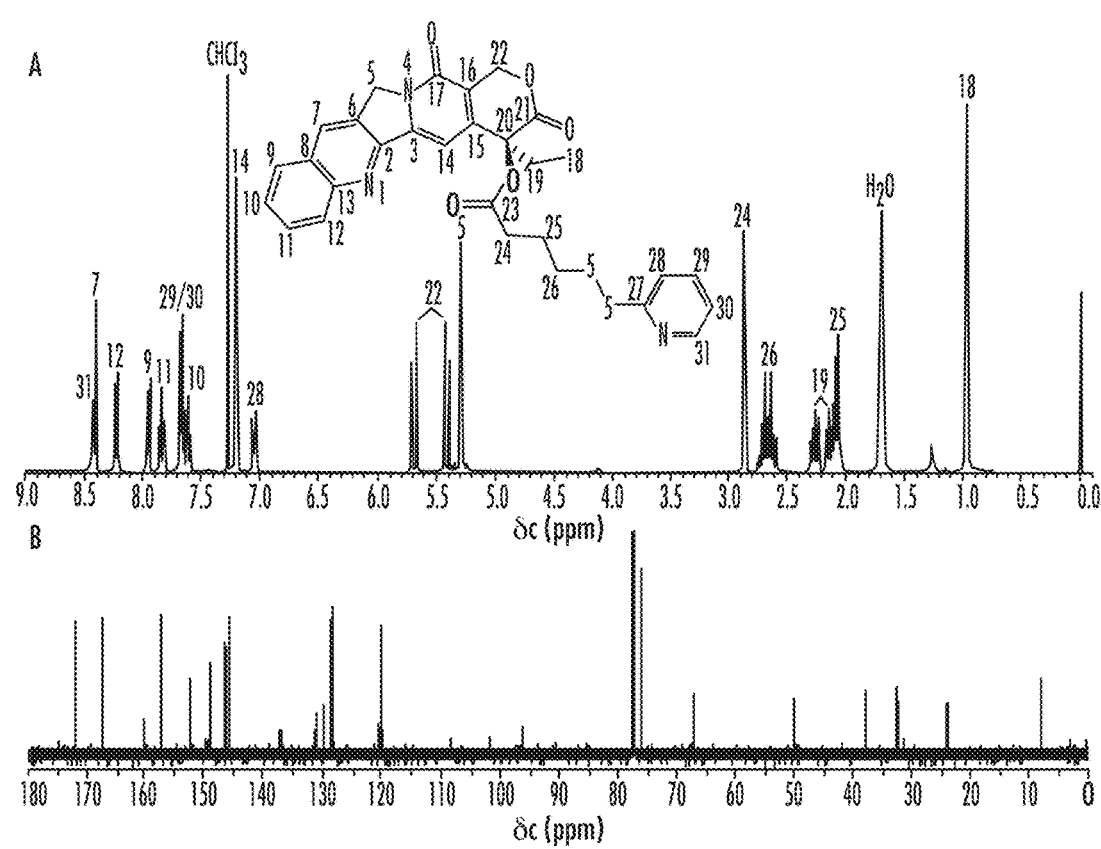
FIGS. 11A-11B (A) $^1$H NMR (CDCl$_3$, 400 MHz, 298K) and (B)$^{13}$C NMR (CDCl$_3$, 100 MHz, 298K) of CPT-buSS-Pyr.

Synthesis of camptothecin-4-(pyridin-2-yldisulfanyl)butanoate (CPT-buSS-Pyr). CPT-buSSPyr was synthesized using a modified version of a previously reported method. Camptothecin (200 mg, 0.574 mmol) was suspended in DCM (32 ml) and dimethylaminopyridine (44 mg, 0.36 mmol), buSS-Pyr (208 mg, 1.22 mmol) and diisopropylcarbodiimide (436 µl, 3.51 mmol) were added. The mixture was stirred until complete dissolution of the camptothecin had occurred (1.5 days), with TLC (3% MeOH in CHCl$_3$) showing complete consumption. The solution was then filtered, diluted with CHCl$_3$ (30 ml), extracted with sat. NaHCO$_3$ (50 ml), brine (50 ml), dried over Na$_2$SO$_4$ and concentrated in vacuo. The residue was purified by flash chromatography using EtOAc (1:1 500 ml) then 0.5% MeOH in EtOAc (250 ml). Product fractions were identified by TLC, combined and solvent removed in vacuo to give CPT-buSS-Pyr as a pale yellow solid (195 mg, 61%); $^1$H NMR (CDCl$_3$, 400 MHz, 298K): $\delta_H$ (ppm) 8.43 (d, 3J$_{HH}$=4.2, 1H), 8.40 (s, 1H), 8.23 (d, $^3J_{HH}$=8.6, 1H), 7.94 (d, $^3J_{HH}$=8.2, 1H), 7.84 (m, 1H), 7.70-7.65 (m, 2H), 7.60 (m, 1H), 7.20 (s, 1H), 7.04 (m, 1H), 5.67 (d, $^2J_{HH}$=17.3, 1H), 5.40 (d, $^2J_{HH}$=17.2, 1H), 5.29 (s, 2H), 2.86 (t, $^3J_{HH}$=7.1, 2H), 2.75-2.57 (m, 2H), 2.31-2.03 (m, 4H), 0.97 (t, $^3J_{HH}$=7.5); $^{13}$C NMR (CDCl$_3$, 100 MHz, 298K): $\delta_C$ (ppm) 172.1, 167.7, 160.3, 157.6, 152.6, 149.9, 149.1, 146.6, 146.1, 137.3, 131.5, 131.4, 130.9, 129.9, 128.63, 128.62, 128.4, 128.3, 120.4, 96.1, 76.2, 67.4, 50.2, 37.7, 32.4, 32.0, 31.2, 24.0, 7.9 (FIG. 11); MS (MALDI-TOF): 560.065 [M+H]$^+$.

Figures 12A, 12B:
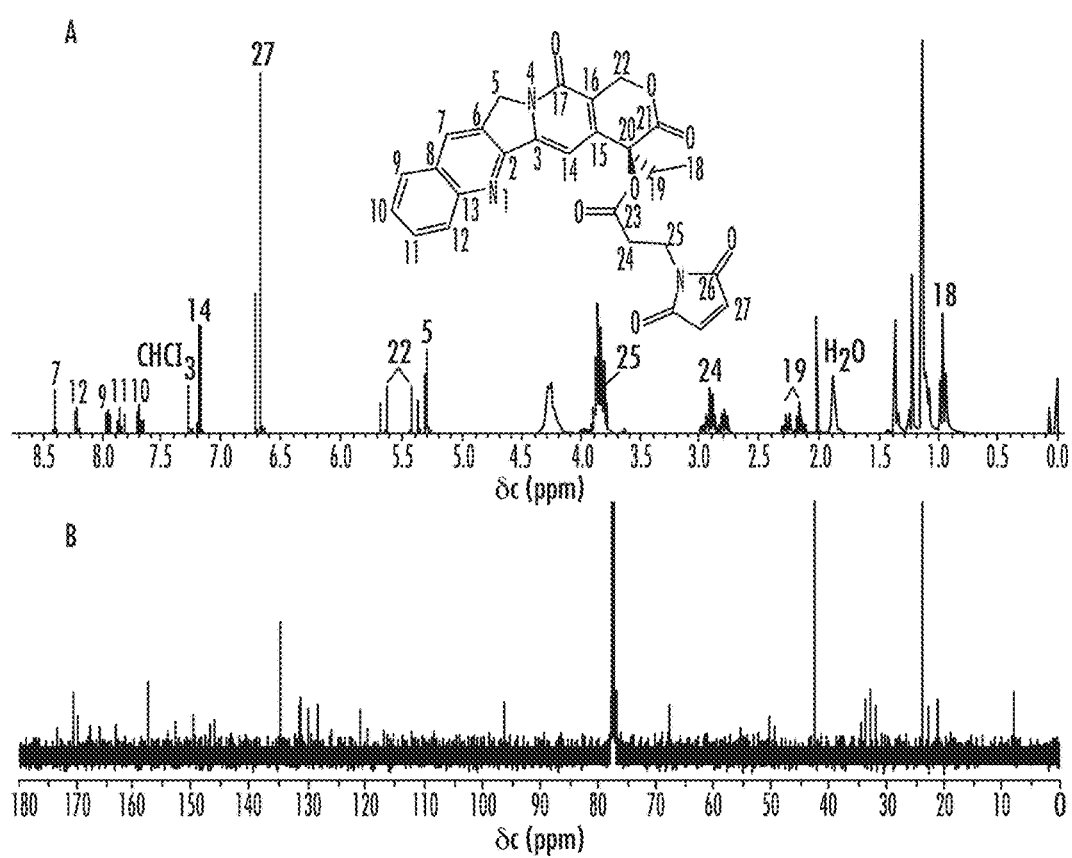
FIGS. 12A-12B (A) $^1$H NMR (CDCl$_3$, 300 MHz, 298K) and (B)$^{13}$C NMR (CDCl$_3$, 100 MHz, 298K) of CPT-Mal.

Synthesis of camptothecin-3-maleimido-propanoate (CPT-mal). CPT (50 mg, 0.144 mmol) was suspended in DCM (8 ml) and DMAP (11 mg, 0.093 mmol), 3-maleimido-propionic acid (70 mg, 0.288 mmol) and DIC (109 µl, 0.698 mmol) were added. The mixture was stirred until complete dissolution of CPT had occurred (overnight), with TLC (3% MeOH in CHCl$_3$) showing complete consumption. The solution was then diluted with CHCl$_3$ (30 ml), extracted with H$_2$O (20 ml), sat. NaHCO$_3$ (20 ml), brine (20 ml), dried over Na$_2$SO$_4$ and concentrated in vacuo. The residue was purified by flash chromatography using 3% MeOH in CHCl$_3$. Product fractions were identified by TLC, combined and solvent removed in vacuo to give CPT-mal as an off-white solid (37 mg, 51%). NMR showed a maleimide impurity, but only a single CPT compound—this was used without further purification; $^1$H NMR (CDCl$_3$, 300 MHz, 298K): $\delta_H$ (ppm) 8.41 (s, 1H), 8.24 (d, $^3J_{HH}$=8.0, 1H), 7.96 (d, 1H, $^3J_{HH}$=8.1, 1H), 7.85 (dd, $^3J_{HH}$=8.4, 1.5, 1H), 7.68 (dd, $^3J_{HH}$=8.2, 1.2, 1H), 7.19 (s, 1H), 6.67 (s, 2H), 5.66 (d, $^2J_{HH}$=17.2, 1H), 5.40 (d, $^2J_{HH}$=17.2, 1H), 5.30 (s, 2H), 3.95-3.75 (m, 2H), 3.00-2.85 (m, 2H), 2.35-2.08 (m, 2H), 0.96 (t, $^3J_{HH}$=7.5, 3H); $^{13}$C NMR (CDCl$_3$, 100 MHz, 298K): 170.6, 169.9, 167.6, 165.8, 162.8, 157.4, 152.6, 149.2, 146.6, 145.8, 131.6, 131.0, 129.9, 128.6, 128.4, 120.6, 96.3, 67.5, 50.3, 33.5, 32.6, 32.1, 22.8, 21.1, 7.9 (FIG. 12); MS (ESI): 499.9 [M+H]$^+$.

Figure 13A:
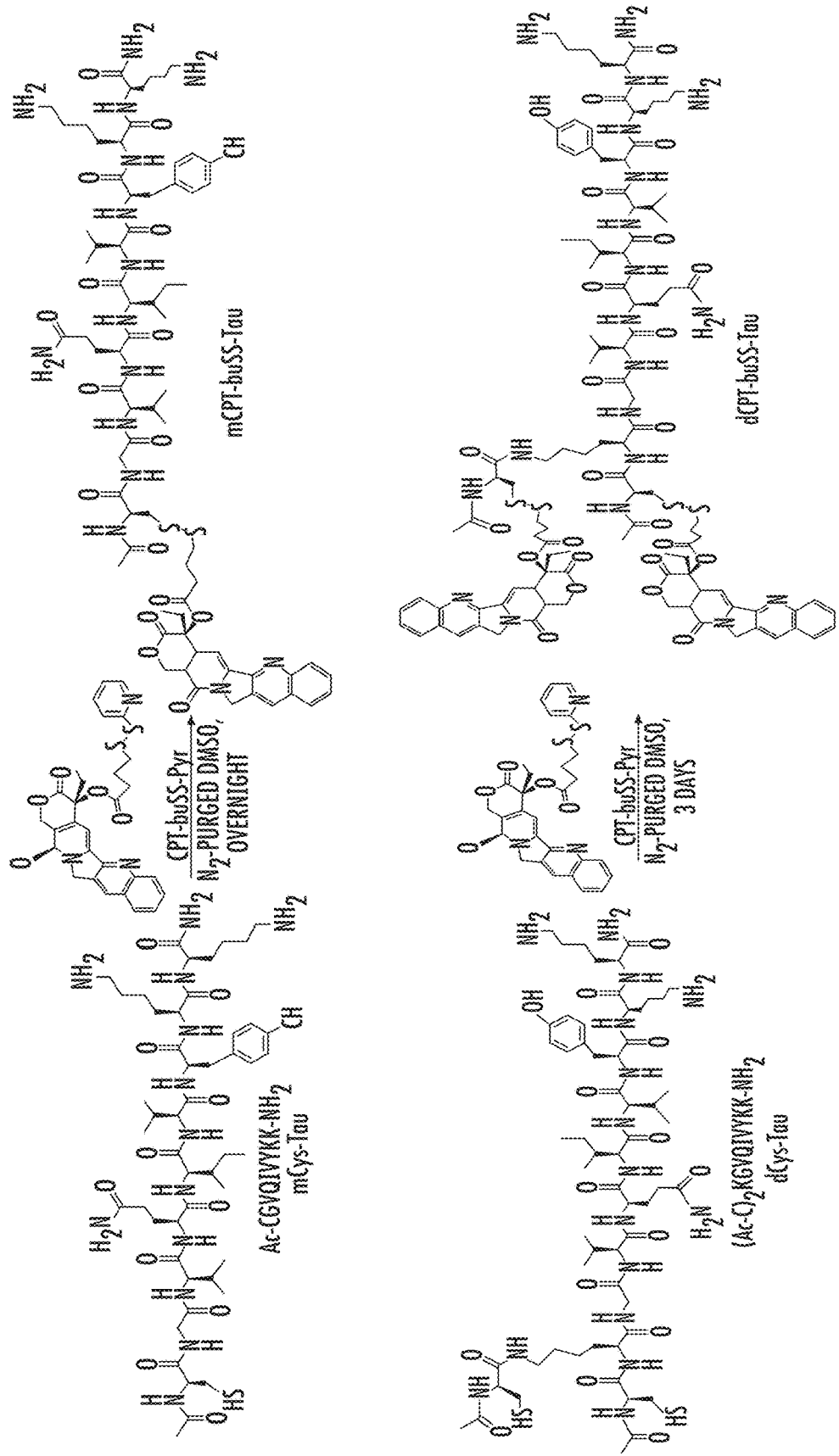
FIGS. 13A-13B (A) depicts the synthesis and (B) chemical structures of the drug amphiphiles of the present invention.
Figure 13B:
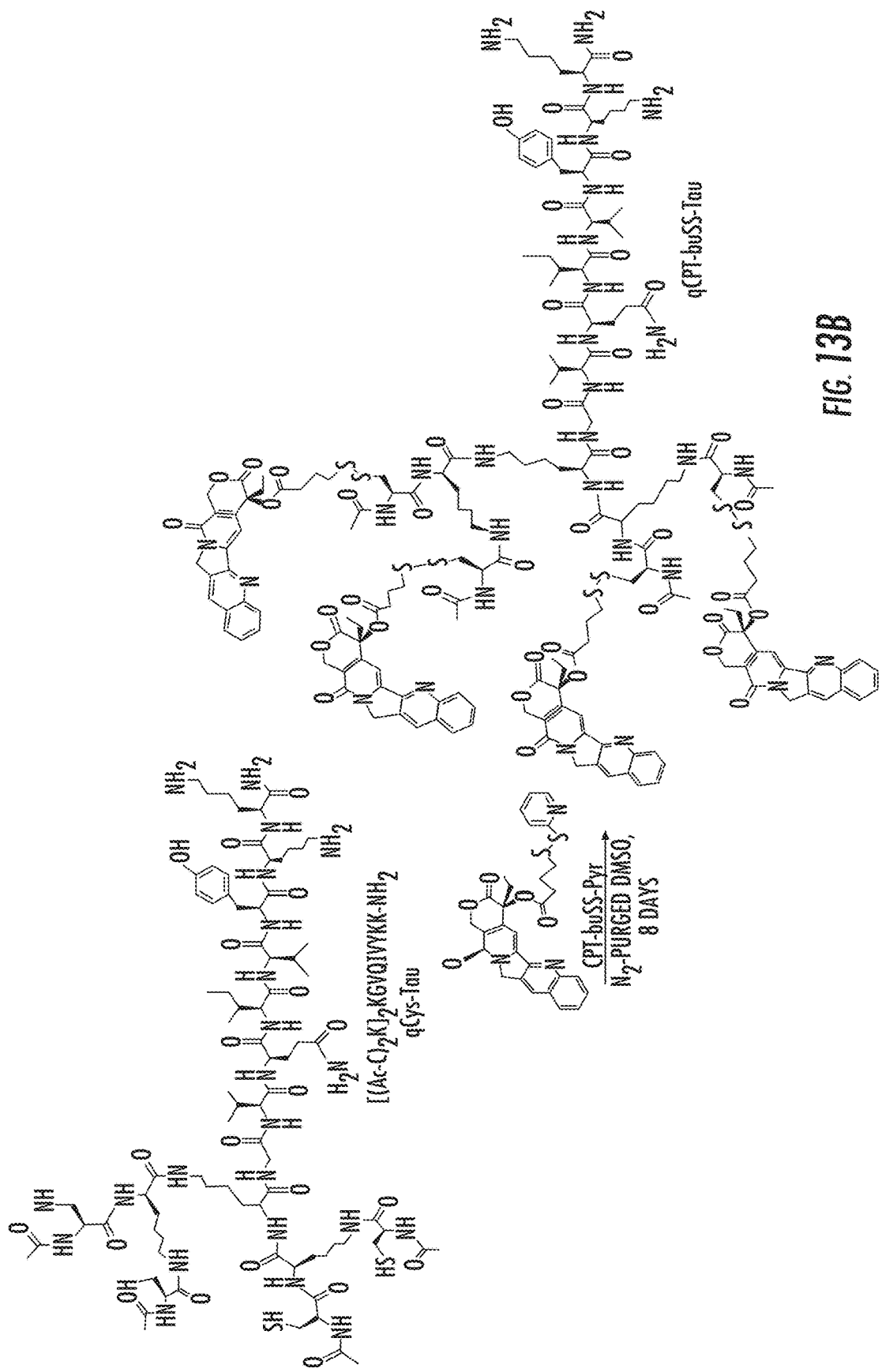

The synthesis of the DA conjugates mCPT-buSS-Tau, dCPT-buSS-Tau and qCPT-buSS-Tau are shown in FIG. 13.

Figures 14A, 14B:
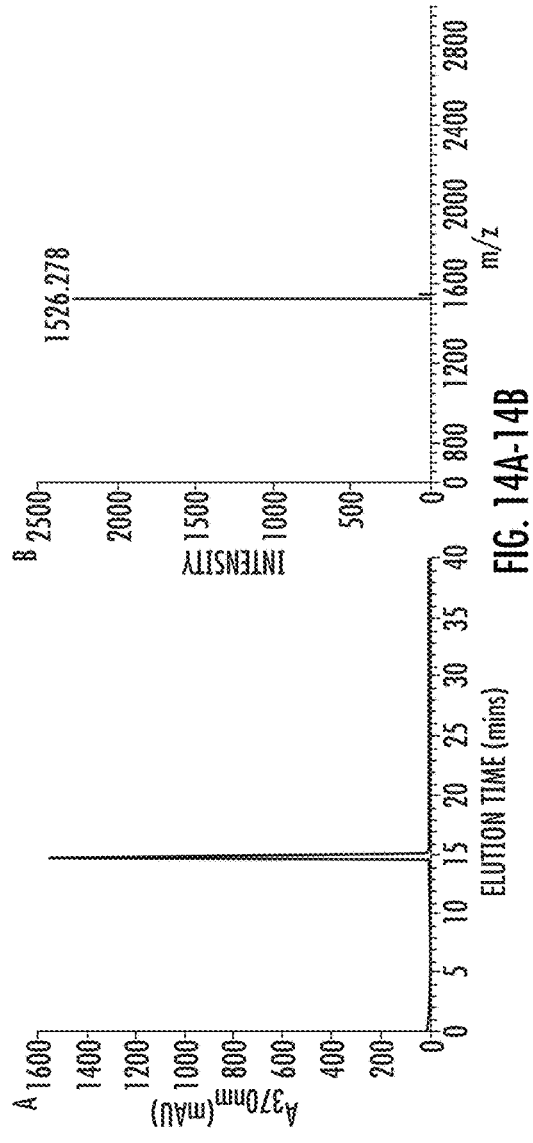
FIGS. 14A-14B depicts RP-HPLC (A) and MALDI-Tof MS (B) characterization of mCPT-buSS-Tau.

Synthesis of mCPT-buSS-Tau. mCys-Tau (14.6 mg, 13.5 μmol) was dissolved in an N$_2$-purged DMSO solution CPT-buSS-Pyr (10 mg in 1.50 ml, 17.8 μmol) and shaken overnight. The reaction was diluted to 30 ml with 0.1% aqueous TFA, giving a slightly viscous solution that was then purified by reversed phase HPLC. Product fractions were combined and immediately lyophilized. The pale-yellow solid obtained was dissolved in 25 ml nanopure water and the product concentration was determined by DTT calibration to be 233 μM (8.9 mg, 43%). The solution was then aliquotted into cryo-vials, lyophilized and stored at −30° C. HPLC purity >99%; MS (MALDI): 1526.78 [M+H]$^+$ (FIG. 14).

Figures 15A, 15B:
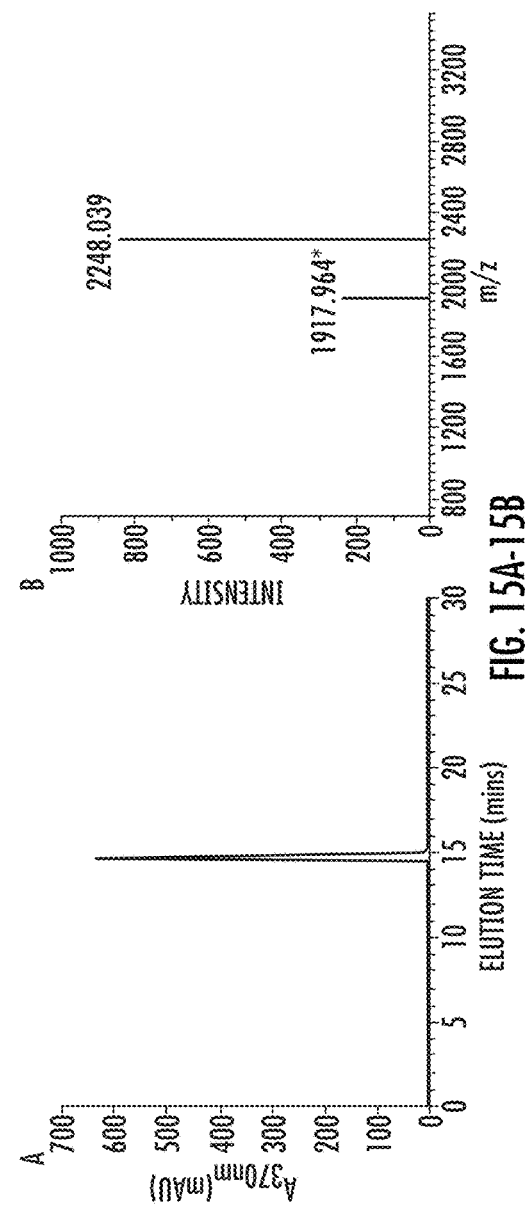
FIGS. 15A-15B shows RP-HPLC (A) and MALDI-Tof MS (B) characterization of dCPT-buSS-Tau. In-source fragmentation was observed corresponding to the loss of one CPT moiety (indicated by *).

Synthesis of dCPT-buSS-Tau. dCys-Tau (10.8 mg, 5.0 mmol) was dissolved in an N$_2$-purged DMSO solution of CPT-buSS-Pyr (9 mg in 500 μl, 16.1 μmol) and allowed to react for 3 days. The solution was diluted to 10 ml with 0.1% aqueous TFA and purified by reversed phase HPLC. Product fractions were combined and immediately lyophilized. The pale yellow solid obtained was dissolved in 15 ml nanopure water containing 0.08% TFA and 8% acetonitrile and the product concentration was determined by DTT calibration to be 72.9 μM (2.5 mg, 22%). The solution was then aliquotted into cryo-vials, lyophilized and stored at −30° C. HPLC purity >99%; MS (MALDI): 2248.039[M+H]$^+$ (FIG. 15).

Figures 16A, 16B:
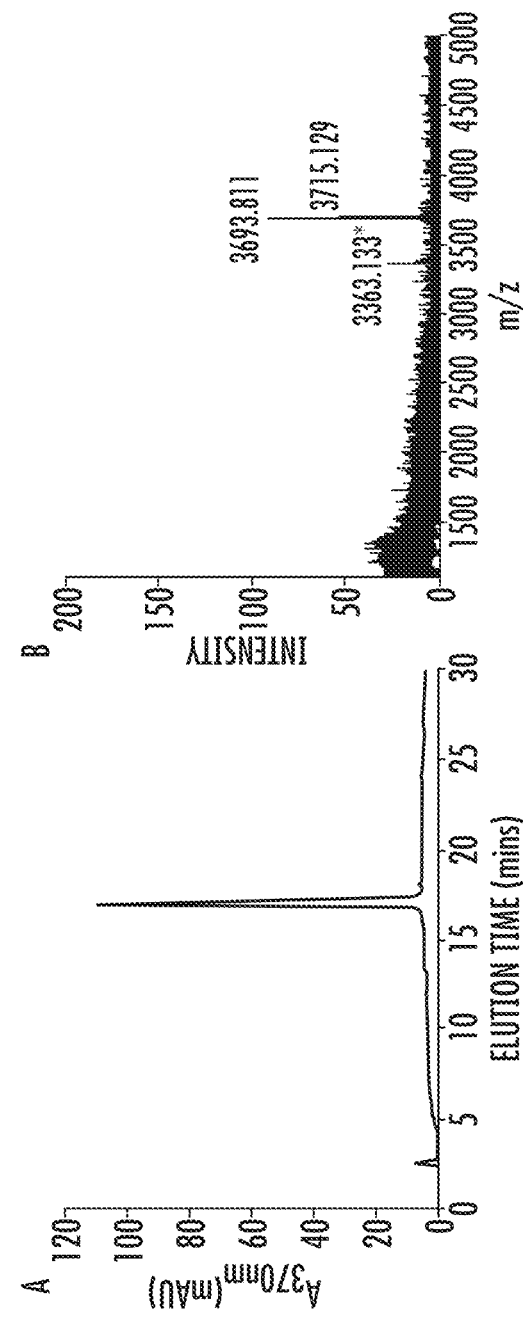
FIGS. 16A-16B is the RP-HPLC (A) and MALDI-Tof MS (B) characterization of qCPT-buSS-Tau. In-source fragmentation was observed corresponding to the loss of one CPT moiety (indicated by *). Higher laser power resulted in the loss of further CPT fragments.

Synthesis of qCPT-buSS-Tau. qCys-Tau (3.5 mg, 1.91 μmol) was dissolved in an N$_2$-purged DMSO solution of CPT-buSS-Pyr (10 mg in 500 μl, 17.8 μmol) and allowed to react for 8 days. The solution was diluted to 10 ml with 0.1% aqueous TFA and purified by reversed phase HPLC. Product fractions were combined and immediately lyophilized. The pale yellow solid obtained was dissolved in 19.5 ml nano-pure water containing 0.05% TFA and 25% acetonitrile and the product concentration was determined by DTT calibration to be 14.2 μM (1.0 mg, 15%). The solution was then aliquotted into cryo-vials, lyophilized and stored at −30° C. HPLC purity >99%; MS (MALDI): 3693.811[M+H]$^+$ (FIG. 16).

Figure 17:
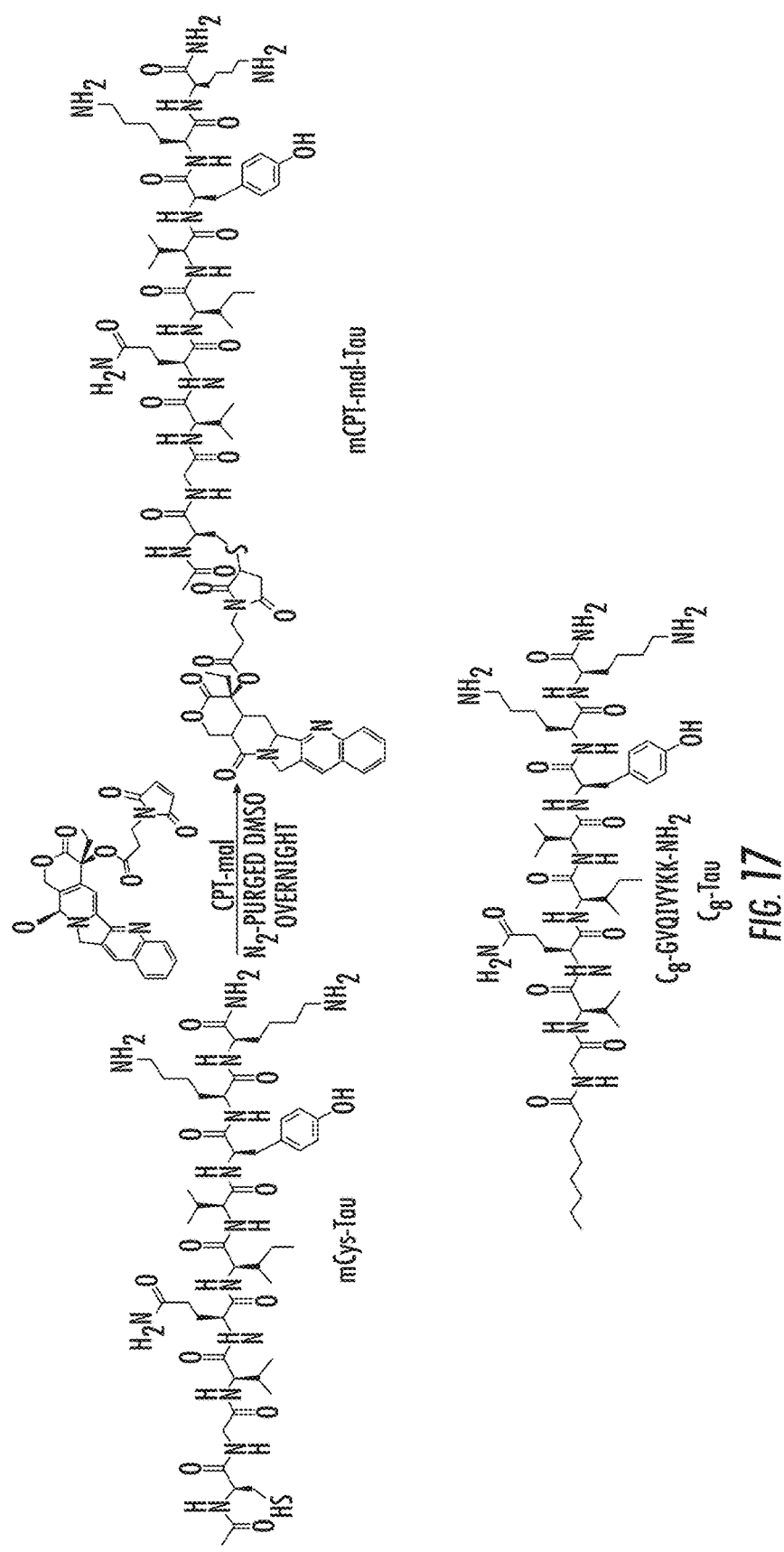
FIG. 17 is the general scheme for the synthesis of the control peptides.
Figure 18:
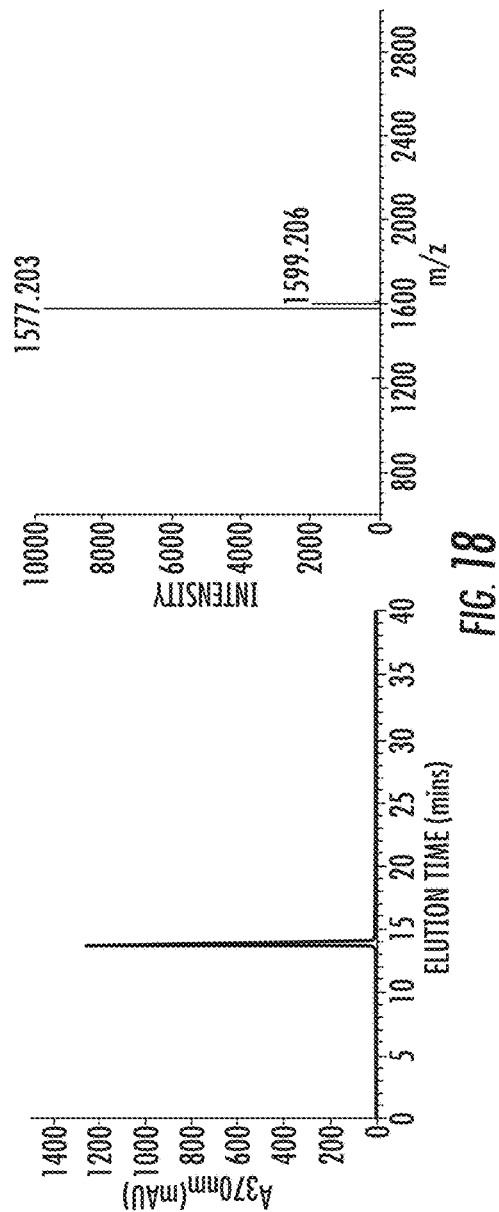
FIG. 18 depicts RP-HPLC (left) and MALDI-Tof MS (right) characterization of mCPT-mal-Tau.

Synthesis of mCPT-mal-Tau. The general scheme for synthesizing the control molecules is shown in FIG. 17. mCys-Tau (5.6 mg, 5.2 μmol) was dissolved in an N$_2$-purged DMSO solution of CPT-mal (2.6 mg in 250 μl, 5.2 μmol) and shaken overnight. The reaction was diluted to 10 ml with 0.1% aqueous TFA and purified by reversed phase HPLC. Product fractions were combined and immediately lyophilized. The white solid obtained was dissolved in 10 ml nanopure water and the product concentration was determined by HPLC calibration to be 273 μM (4.3 mg, 53%). The solution was then aliquotted into cryo-vials, lyophilized and stored at −30° C. HPLC purity >99%; MS (MALDI): 1577.203[M+H]$^+$ (FIG. 18).

Figures 19A, 19B:
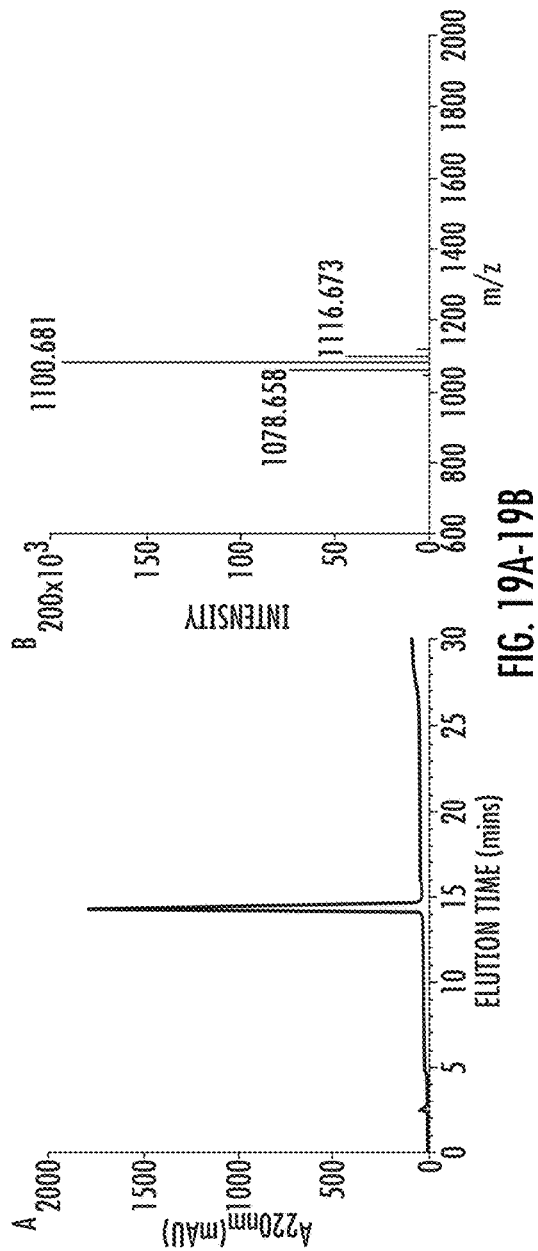
FIGS. 19A-19B shows RP-HPLC (A) and MALDI-Tof MS (B) characterization of C$_8$-Tau.

C$_8$-Tau was synthesized by automated solid-phase synthesis of Fmoc-GVQIVYKK-Rink (SEQ ID NO: 1), followed by manual coupling of 4 equivalents of octanoic acid using HBTU/DIEA in DMF. After cleavage with trifluoroacetic acid/trisopropanol/water (95:2.5:2.5), the crude product was precipitated with diethyl ether and purified by reversed phase HPLC. The product concentration was determined by UV-Vis analysis of the tyrosine absorption at 375 nm and aliquotted into cryo-vials, lyophilized and stored at −30° C. HPLC purity >99%; MS (MALDI): 1100.681 (FIG. 19).

Example 2

Synthesis and Self-Assembly of a qCPT-buSS-Sup35 DA Conjugate

To illustrate the general applicability of the present invention we synthesized an analogue of the qCPT-buSS-Tau DA using a β-sheet forming peptide sequence derived from the yeast prion Sup35, CGNNQQNYKK (SEQ ID NO 5)—qCPT-buSS-Sup35.

Upon dissolution in aqueous solution, qCPT-buSS-Sup35 was found to form the nanotube structure of similar dimensions as qCPT-buSS-Tau indicating that the replacement of one β-sheet forming peptide for another has no effect on the structure that is adopted (FIG. 3h).

Figure 20:
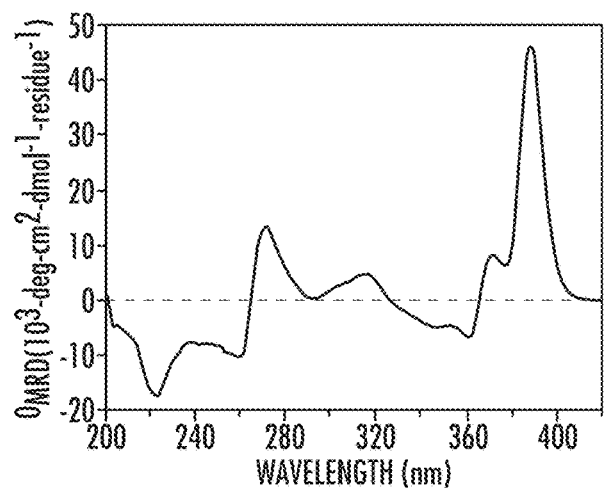
FIG. 20 is a CD spectrum of 10 μM qCPTbuSS-Sup35 in 10 mM sodium phosphate.

CD analysis of the self-assembled structure shows the same pattern of signals as qCPT-buSS-Tau (FIG. 20), implying that the internal packing of the monomers is unaffected by the change in peptide sequence.

Methods for Example 2 qCys-Sup35 was synthesized in a similar manner to qCys-Tau (as described in Example 1). Cleavage from the resin was affected by TFA/TIS/H$_2$O/EDT (90:5:2.5:2.5), and the crude peptide was purified by reversed phase HPLC.

Figure 21A:
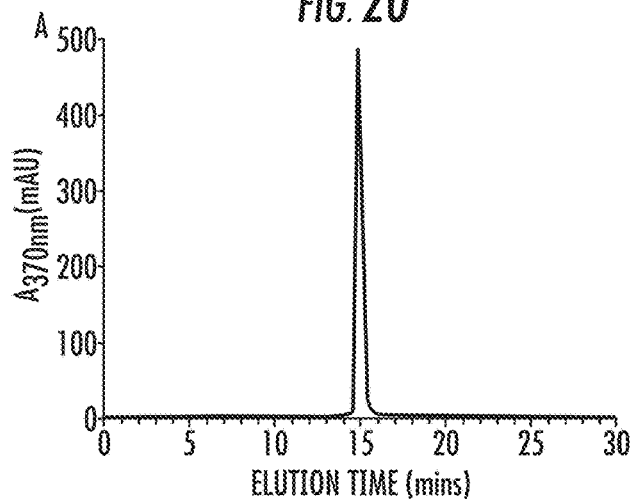
FIGS. 21A-21B is the RP-HPLC (A) and ESI MS (B) characterization of qCPT-buSS-Sup35.
Figure 21B:
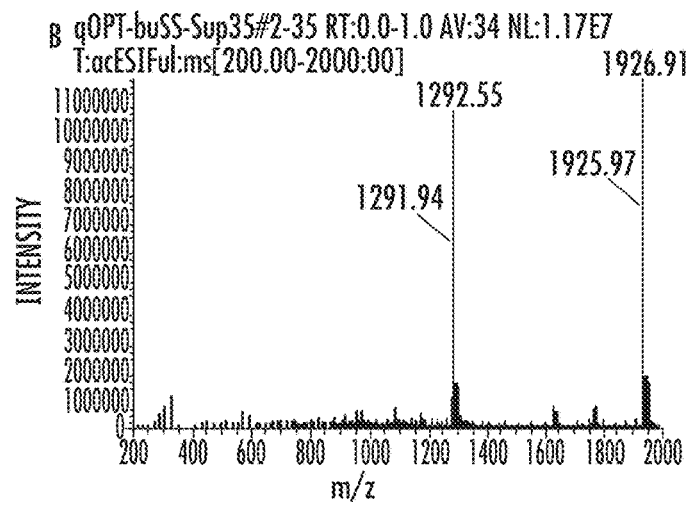

Synthesis of qCPT-buSS-Sup35. qCys-Sup35 (5.4 mg, 2.5 μmol) was dissolved in an N$_2$-purged DMSO solution of CPT-buSS-Pyr (10.5 mg in 800 μl, 18.8 μmol) and allowed to react for 5 days. The solution was diluted to 10 ml with 0.1% aqueous TFA and purified by RP-HPLC. Product fractions were combined and immediately lyophilized. The pale yellow solid obtained was dissolved in 4 ml nanopure water containing 0.1% TFA and the product concentration was determined by DTT calibration to be 340 μM (2.0 mg, 22%). The solution was then aliquotted into cryo-vials, lyophilized and stored at −30° C. HPLC purity >99%; MS (ESI): 1925.97 [M+2H]$^{2+}$, 1291.94 [M+3H]$^{3+}$ (FIG. 21).

Example 3

Figure 22:
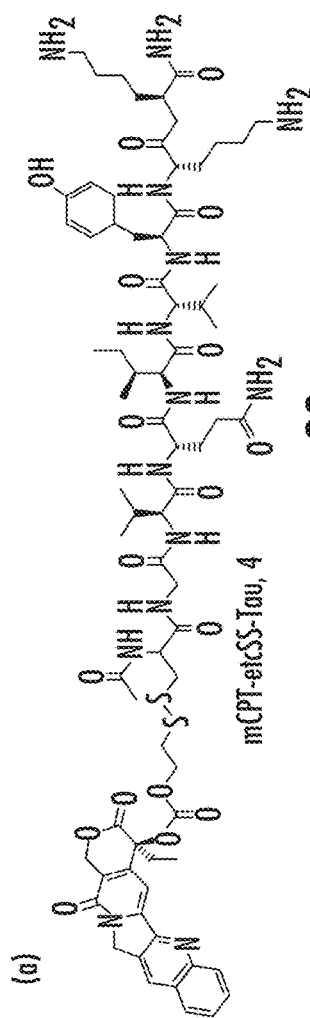
FIG. 22 illustrates the molecular structure of mCPT-etcSS-Pyr
Figure 23:
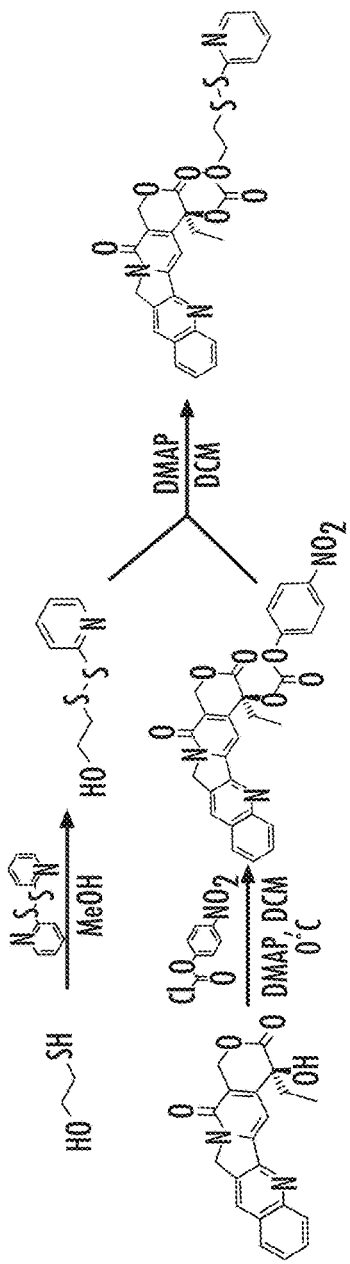
FIG. 23 depicts the synthesis of the carbonate-based linker CPT-etcSS-Pyr.
Figure 24:
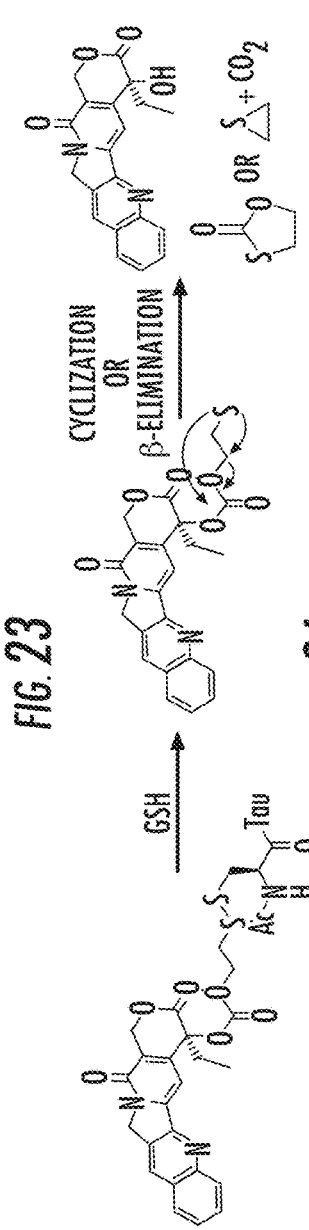
FIG. 24 shows the mechanism of the glutathione-induced release of CPT from mCPT-etcSS-Tau

Synthesis and Self-Assembly of a Disulfanylcarbonate Linked mCPT-etcSS-Tau Conjugate To illustrate the applicability of the present invention to other linking moieties, a disulfanylcarbonate linked analogue, mCPT-etcSS-Tau (FIG. 22), of mCPT-buSS-Tau was synthesized by reaction of an activated disulfide derivative of CPT—CPT-etcSS-Pyr (FIG. 23)—with the cysteine-functionalized Tau peptide, CGVQIVYKK (SEQ ID NO:1) (mCys-Tau). This carbonate-based linker can more effectively release the free CPT drug upon reduction with glutathione, compared to the disulfanylbutanoate linker (FIG. 24).

Figures 25A, 25B:
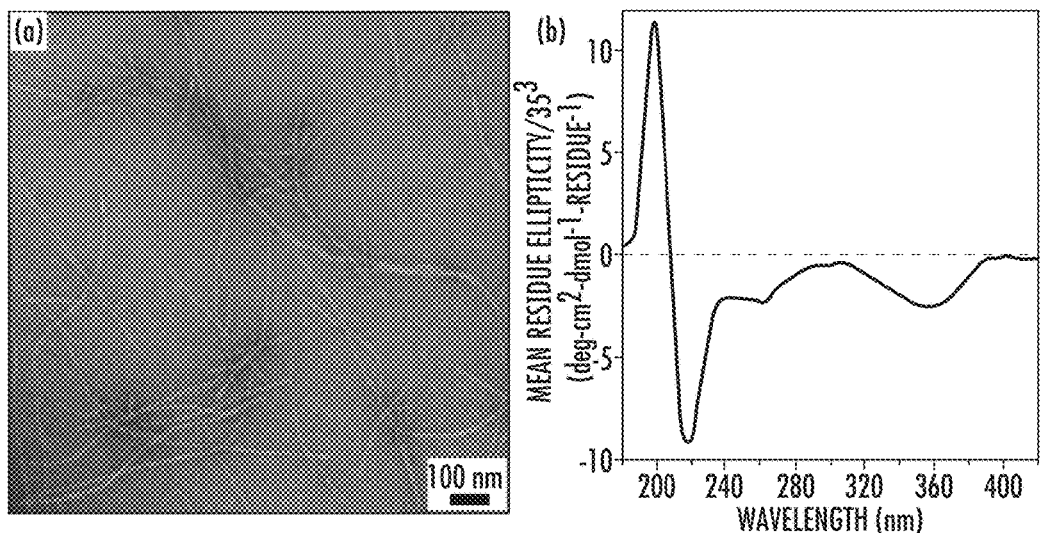
FIGS. 25A-25B shows the self-assembly characterization of mCPT-etcSS-Tau. Representative TEM image of a 100 μM aqueous solution of 4 (a), showing the filamentous nanostructures formed by this conjugate. Circular dichroism (CD) spectrum of a 100 μM aqueous solution of mCPT-etcSS-Pyr (b), indicating the β-sheet secondary structure adopted by this drug amphiphile and the presence of signals due to the CPT molecules being in a chiral environment.

The self-assembly of mCPT-etcSS-Tau into nanostructures was confirmed by dissolution of the conjugate into aqueous solution and TEM analysis after 24 hours incubation (FIG. 25a). CD analysis confirmed the presence of the expected □-sheet structure (FIG. 25b).

Degradation studies of mCPT-etcSS-Tau (50 μM) in the presence of 10 mM glutathione at 37° C. indicated the fast effective release of unmodified CPT (FIG. 26a-b) with no intermediary structures observed. In the absence of glutathione, less than 15% degradation was observed over the same 24 hour period.

Figures 26A, 26B, 26C:
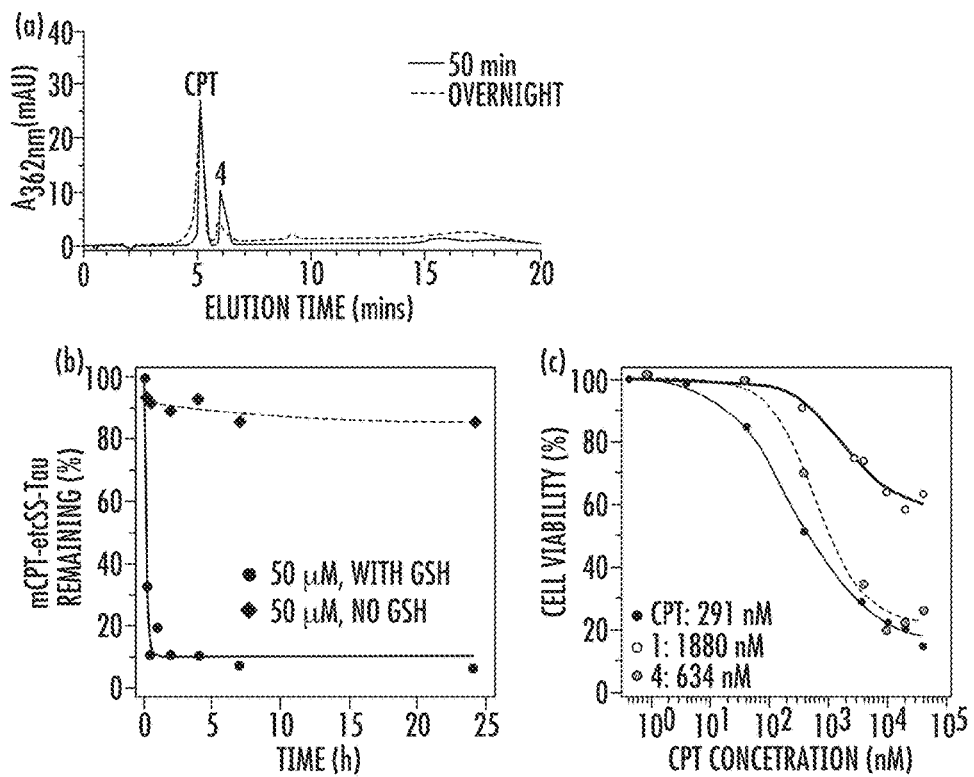
FIGS. 26A-26C depicts the HPLC chromatograms of a 50 μM solution of mCPT-etcSS-Pyr in 10 mM sodium phosphate with 10 mM GSH at room temperature after 50 min (solid trace) and overnight incubation (dotted trace) (a). The traces indicate that CPT is effectively released with little to no formation of any isolable intermediary species; kinetic study of mCPT-etcSS-Tau (50 μM) degradation in the presence and absence of 10 mM GSH (b); cytotoxicity study comparing free CPT, mCPT-buSS-Tau (1) and mCPT-etcSS-Tau (4) against the MCF-7 breast cancer cell line (c). Cell viability was determined by SRB assay and data are presented as mean±s.d. (n=3). The calculated IC50 values are given in the figure legend.

A dose-response study illustrated the effect that the more efficient drug release has on the cytotoxicity, with the carbonate-based linker having a 3-fold increase in efficacy relative to the ester-based disulfanylbutanoate linker, and exhibiting similar toxicity to free CPT (FIG. 26c).

This result demonstrates that alternative linkers can be incorporated to change the release properties of the designed DA conjugates.

Methods for Example 3

Synthesis of 2-(pyridyl-disulfanyl)ethanol. The synthesis of this precursor was adapted from a previously reported procedure for the formation of activated disulfides. 2-Aldrithiol (1.29 g, 5.86 mmol) was dissolved in MeOH (3.5 ml) and 2-mercaptoethanol (300 μl, 334 mg, 4.28 mmol) was added dropwise over 5 min, the solution turning a yellow color. After 3 h, the solution was diluted with 0.1% aq. TFA (4.5 ml) and purified by RP-HPLC. Product fractions were combined and solvents removed in vacuo. A solution of sat. NaHCO3 (15 ml) was added to neutralize the TFA, allowing to stand for 30 min before extracting into DCM. The organic extract was dried over Na2SO4 and solvents removed to give 2-(pyridyl-disulfanyl)ethanol as pale yellow oil (561 mg, 70%). $^1$H (300 MHz, CDCl$_3$, Me4Si) 2.91-2.99 (2H, m), 3.80 (2H, br s), 7.15 (1H, m), 7.41 (1H, dt, J1,3 8.0, 1.0), 7.54-7.63 (1H, m), 8.47-8.53 (1H, m).

Synthesis of Camptothecin-4-nitrophenyl carbonate. Camptothecin (100 mg, 287 μmol) and nitrophenylchloroformate (203 mg, 1.00 mmole) were dissolved/suspended in dry DCM (15 ml) at 0° C. Dimethylaminopyridine (DMAP, 210 mg, 1.72 mmoles) was added, turning the solution yellow. After 3 h, the yellow-brown solution was filtered, washed with 1 N HCl (20 ml), dried over Na$_2$SO$_4$ and concentrated in vacuo. Purification by flash chromatography—DCM (50 ml), 1:1 DCM/EtOAc (100 ml), EtOAc (200 ml), then 1% MeOH in EtOAc (100 ml)—gave camptothecin-4-nitrophenyl carbonate as a pale yellow solid (75 mg, 51%). $^1$H (400 MHz, CDCl$_3$, Me$_4$Si) 1.01-1.12 (3H, m) 2.16-2.45 (2H, m) 5.24-5.38 (2H, m) 5.42 (1H, d, J1,2 17.3) 5.72 (1H, d, J1,2 17.2) 7.36-7.44 (3H, m) 7.70 (1H, ddd, J1,3 8.2, 6.9, 1.2) 7.86 (1H, ddd, J1,3 8.5, 7.0, 1.5) 7.96 (1H, dd, J1,3 8.2, 1.3) 8.17-8.28 (3H, m), 8.43 (1H, s).

Figure 27:
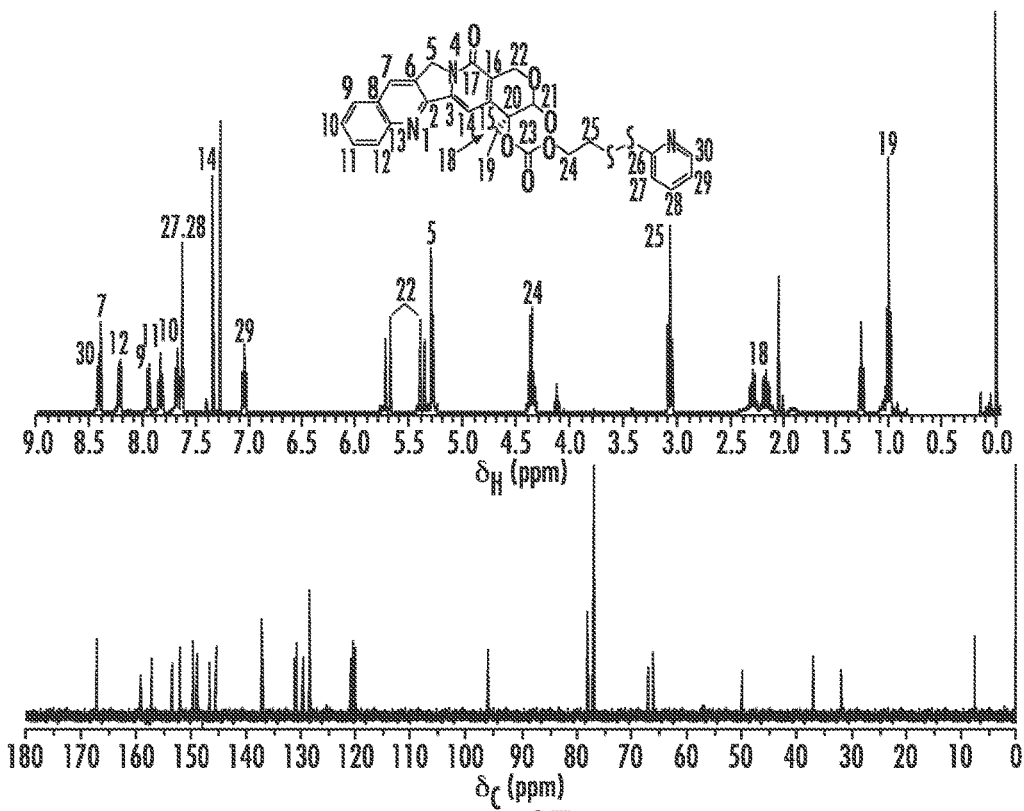
FIG. 27 depicts the (top)$^1$H NMR (400 MHz, CDCl$_3$) and (bottom)$^{13}$C NMR (100 MHz, CDCl$_3$) of CPT-etcSS-Pyr.

Synthesis of Camptothecin-(4-pyridyldisulfanyl)ethyl carbonate (CPT-etcSS-Pyr). Camptothecin-4-nitrophenyl carbonate (70 mg, 136 μmol) and 2-(pyridyl-disulfanyl) ethanol (42 mg, 225 μmol) were dissolved in dry DCM (15 ml), and DMAP (31 mg, 254 μmol) was added and the mixture was refluxed (55° C.) overnight. After cooling, the mixture was washed with 1 M NaHCO3 (3×15 ml) till colorless, dried over Na2SO4 and concentrated in vacuo. Purification by flash chromatography-DCM (50 ml), 1:1 DCM/EtOAc (300 ml), 1:3 DCM/EtOAc (100 ml), EtOAc (200 ml), 1% MeOH in EtOAc (100 ml), then 2% MeOH in EtOAc (100 ml)—to give CPT-etcSS-Pyr as a pale yellow solid (57 mg, 75%). $\delta_H$ (400 MHz, CDCl3, Me4Si) 1.01 (3H, t, J1,3 7.5), 2.10-2.21 (1H, m), 2.24-2.34 (1H, m), 3.06 (2H, t, J1,3 6.6), 4.30-4.42 (2H, m), 5.27-5.30 (2H, m), 5.39 (1H, d, J1,2 17.2), 5.69 (1H, d, J1,2 17.2), 7.03 (1H, td, J1,3 5.0, 3.4), 7.34 (1H, s), 7.62 (1H, d, J1,3 1.4), 7.63-7.64 (1H, m), 7.65-7.70 (1H, m), 7.83 (1H, m), 7.94 (1H, dd, J1,3 8.2, 1.3), 8.22 (1H, d, J1,3 8.7), 8.39 (1H, s), 8.42 (1H, dt, J1,3 4.8, 1.4); $^{13}$C (100 MHz, CDCl3, Me4Si) 7.6, 31.9, 36.9, 50.0, 66.4, 67.1, 78.0, 96.0, 119.9, 120.3, 120.9, 128.1, 128.2, 128.4, 129.7, 130.7, 131.2, 137.2, 145.5, 146.5, 148.9, 149.7, 152.3, 153.4, 157.3, 159.3, 167.3 (FIG. 27).

Figure 28:
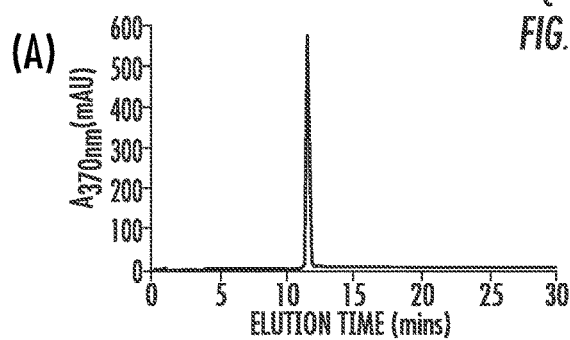
FIGS. 28A-28B depicts the RP-HPLC (a) and MALDI-Tof MS (b) characterization of 4. In-source fragmentation was observed corresponding to the loss of one CPT-O—C (=O)— moiety (indicated by *).
Figure 28:
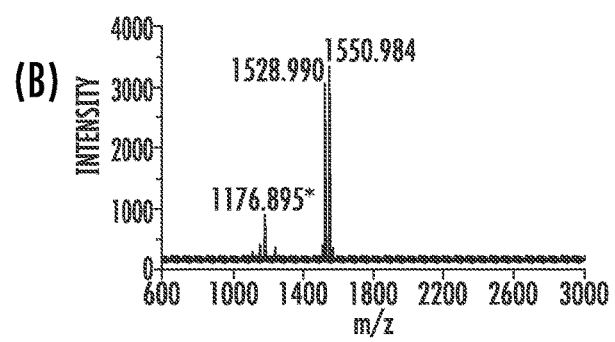

Synthesis of mCPT-etcSS-Pyr. mCys-Tau (22.8 mg, 21.2 μmol) was dissolved in an N$_2$-purged DMSO solution of CPT-etcSS-Pyr (15.4 mg, 27.5 μmol) and allowed to react overnight. The solution was diluted to 9 ml with 0.1% aqueous TFA and purified by RP-HPLC. Product fractions were combined and immediately lyophilized. The pale yellow solid obtained was dissolved in 1:1 H2O/MeCN (10 ml) and the product concentration determined by DTT calibration (S1.4) to be 1.61 mM (24.6 mg, 76%). The solution was aliquotted into cryo-vials, lyophilized and stored at −30° C.; HPLC purity >99%; MS (MALDI): 1528.990 (FIG. 28).

Example 4

Self-Assembly and Characterization of a PXL-buSS-Tau DA Conjugate

Figure 29:
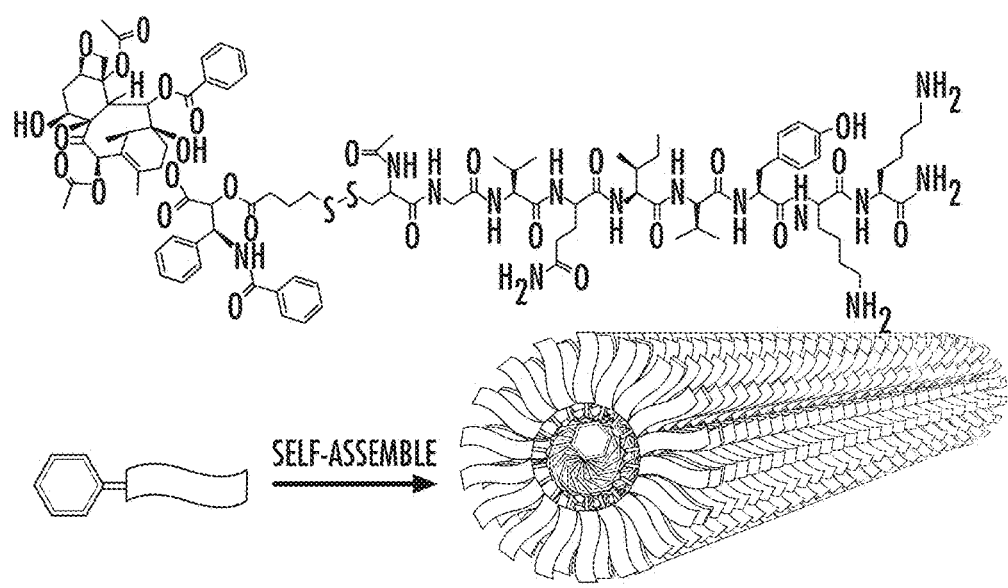
FIG. 29 is a schematic illustration of the structure of PXL-buSS-Tau and the nanofiber conformation it takes in aqueous solutions.

To illustrate the applicability of the present invention to other hydrophobic drugs, the paclitaxel analogue, PXL-buSS-Tau, of mCPT-buSS-Tau was synthesized by reaction of an activated-disulfide derivative of PXL—PXL-buSSPyr—with the cysteine-functionalized Tau peptide, CGVQIVYKK (SEQ ID NO: 6) (mCys-Tau) (FIG. 29). The activated disulfide buSSPyr linker was conjugated to PXL via the 2'-hydroxyl group. It is known that modification of the C'2 hydroxyl position in PXL can lead to loss of activity, so addition of the disulfide linker to this position effectively creates a paclitaxel prodrug which can only exert its effect when taken into tumor cells and when the drug is released from the linker by glutathione.

Figures 30A, 30B, 30C, 30D:
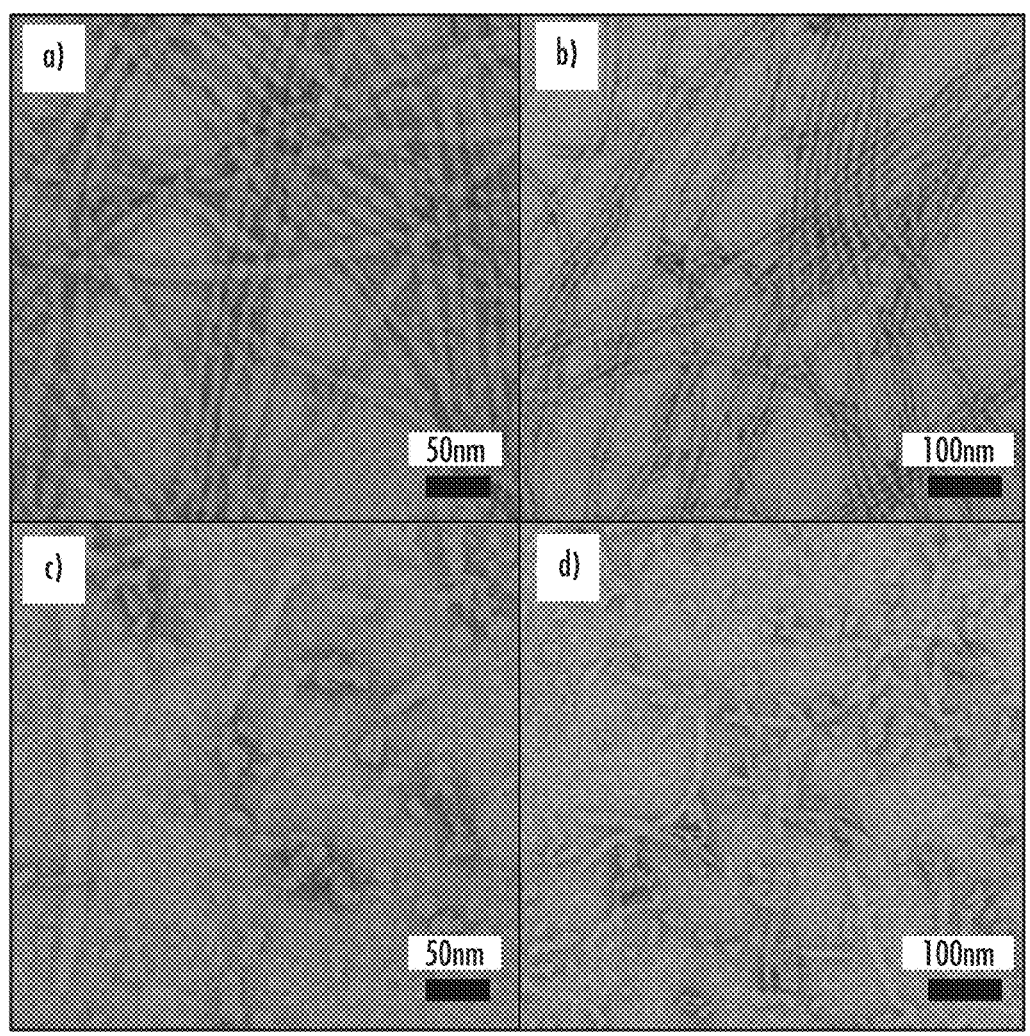
FIGS. 30A-30D shows TEM images of PXL-buSS-Tau.

The self-assembly of PXL-buSS-Tau into nanostructures was confirmed by dissolution of the conjugate into aqueous solution and TEM analysis after 48 hours incubation. At 200 μM, PXL-buSS-Tau clearly form nanofibrous structures with diameters of 10-20 nm (FIG. 30), whilst at 10 μM smaller fibers and spherical micellar structures are observed, suggestive of a higher CMC value when compared to the analogous CPT conjugate.

The CMC value of PXL-buSS-Tau was determined by encapsulation of the solvatochromic dye Nile Red into the hydrophobic interior of the nanofiber structures. Fluorescence measurements of this fluorophore gave a CMC value in the range of 10 to 50 μM (FIG. 31a).

Figures 31A, 31B, 31C:
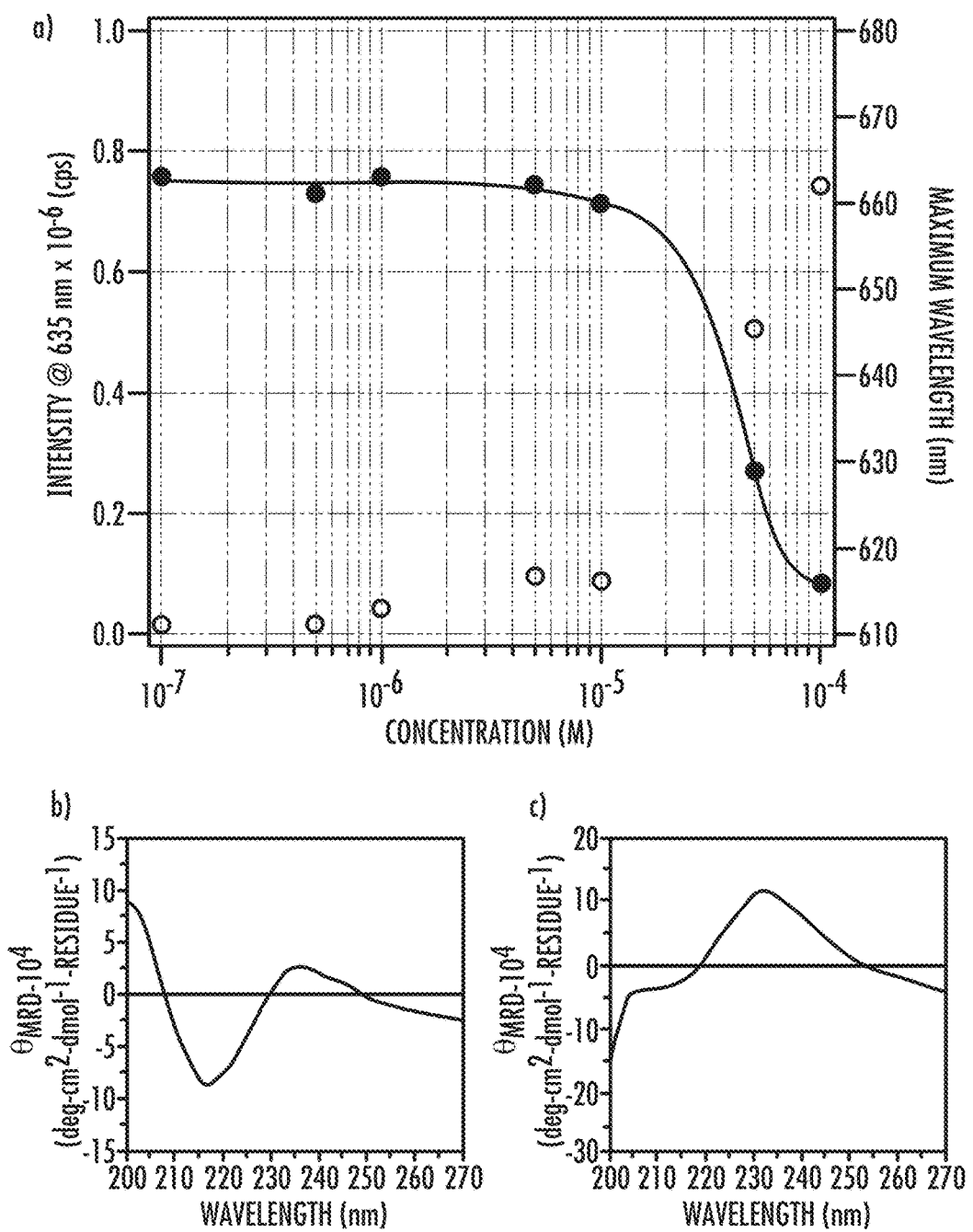
FIGS. 31A-31C shows the CMC value and CD spectrum of PXL-buSS-Tau.

In order to demonstrate different secondary structures at various concentrations below and above CMC value, circular dichroism spectra were recorded at 5 μM and 100 μM (FIGS. 31b and 31c). At concentrations lower below the CMC, PXL-buSS-Tau formed beta sheet secondary structures (negative absorption at 216 nm), with a positive absorption at 237 nm that may arise from the n-π* transition of the PXL carbonyl groups at 3C' and 9C. At higher concentrations, single molecules aggregate to cylindrical nanofibers with paclitaxel packed inside as hydrophobic core, leading to a significantly stronger signal at 237 nm.

Figure 32:
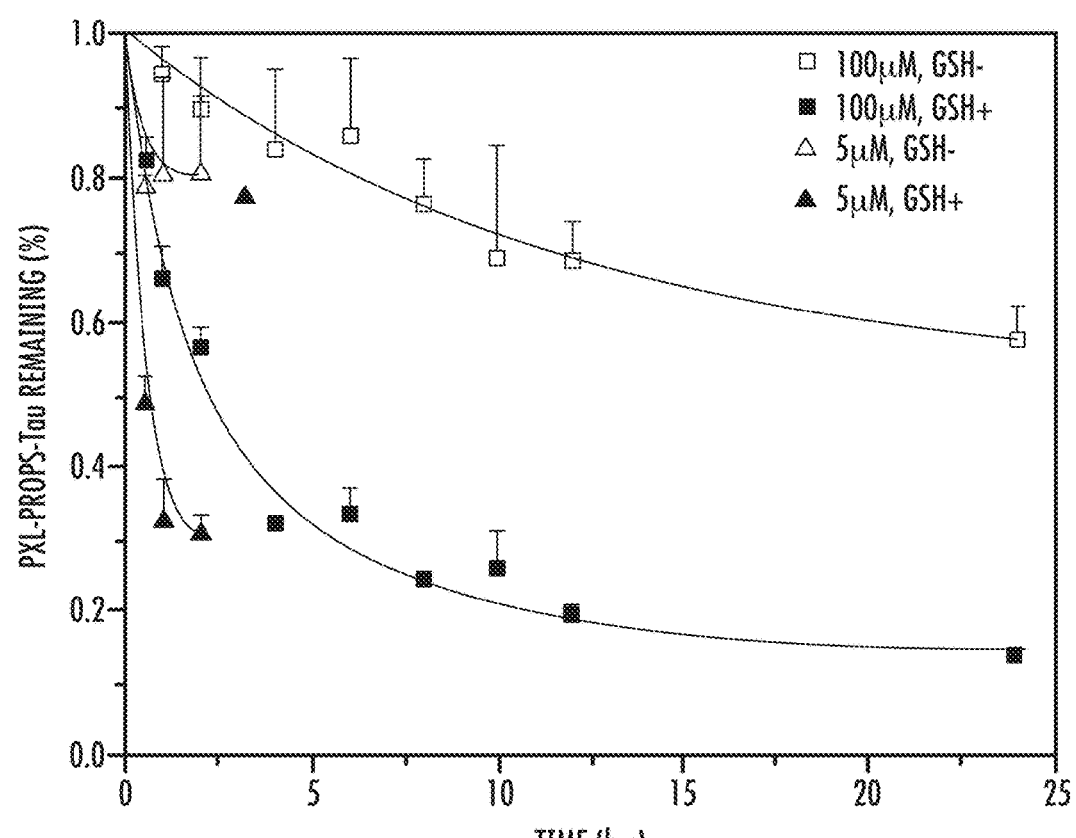
FIG. 32 depicts the PXL-buSS-Tau release curve in PBS buffer under 37° C.

PXL release studies were carried out at 100 μM and 5 μM concentrations in PBS buffer at 37° C. (FIG. 32). Significant release of paclitaxel was observed for the 100 μM solution after 30 minutes in the presence of glutathione, with the lower concentration of 5 µM showing a much faster release than that of 100 µM—consistent with the DA conjugate existing as a greater proportion of monomers at this concentration below the CMC. After 2 hrs, around 70% of the PXL-buSS-Tau was cleaved by glutathione at 5 µM while only 40% paclitaxel was released at 100 µM, again illustrating the protective effect that self-assembly into nanostructures has upon the biodegradable linker.

Figures 33A, 33B, 33C:
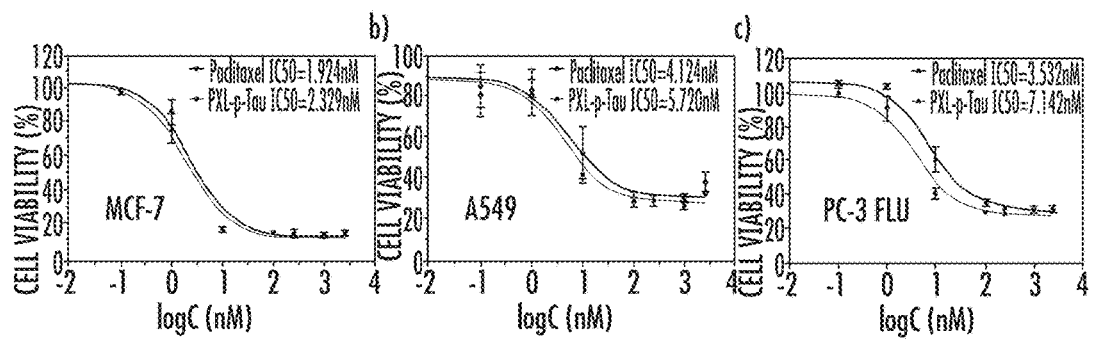
FIGS. 33A-33C shows an in vitro dose-response relationship study of PXL-buSS-Tau against human MCF-7 breast cancer (a) human A549 non-small cell lung cancer (b) and human PC-3 FLU prostate cancer (c) cells. All cancer cells were incubated with the appropriate DA molecules for 48 hours and cell viability was determined by SRB assay. Cytotoxicity experiments were performed in triplicate and values are given as mean±s.d. (n=3).

To evaluate anti-tumor efficacy, the cytotoxicity of PXL-buSS-Tau towards human breast cancer MCF-7, non-small cell lung cancer A549, and human prostate cancer PC-3 FLU cell lines was determined (FIG. 33). PXL-buSS-Tau exhibited a strong cytotoxic effect on all three cancer cell lines, exhibiting similar efficacy to free paclitaxel. In addition, the cellular morphologies were observed to change, displaying a larger size that is consistent with G2-M arrest during the cell cycle.

Methods for Example 4

Figure 34:
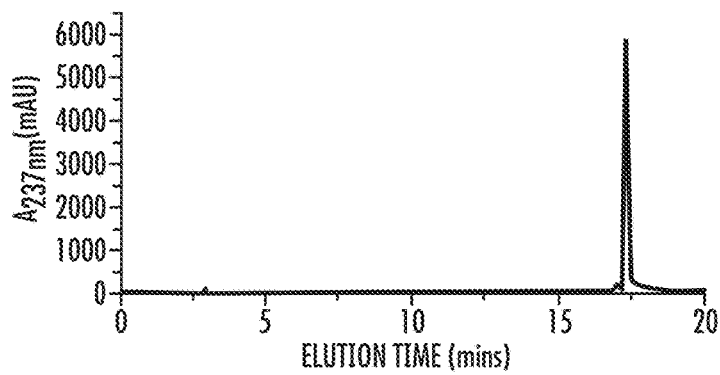
FIG. 34 is an RP-HPLC analysis of PXL-buSS-Pyr.
Figure 35:
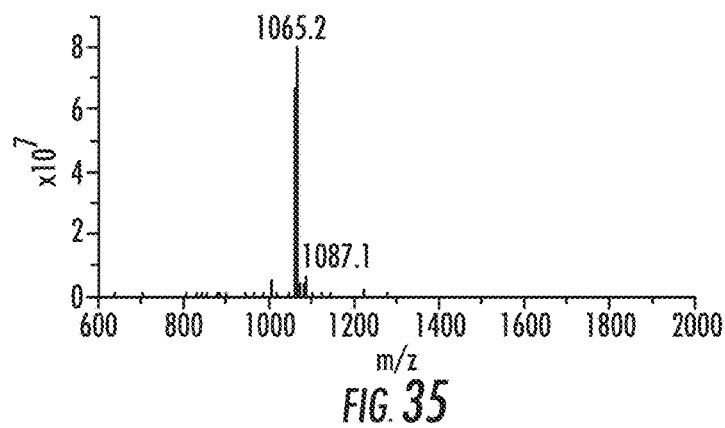
FIG. 35 is an ESI-MS characterization of PXL-buSS-Pyr.

Synthesis of PXL-buSS-Pyr (C2' isomer). Paclitaxel (185.6 mg, 0.22 mmol), 4-(pyridin-2-yl-disulfanyl)butyric acid (100 mg, 0.44 mmol), DIC (68.36 µL, 0.44 mol), DMAP (26.7 mg, 0.22 mmol) were added to an oven dried flask under nitrogen and dissolved in anhydrous acetonitrile (12.7 ml). The reaction was allowed to stir in the dark at room temperature for 48 hours. The solvents were removed in vacuo and the residue was dissolved in chloroform and purified by flash chromatography (3:2 EtOAc/hexanes), to give PXL-buSS-Pyr (0.108 g, 46.7%). HPLC purity >98% (FIG. 34); MS (ESI): m/z 1065.2 for $[M+H]^+$ (FIG. 35).

Figure 36:
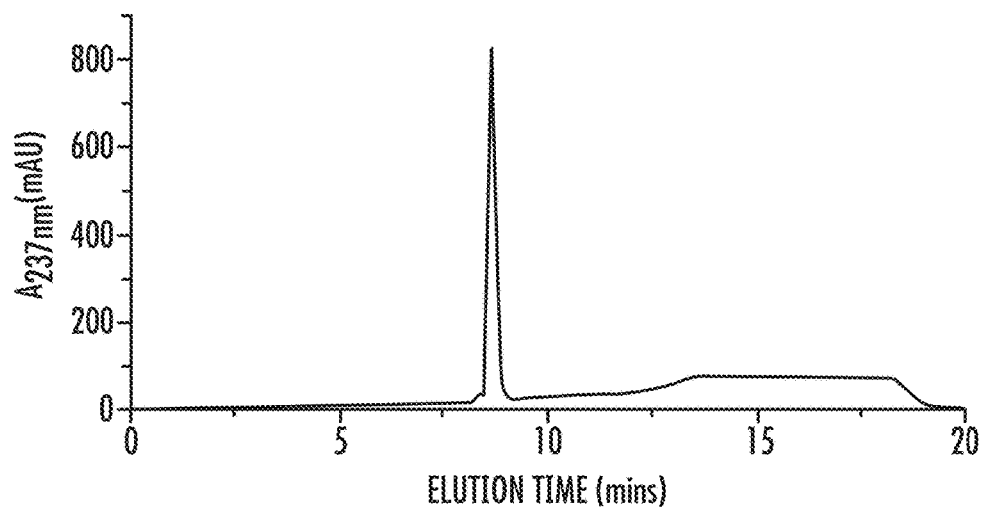
FIG. 36 shows the RP-HPLC analysis of PXL-buSS-Tau.
Figure 37:
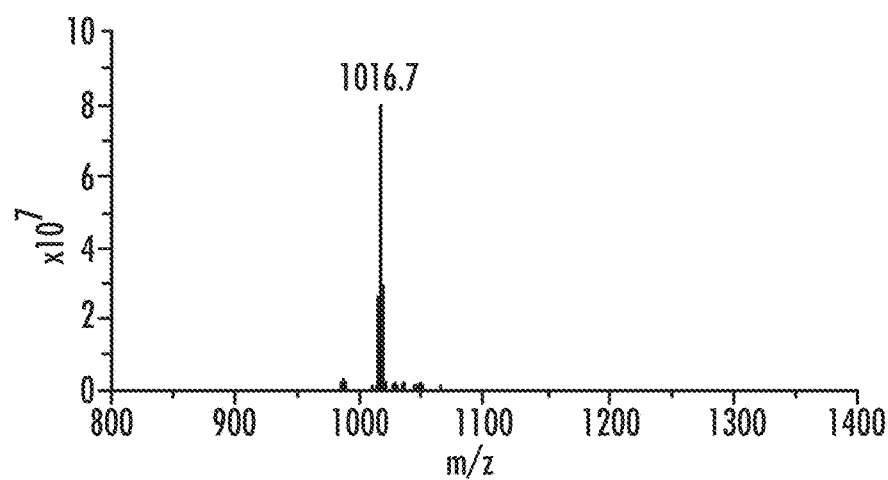
FIG. 37 is an ESI-MS characterization of PXL-buSS-Tau.

Synthesis of PXL-buSS-Tau. Add AcCGVQIVYKK (SEQ ID NO: 6) (27.7 mg, 25.7 µmol) and PXL-buSS-Pyr (54.7 mg, 51.4 µmol) into an oven dried flask under nitrogen and dissolved in anhydrous dimethylformamide (5 ml). The reaction was allowed to stir for 16 hr after which the solution was purified by reversed phase HPLC (30% to 95% acetonitrile in water with 0.1% TFA over 45 minutes). Product-containing fractions were combined and lyophilized to give PXL-buSS-Tau as a white powder (31.3 mg, 60%). HPLC purity >98% (FIG. 36); MS (ESI) 1031 $[M+2H]^{2+}$ (FIG. 37).

Example 5

Self-Assembly and Characterization of a Dual Drug DA Conjugate

Incorporating two different drug molecules into a single self-assembling entity presents a challenge when the overall properties of the conjugate are expected to depend strongly on the nature of those drugs. For simplicity, we used the reducible disulfylbutyrate linker to conjugate both drugs to the hydrophilic peptide. However, in other embodiments, one can use linkers that would allow attachment via orthogonal reaction mechanisms. Such an approach opens up the ability of differential drug release through separate degradation pathways. The β-sheet forming peptide was chosen to be a sequence derived from the Sup35 yeast prion, GNNQQNYKK (SEQ ID NO: 7), with the two added lysine residues providing a charged head group and the glycine acting as a spacer. This sequence is more hydrophilic than the Tau sequence we have previously utilized, and is expected to provide greater solubility to the final conjugate, CPT-PXL-Sup35. Conjugation of the two drugs is accomplished using directed disulfide formation, requiring the incorporation of two thiol-containing cysteine residues into the peptide. The total drug loading of this conjugate is fixed at 41%, with a CPT and PXL content of 12 and 29%, respectively.

Figure 38:
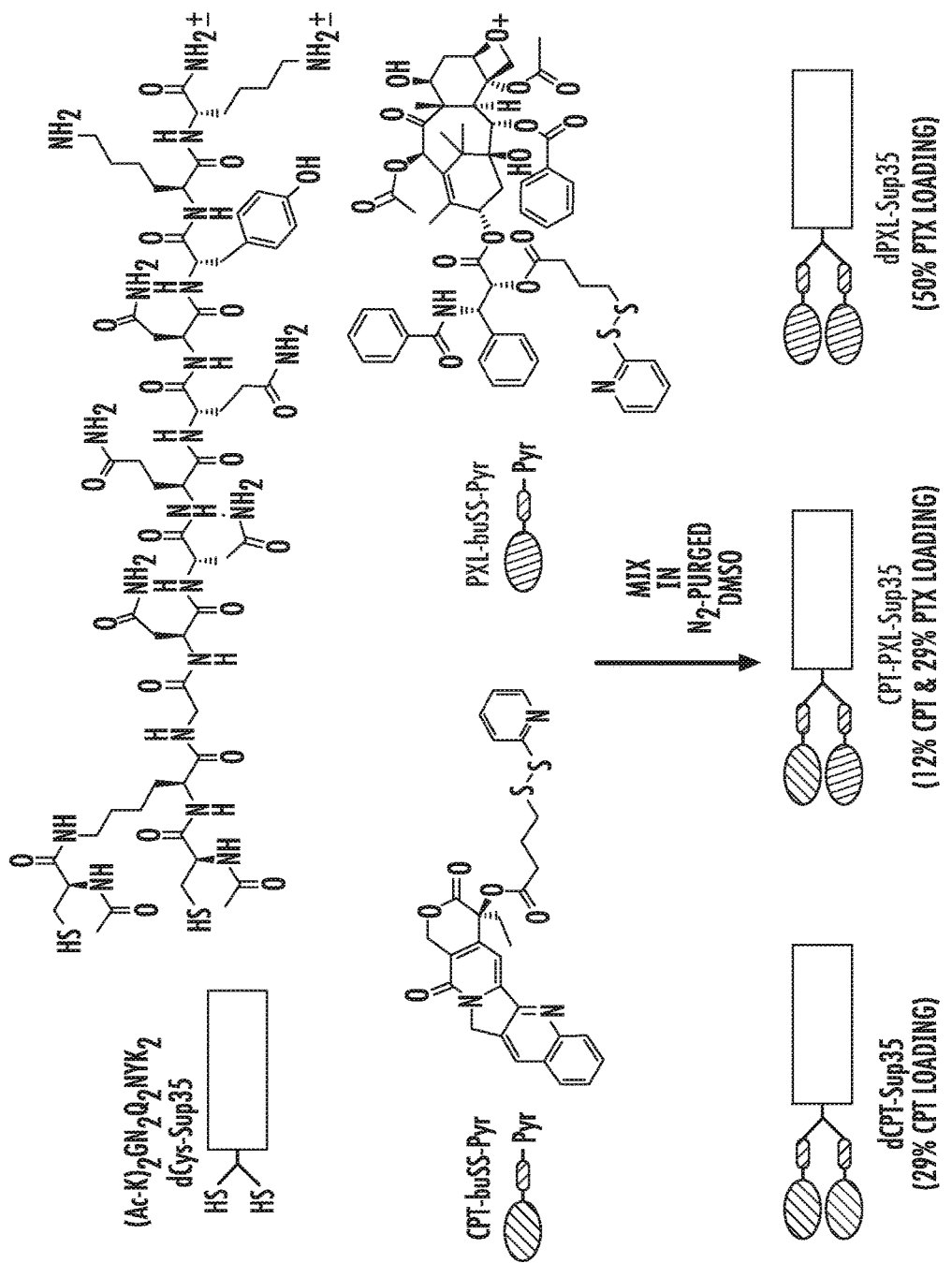
FIG. 38 depicts the synthesis of a hetero-dual drug amphiphile (DA) embodiment, CPT-PXL-Sup35, and homo-dual DAs, dCPT-Sup35 and dPXL-Sup35, from the reaction of dCys-Sup35 with a 1:1 mixture of activated disulfide drugs, CPT-buSS-Pyr and PXL-buSSPyr.
Figures 39A, 39B:
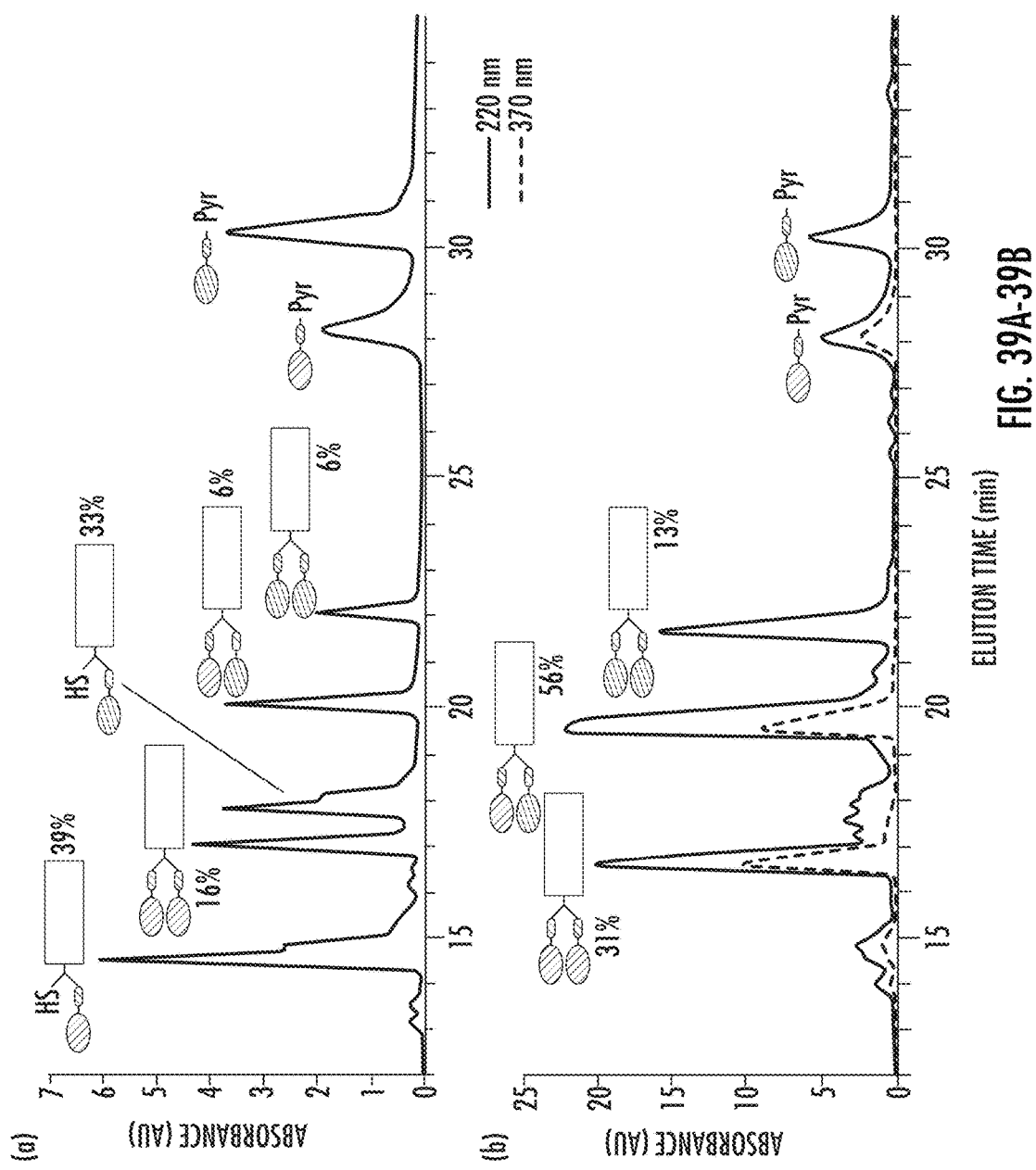
FIGS. 39A-39B shows the reversed-phase HPLC analysis during the synthesis of a dual drug amphiphile embodiment. Preparative HPLC chromatograms of the reaction of dCys-Sup35 with (39 a) 1 equivalent of a 1:1 mixture of CPT-buSS-Pyr and PXL-buSS-Pyr after overnight reaction and (39 b) 3 equivalents of a 1:1 mixture of CPT-buSS-Pyr and PXL-buSS-Pyr after 5 days reaction. Percentages give the relative amounts of each species formed, as determined by calibration of the isolated conjugates. The 220 nm traces (dark) show absorptions from both CPT and PXL, whereas the 370 nm trace (light) shows CPT absorptions only.

The dual DA, CPT-PXL-Sup35, was synthesized by statistical reaction with a 1:1 mixture of the activated disulfide drugs, CPT-buSS-Pyr and PXL-buSS-Pyr, in nitrogen purged DMSO (FIG. 38). Given the significant difference in structure between the two drugs, CPT being predominantly planar, and PXL being bulky and three-dimensional, it was expected that there would be a subsequent difference in the product distribution, particularly with regard to the addition of the second drug. To probe this, dCys-Sup35 was reacted with one equivalent per thiol of the 1:1 drug mixture, purifying the reaction by reversed-phase HPLC before it had reached completion (FIG. 39 a). The resulting drug-containing species were isolated and calibrated in order to determine the absolute amounts of each conjugate formed. It was found that the singly reacted species, CPT-Cys-Sup35 and PXL-Cys-Sup35, were formed in similar proportions (39 and 33% respectively), with each giving the two expected positional isomers, as indicated by the occurrence of two closely separated peaks for each species. These species were found to have reactive thiol groups, which upon dissolution in PBS were observed to form scrambled products through disulfide exchange (data not shown). The remaining products of the reaction were found to be the hetero-dual DA, CPT-PXL-Sup35, and the two homo-dual DAs, dCPT-Sup35 and dPXL-Sup35. The product distribution was observed to be biased towards the less sterically crowded dCPT-Sup35, with only 6% each of the two PXL-containing conjugates. Reaction of PXL-Cys-Sup35 with either of the two activated drugs may be hindered due to the bulky nature of PXL, potentially causing similar issues for the reaction of CPT-Cys-Sup35 with PXL-buSS-Pyr. In order to push the reaction towards completion, dCys-Sup35 was allowed to react with a three-fold excess per thiol of the 1:1 activated drug mixture for 5 days (FIG. 39 b). The final product distribution showed that the desired hetero-dual DA comprised 56% of the mixture, with dCPT-Sup35 (31%) and dPXL-Sup35 (13%) making up the remainder. The low conversion to dPXL-Sup35 again clearly indicates that the bulky PXL causes steric hindrance during the directed disulfide exchange reaction.

Figures 40A, 40B, 40C, 40D:
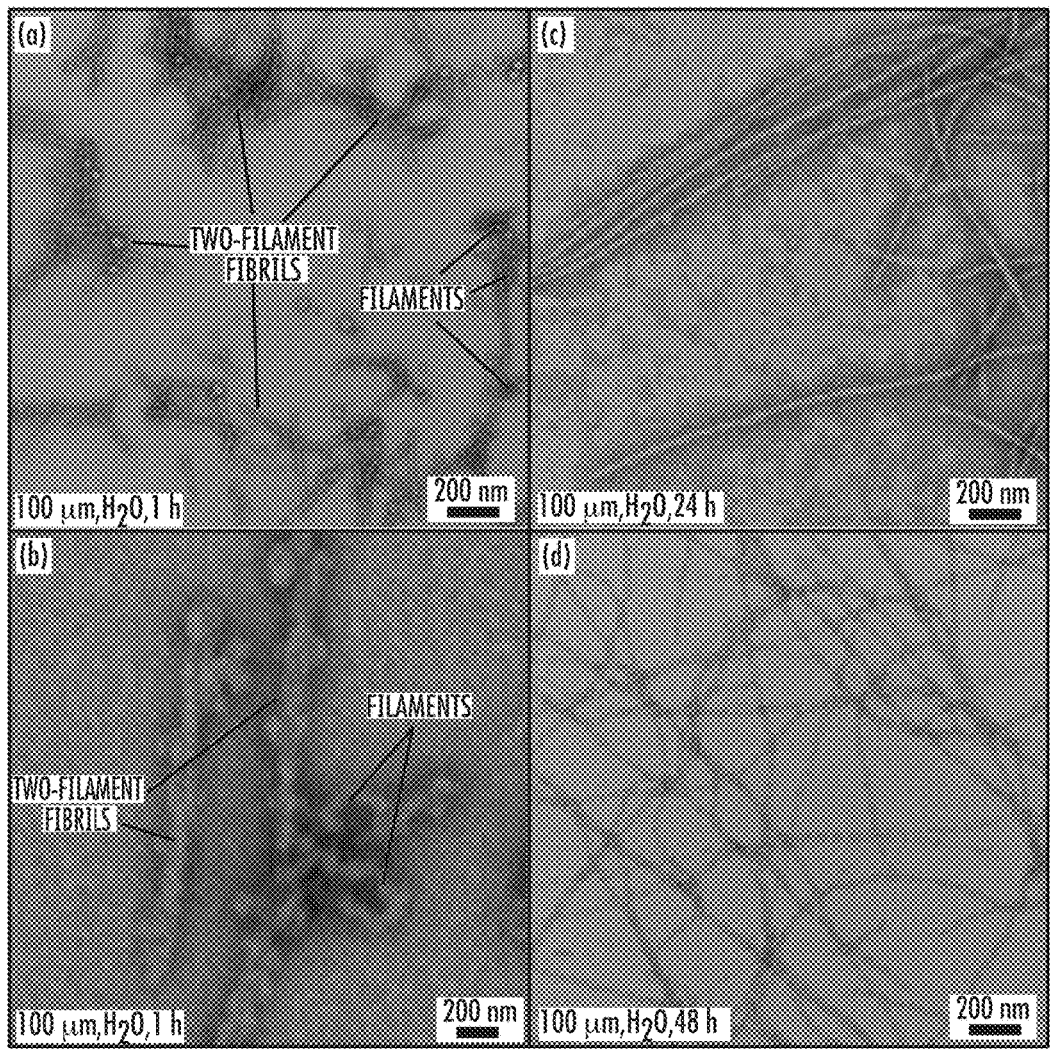
FIGS. 40A-40F is a self-assembly study of CPT-PXL-Sup35. Representative transmission electron microscopy (TEM) images of a 100 μM solution of CPT-PXL-Sup35 in water 1 hour (40 a and b), 24 hours (40 c) and 48 hours (40 d) after dilution of a 1 mM stock solution that had been allowed to age for 2 hours. Cryo-TEM image of a 500 μM solution of CPT-PXL-Sup35, diluted from a 1 mM sample that had been aged for several days prior to sample preparation (40 e). Circular dichroism (CD) spectra of the 100 μM solution in water that was monitored over 3 days, showing the formation of the β-sheet secondary structure after 24 hours of incubation (40 f). TEM samples were negatively stained with 2 wt % uranyl acetate.
Figures 40E, 40F:
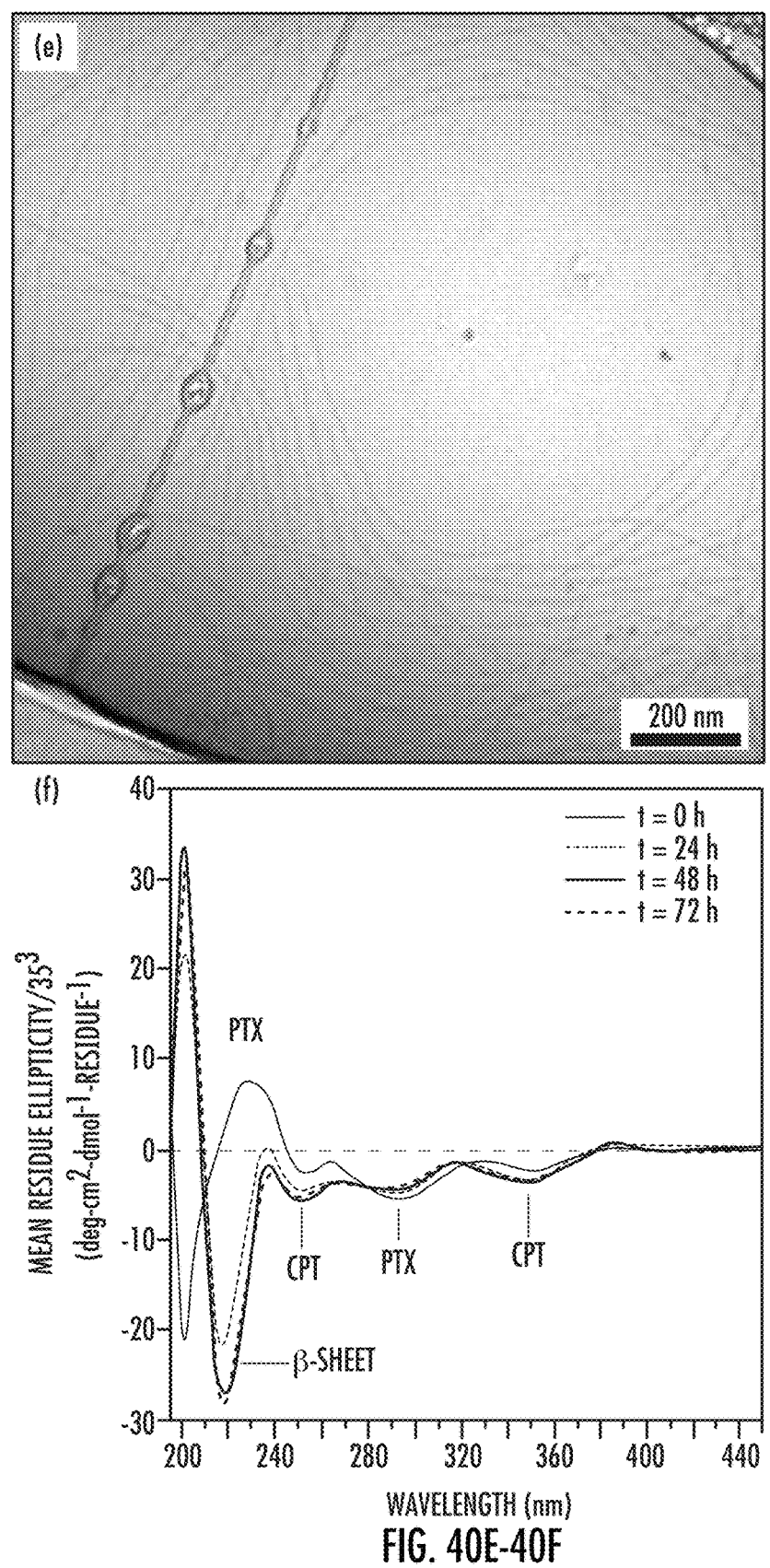

Self-Assembly Characterization. Given that the bulky nature of PXL strongly influenced the product distribution during synthesis, we investigated the effect it could have on the self-assembly of the dual DAs under aqueous conditions. Solutions of all three dual DAs were prepared at 1 mM in water and allowed to age for 2 hours before diluting to 100 µM. Transmission electron microscopy (TEM) imaging and circular dichroism (CD) spectra were recorded to evaluate the nanostructures formed and how they evolved over time (FIG. 33). Initially, the hetero-dual DA, CPT-PXL-Sup35, was observed to form two types of filamentous nanostructures—small wormlike structures (7-8 nm widths), which display a strong tendency to curl up on themselves, and comparatively longer twisted filaments ~14 nm in width (FIGS. 40 a-b). If any β-sheet secondary structure is present, the CD analysis (FIG. 40 f) indicates it is not predominant and is overwhelmed by the broad positive signal at 230 nm that can be attributed to PXL n-π* transitions. The strong negative signal at 201 nm suggests that the peptide may be adopting either a random coil or poly-proline type-II-like structure. Negative signals can also be observed for both PXL and CPT π-π* transitions, though PXL generally exhibits strong circular dichroism due to its three benzyl groups all being attached to asymmetric centers. CPT on the other hand, exhibits stronger CD when in an aggregated state, so the observation of a negative signal confirms that some degree of assembly is taking place.

After 24 hours or longer incubation time, TEM imaging shows that the twisted filament morphology is the only nanostructure present and appears to have undergone significant growth to give contour lengths on the order of several µm (FIGS. 40 c-d). CD analysis indicates that the elongation is coincident with β-sheet formation, exhibiting the typical signal at 218 nm. The negative signals for the PXL and CPT π-π* transitions also undergo a blue-shift, suggesting a change in their surrounding environment. At the widest point, these fibrils are 13.9±1.7 nm across, and at their narrowest appear to be approximately half of this value. These observations are thus suggestive of two entwined filaments, each of which is approximately 7 nm in width. Further aging does not appear to lead to any significant changes in the nanostructure, as indicated by TEM and CD analysis. Cryo-TEM imaging, a technique that preserves the solution state structure in vitreous ice, confirms that long fibrous structures are obtained (FIG. 40 e). Due to practical limitations, however, the capture of high magnification images was not possible and consequently the twisted nature could not be verified using this technique.

The presence and morphologies of the two types of nanostructure in the initial stages bears remarkable similarity to the formation of amyloid fibrils and filaments formed by peptidomimetics. It has been proposed that amyloid fibrils rich in β-sheets assemble via a series of intermediate structures, beginning with narrow filaments that can twist around one another to give fibrils comprised of two or more filaments or undergo lateral associations to give a non-twisted ribbon-like assembly. Further changes can then occur to give twisted ribbons and tubes. In the present invention, we observe the initial formation of short filaments that associate with one another to give two-filament fibrils. It is thought that the short filaments are kinetically-favorable structures that result from the rapid hydrophobic collapse of CPT-PXL-Sup35 molecules upon dissolution in water. The absence of the characteristic β-sheet absorption in the CD spectrum at early assembly stages indicates the elongation may not be directly linked to hydrogen bonding among Sup35 peptides, but rather as a result of molecular pacing associated with the hydrophobic segments. It is very likely that a β-sheet is sterically hindered due to the mismatch in size between CPT and PXL. Given time, however, it appears that two of these filaments come together and by entwining can undergo reorganization of their internal structure, forming β-sheets that promote elongation of the fibrils to give the extended structures observed at later time points. Furthermore, a small bisignate peak centered at 378 nm (one of the CPT π-π* transitions) in the CD spectrum hints at some potential CPT-CPT electronic interactions that may also play a role in the assembly process. Also, it is important to point out that, unlike the structural polymorphism shown by amyloid fibrils, the data show that the two-filament fibrils are the end-point in the structural evolution, as no ribbon-like or other structures could be seen at any time point. It is thought that this may be a combination of the hydrophobic domain of CPT-PXL-Sup35 being shielded from the aqueous environment (the amphiphilic nature of the designed Das of the present invention) and the fibril's twisted nature, with both properties preventing any further lateral associations that would give a ribbon-like morphology.

Figures 41A, 41B, 41C:
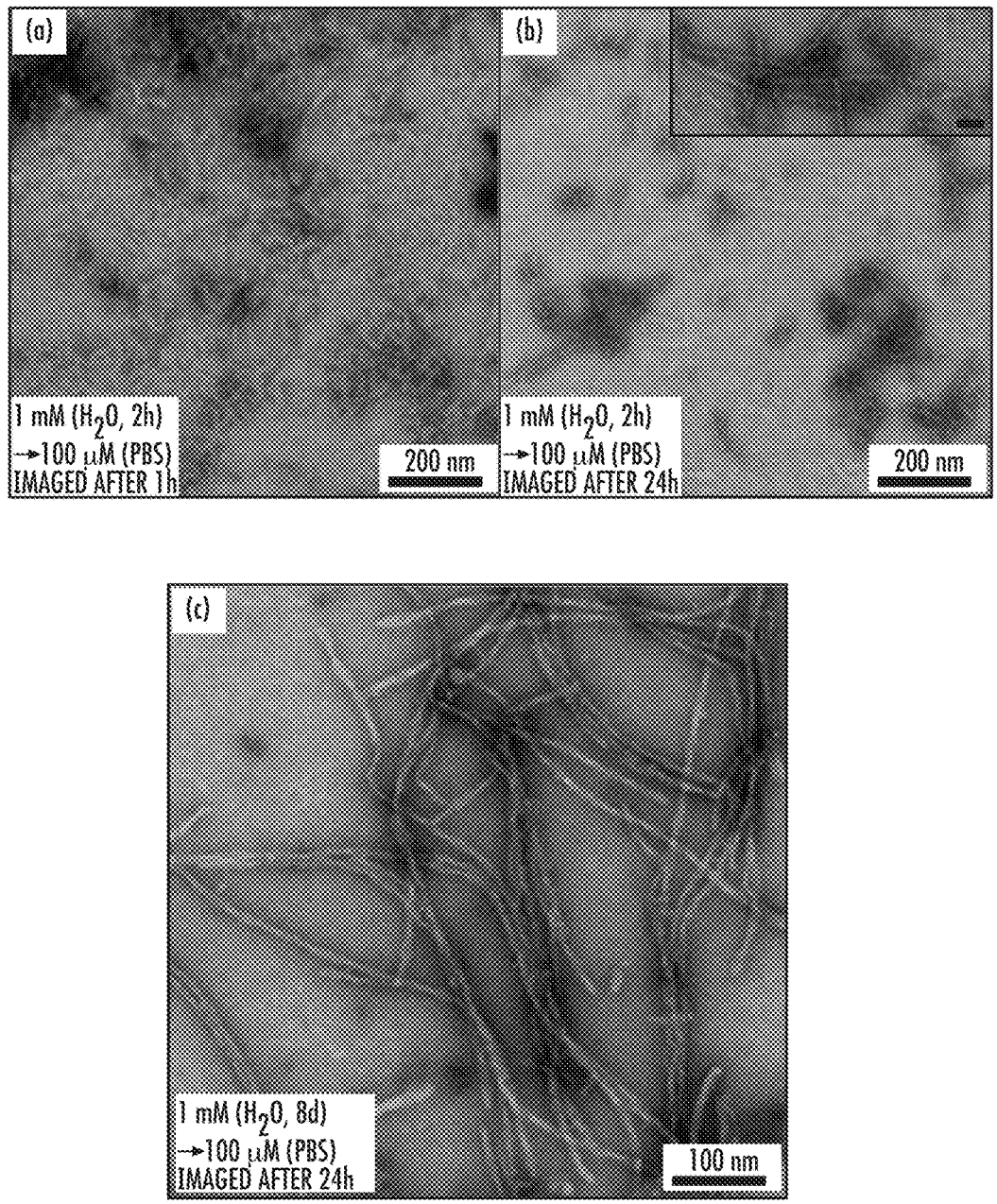
FIGS. 41A-41C shows a series of TEM images showing the effect of dilution into phosphate-buffered saline (PBS) on the self-assembly of CPT-PXL-Sup35. Dilution of a 1 mM CPT-PXL-Sup35 solution in H$_2$O after 2 hours aging to give a 100 μM solution in PBS was found to significantly slow the formation of the twisted fibril morphology, essentially capturing the filament structures (41 a). After 24 hours, little change was seen though twisted fibrils could be observed on occasion (41 b). In contrast, similar dilution of a 1 mM CPT-PXL-Sup35 solution that had been allowed to age for 8 days gave only the twisted fibril structure, indicating that PBS does not affect the existing nanostructures (41 c).
Figures 42A, 42B:
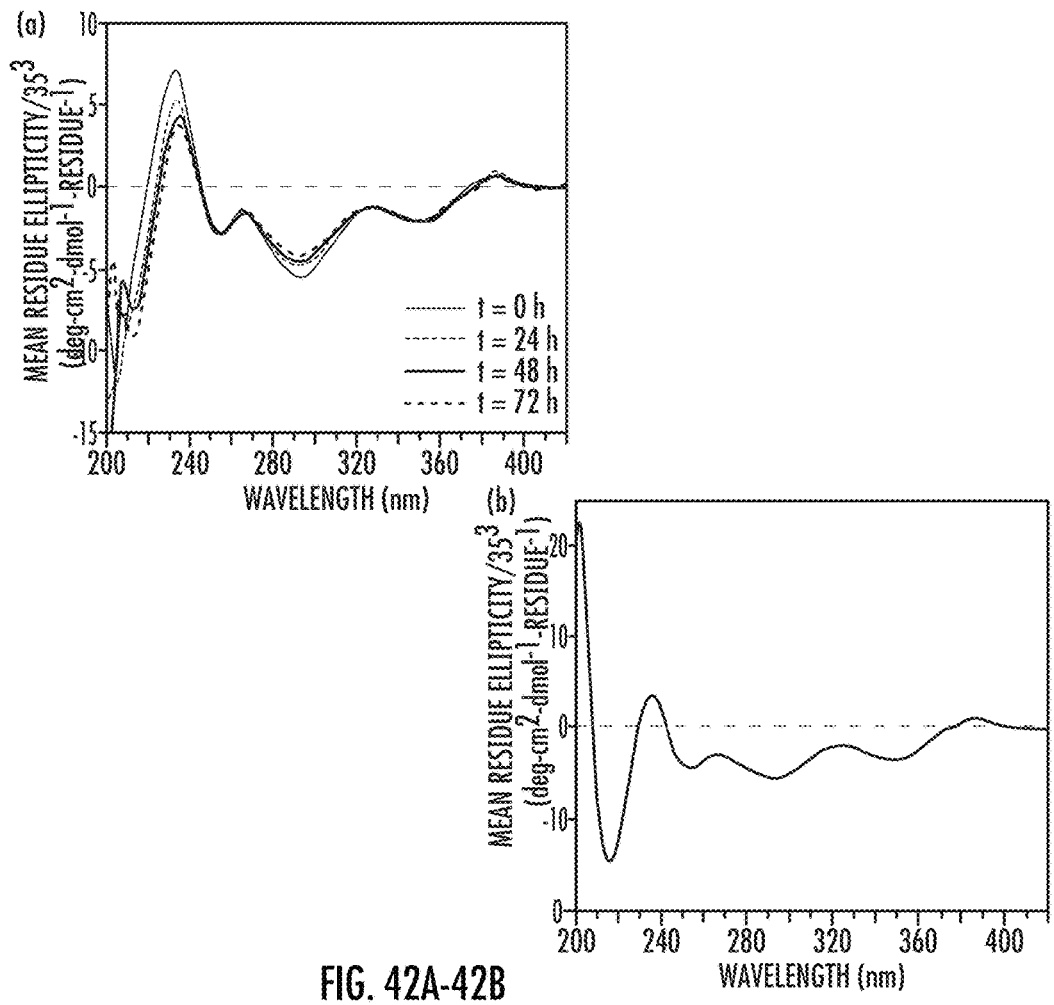
FIGS. 42A-42B shows the effect of dilution into PBS on the self-assembly of CPT-PXL-Sup35. (a) Time course study of a 100 µM sample in PBS prepared from a 1 mM solution in water that had been aged for 2 hours, showing the slow evolution of the β-sheet signal. (b) The CD spectra of a 100 µM sample in PBS prepared from a 1 mM solution in water that had been aged for 8 days, indicating that dilution into PBS does not disrupt the matured nanostructure.

Further evidence for the evolution of the nanostructure from small filaments to twisted two-filament fibrils is provided by studying the effect of high salt concentration on the morphology. Dilution of the 1 mM stock solution of CPT-PXL-Sup35 that had been aged for 2 hours to 100 µM in Dulbecco's phosphate-buffered saline (1×DPBS) was seen to effectively retard the structural evolution, giving only the small filament morphology (FIG. 41 a). Very little shift toward the twisted nanofilament structure was observed over the course of several days, with TEM analysis indicating only the smaller nanostructure with occasional examples of the entwined morphology (FIG. 41 b). CD analysis confirms that there is a slow shift toward the β-sheet structure, though it does not reach the extent of the sample aged in water even after 3 days (FIG. 42 a). This slower rate of structural evolution may be due to increased shielding/crosslinking of the protonated lysine residues by the multivalent phosphate anions. Reorganization of the internal structure requires that the assembly be dynamic in nature, the extent of which would be greater in the absence of the phosphate ions. By providing a screening effect, the phosphate anions significantly reduce the rate at which reorganization can occur. In contrast, dilution into 1×DPBS of a 1 mM sample (prepared in water) that had been allowed to age for 8 days exhibited the same twisted fibril morphology observed in pure water (FIG. 41 c) and possessed a CD spectrum consistent with that in pure water (FIG. 42 b). This indicates that dilution into DPBS does not disrupt the nanostructures already present in solution and that the morphologies observed are true representations of the assemblies present in the stock solution. An interesting point to note is that interfibril bundling is not observed despite the increased charge shielding afforded by the phosphate ions, with the fibrils being observed only as single elements. This suggests that their twisted nature does indeed reduce the likelihood of further lateral associations.

Figures 43A, 43B:
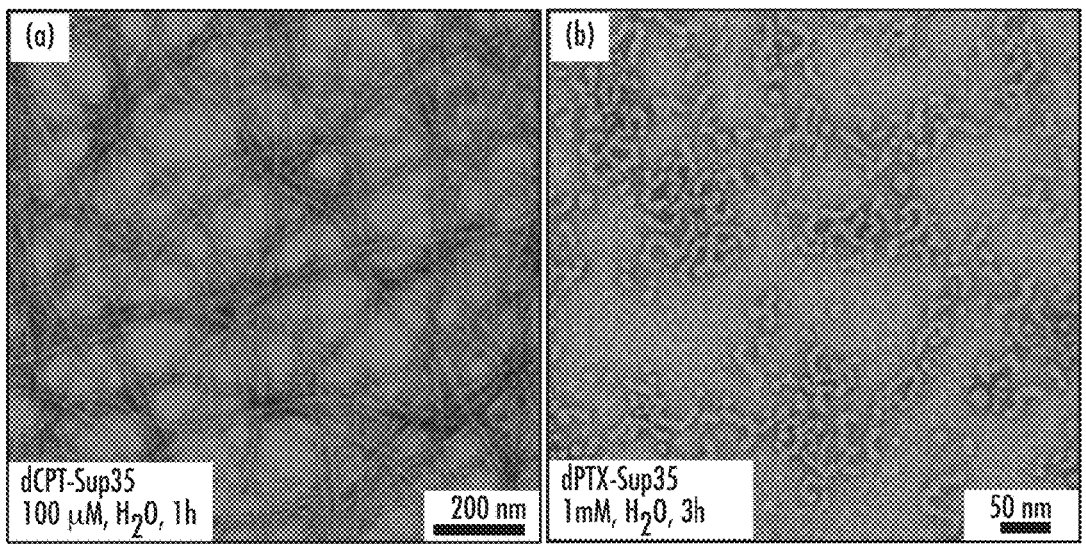
FIGS. 43A-43B depicts the TEM analysis of the self-assembled nanostructures of dCPT-buSS-Sup35 (100 µM in $H_2O$) (a) and dPXL-Sup35 (1 mM in $H_2O$) (b).

The observations from this self-assembly study clearly demonstrate the effect that the PXL molecule can have when incorporated into a drug amphiphile. In its absence, the planar CPT can easily adopt a filamentous morphology (FIG. 43 a), but the replacement of one CPT by the bulkier PXL results in a slower assembly process that ultimately gives a twisted fibrillar nanostructure. Replacement of both CPTs with PXL on the other hand leads to the formation of only small micellar structures (FIG. 43 b).

Figure 44:
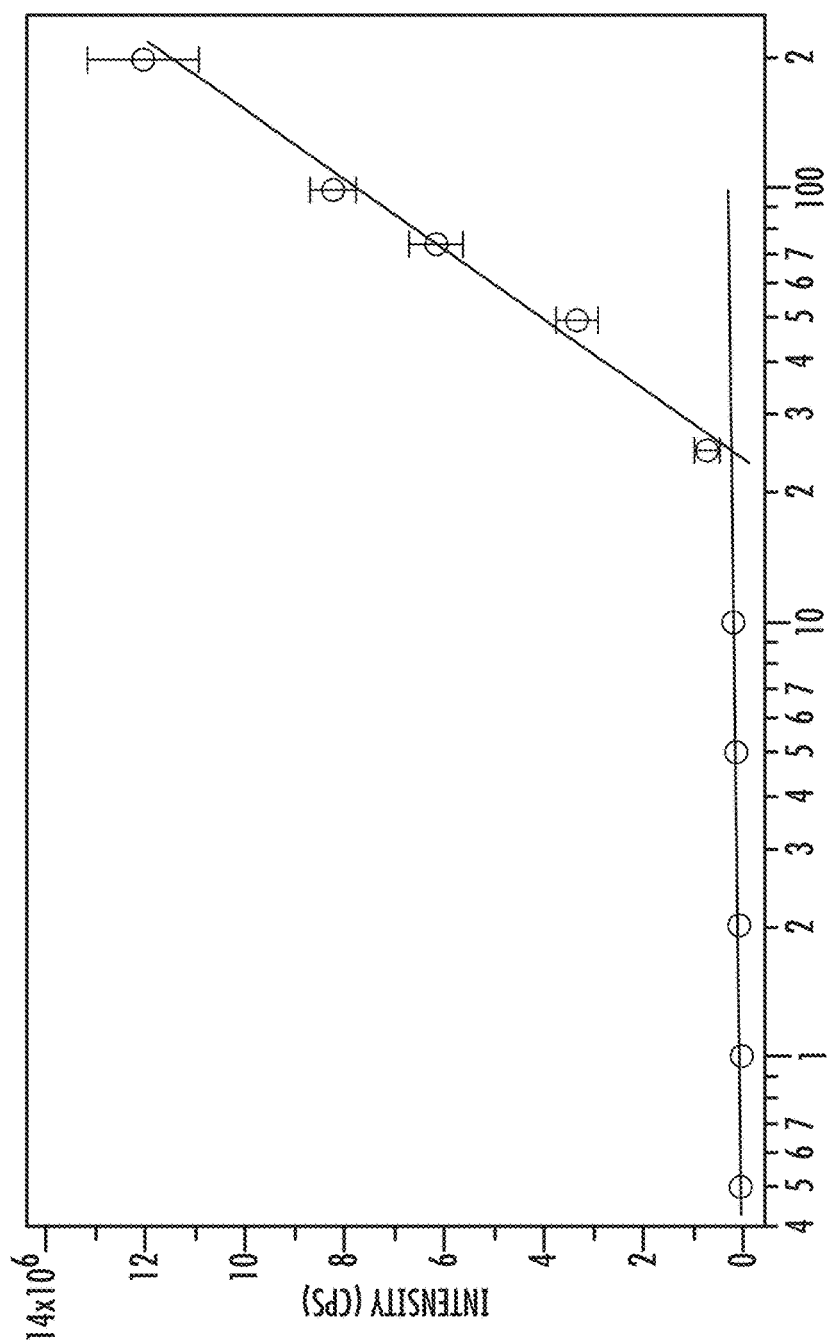
FIG. 44 depicts the Critical aggregation concentration (CAC) determination of CPT-PXL-Sup35 using a Nile red fluorescence method. Data are given as mean±s.d. (n=2).

Nanostructure Stability. To gain more information on the stability of these nanostructures, a critical aggregation constant (CAC) study was performed based on encapsulation of the solvatochromic fluorophore, Nile Red. The emission spectrum of this dye differs significantly when placed in hydrophobic or hydrophilic environments and thus can be used as a probe for assembly processes. Accordingly, various concentrations of CPT-PXL-Sup35 were incubated overnight with 1 µM Nile Red before recording the emission spectra (exciting at 550 nm). Plotting the 640 nm emission data against the conjugate concentration gave a CAC value between 20-30 µM for CPT-PXL-Sup35 (FIG. 44). This value fits into the CMC range reported by the Tirrell group for peptide amphiphile systems (Biochemistry 2009, 48, 3304-3314). A similar study for dCPT-Sup35, however, failed to give a satisfactory response as little increased fluorescence was observed, even at concentrations known to form significant nanostructures—likely due to poor penetration of the dye into the assembly that is expected to have a high degree of internal order arising from the π-π stacking of the CPT units. CD analysis of the two conjugates at 5 µM, recorded immediately after dilution of a 100 µM solution, revealed that disassembly of the nanostructures occurs at this concentration, with little or no β-sheet structure present. It should be noted that the Tau peptide analogue of dCPT- Sup35 in our previous work did not show such behavior, exhibiting the typical β-sheet signal even when diluted below 1 μM. This highlights the importance of the peptide sequence in the overall structural stability of drug amphiphiles. This difference in CAC values might due to the fact that the Sup35 peptide GNNQQNY (SEQ ID NO: 8) contains more polar amino acids than the Tau peptide VQIVYK (SEQ ID NO: 9), potentially affecting their hydrogen bonding capacity between themselves and with water.

Figures 45A, 45B:
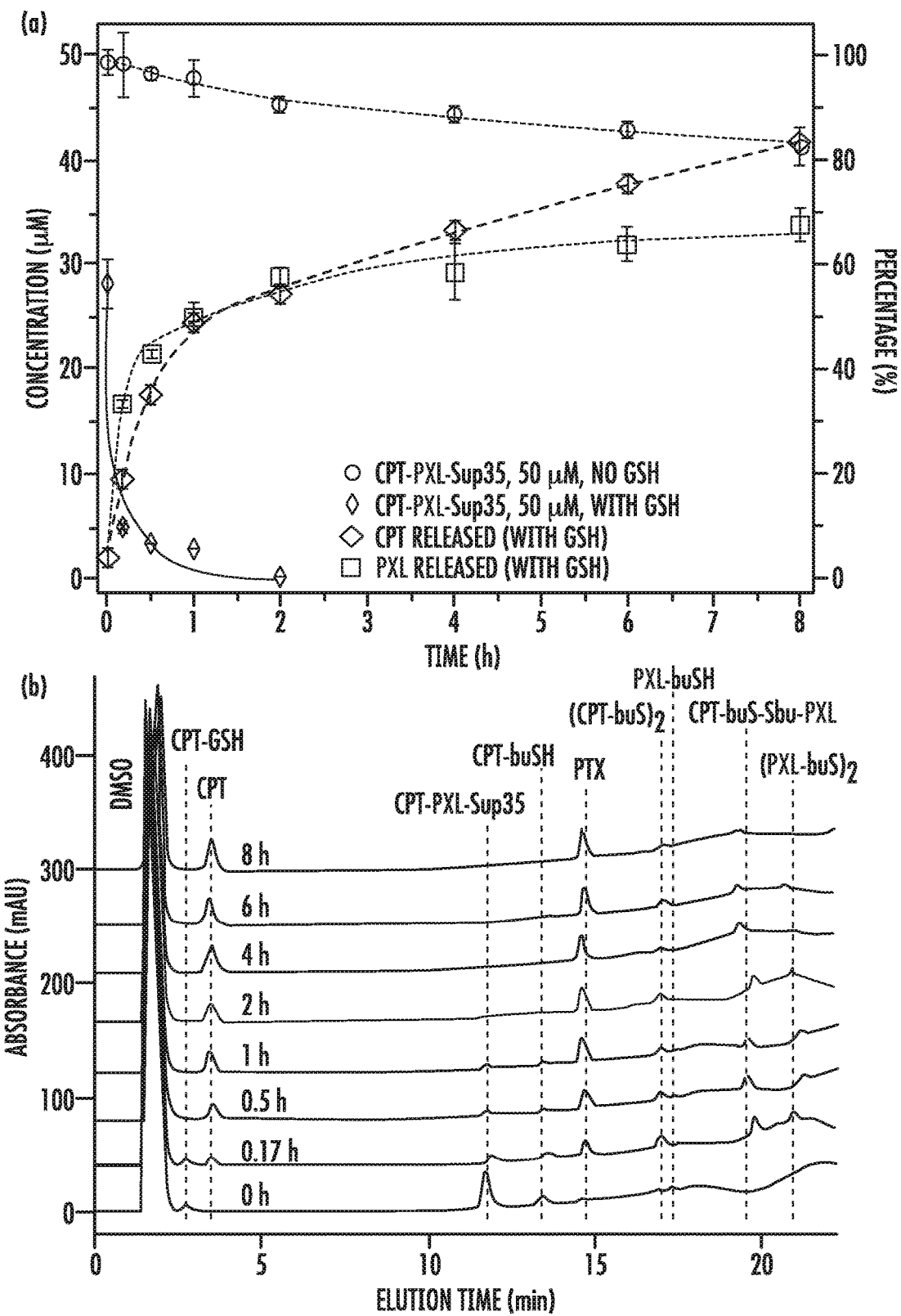
FIGS. 45A-45B depicts the Drug release study of 50 µM CPT-PXL-Sup35. (45 a) Release of CPT and PXL and degradation of CPT-PXL-Sup35 in the presence or absence of 10 mM GSH. (45 b) HPLC chromatograms showing the GSH-induced release of CPT, PXL and other intermediates from CPT-PXL-Sup35. All studies were carried out in 10 mM sodium phosphate solution with or without 10 mM GSH at 37° C. Data are given as mean±s.d. (n=3). Fitted curves are for illustrative purposes only.

Drug Release. In order to evaluate the ability of CPT-PXL-Sup35 to release its therapeutic cargo, we incubated a 50 μM solution of this dual DA at 37° C. in the presence or absence of the cancer-relevant reducing agent, glutathione (GSH) (FIG. 45 a). Aliquots were taken at various time points, quenching the reaction by the addition of 1 M HCl and flash freezing in liquid nitrogen. These samples were then analyzed by HPLC to determine the concentration of the important reaction components at each time point (CPT-PXL-Sup35, CPT and PXL). The conjugate was observed to degrade rapidly in the presence of GSH, being completely consumed within 2 hours, whereas >80% remained after 8 hours incubation in its absence. It can be seen that, initially at least, PXL is released almost twice as fast as CPT in the presence of GSH, perhaps due to the PXL-ester bond being more labile than the CPT-ester bond—hydrolysis of a 2° alcohol ester (PXL) is expected to be faster than that of a 3° alcohol ester (CPT) due to steric considerations of the tetrahedral intermediate formed. The increase in the free drug concentration continues beyond the 2 hour time that it takes to completely degrade the conjugate as the linker-modified form of the drugs, CPT-buSH and PXL-buSH, are released first, before undergoing further hydrolysis to give the free drugs. Homo- and hetero-disulfide products, such as $(CPT-buS)_2$, $(PXL-buS)_2$, and CPT-buS-Sbu-PXL, can also be observed before they too undergo reduction and/or hydrolysis (FIG. 45 b). Formation of these homo- and hetero-disulfide degradation products are likely a result of the supramolecular nature of the DA nanostructures, which leads to a high local concentration of released thiol products.

Figures 46A, 46B:
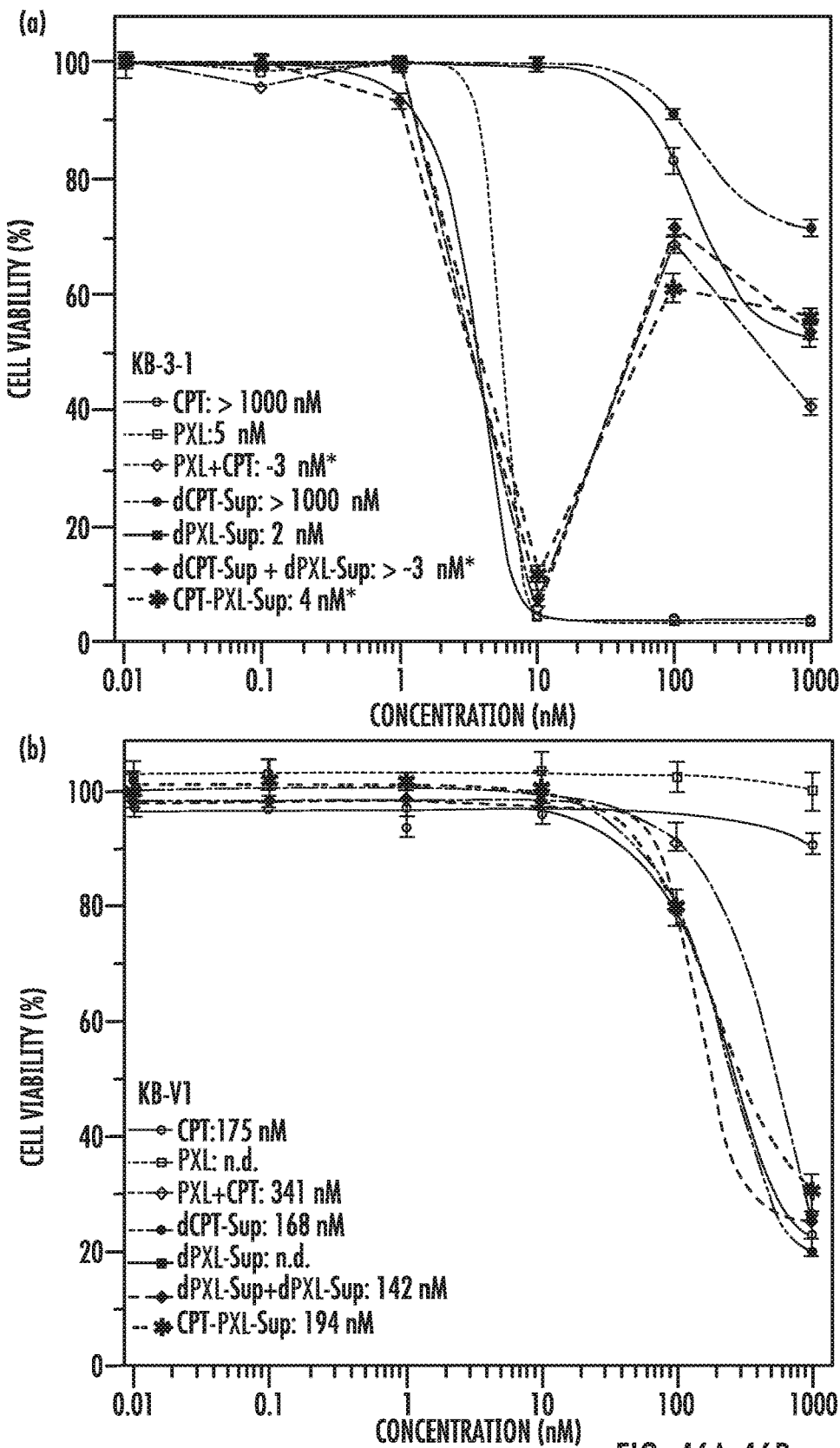
FIGS. 46A-46C depicts the cytoxicity study of the synthesized dual drug amphiphiles against PXL-sensitive KB3-1 cervical cancer cells (46 a), PXL-resistant KB-V1 cervical cancer cells (46 b) and a co-culture of KB-3-1 and KB-V1 cervical cancer cells (46 c). Both cell lines are sensitive to CPT. Cell viability was determined by SRB assay after 48 hours incubation with the appropriate drug-containing media. Calculated IC50 values are given in the figure legends, * indicates the IC50 value prior to any observed antagonism. Data are given as mean±s.d. (n=3).
Figure 46C:
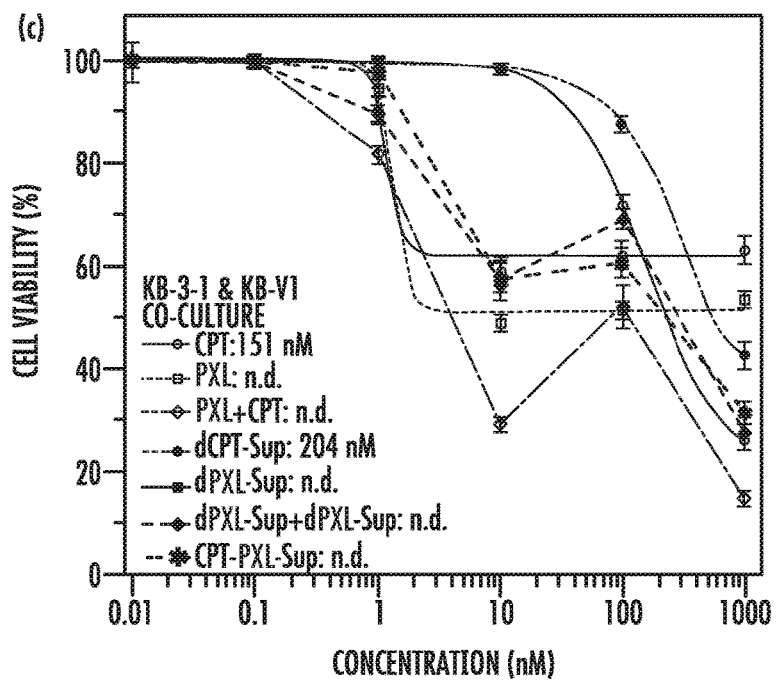

Cytotoxicity Study. The activity of the synthesized conjugates to prohibit proliferative ability was assessed through the determination of a dose-response relationship against PXL-sensitive and -resistant cervical cancer cell lines—KB-3-1 and KB-V1, respectively. Both cell lines were individually incubated for 48 hours with the conjugates alone or in combination, either individually to determine their sensitivity to the conjugates (FIGS. 46 a-b) and also as a co-culture to mimic a heterogeneous tumor (FIG. 46 c). As expected, the PXL-sensitive KB-3-1 cells (FIG. 46 a) display nanomolar sensitivity to the PXL-containing conjugates, dPXL-Sup35 (alone or in combination with dCPT-Sup35) and CPT-PXL-Sup35 and moderate sensitivity towards dCPT-Sup35, consistent with the respective activities of free PXL and CPT. At higher concentrations, the experiments that combined CPT and PXL, either as free drugs or drug amphiphiles, all showed a reduction in the anti-proliferative activity to levels similar to free CPT. This antagonistic behavior has been previously observed, and is suspected to arise from an up-regulation of anti-apoptosis genes on co-treatment with CPT that would inhibit the mechanism by which PXL exerts its cytotoxicity. The PXL-resistant KB-V1 cells (FIG. 46 b) show moderate sensitivity toward all the CPT-containing drug conjugates, with little difference compared to free CPT, whereas PXL and dPXLSup35 both show no activity.

Against a co-culture of KB-3-1 and KB-V1 cervical cancer cells, which serves to better mimic a heterogeneous tumor that consists of more than one phenotype, a similar trend in behavior is observed (FIG. 46 c). Cells treated with PXL-species only (free PXL or dPXL-Sup35) show no greater than 50% loss in viability after 48 hours, as only the PXL-sensitive KB-3-1 cells will be affected. Those treated with CPT-species only (free CPT or dCPT-Sup35) display moderate activity, similar to that observed for each individual cell line. Incubation with the homo-dual DA, CPT-PXL-Sup35, or a combination of the two hetero-dual DAs, dCPT-Sup35 and dPXL-Sup35, appears to effectively kill the KB-3-1 cells at lower concentrations, with only the KB-V1 cells likely to survive. The antagonistic behavior is again observed at higher concentrations and results in a comparable effect to free CPT as before. Surprisingly, the combination of free CPT and PXL exhibited a greater than expected anti-proliferative effect, with only 30% of cells remaining when treated with a 10 nM concentration of each drug. This implies that around 20% of the PXL-resistant KB-V1 cells are also affected despite having little sensitivity to CPT at this concentration, indicating that the observed cytotoxicity is due to PXL. While the antagonistic effect is still observed at higher concentrations, the overall cytotoxicity remains greater than CPT alone. Given that this effect is not seen for the KB-V1 mono-culture, it suggests that the use of CPT can perhaps, to some degree, sensitize PXL-resistant cells to PXL when co-cultured with sensitive cells.

We have demonstrated that the incorporation of two structurally distinct anticancer drug molecules into a single amphiphilic entity is a successful strategy for the creation of well-defined nanostructures. Combining CPT and PXL into a single hetero-dual drug amphiphile was found to give nanostructures that possess a two-filament fibril morphology in which two narrower filaments entwine about one another. These results illustrate that the conjugation of two drugs with differing packing preferences onto one conjugate can be accomplished without compromising the self-assembly or chemotherapeutic properties. This opens up the ability of simultaneous delivery of two drugs to the same location at the same time with the potential for a great degree of control.

Methods for Example 5

Peptide synthesis (Ac-Cys)$_2$KGN$_2$Q$_2$NYK$_2$-NH$_2$ (dCys-Sup35) (SEQ ID NO: 10) was synthesized using a combination of automated (Focus XC automated peptide synthesizer, AAPPTEC, Louisville, Ky., USA) and manual solid phase synthesis techniques, employing standard Fmoc chemistry protocols. Fmoc deprotections were performed using 20% 4-methylpiperidine in DMF and couplings were carried out using amino acid/O-(benzotriazol-1-yl)-N,N,N', N'-tetramethyluronium hexafluorophosphate (HBTU)/DIEA (4:3.98:6 relative to the resin) in DMF (with 2 minute activation time). Acetylation was carried out manually using 20% acetic anhydride in DMF after N-terminal Fmoc deprotection. The branching lysine and terminal cysteines were introduced manually using Fmoc-Lys(Fmoc)-OH and 0-(7-azabenzotriazol-1-yl)-N,N,N',N'-tetramethyluronium hexafluorophosphate (HATU).

Dual Drug Amphiphile Synthesis. dCys-Sup35 (21 mg, 14 μmol) was dissolved in a solution of an N$_2$-purged DMSO containing a 1:1 mixture of CPT-buSS-Pyr (12 mg, 21 μmol) and PXL-buSS-Pyr (22.5 mg, 21 μmol) and allowed to react for 5 days. Analytical HPLC showed the reaction was virtually complete, giving the expected doubly reacted products—dCPTSup35, dPXL-Sup35 and CPT-PXL-Sup35. The reaction mixture was diluted to 10 mL with 0.1% TFA in acetonitrile/water (2:3) and purified by preparative RP-HPLC. The appropriate product fractions were combined and lyophilized. The powders obtained were then re-dissolved, calibrated and aliquotted into cryo-vials before re-lyophilization as described below.

Figure 47:
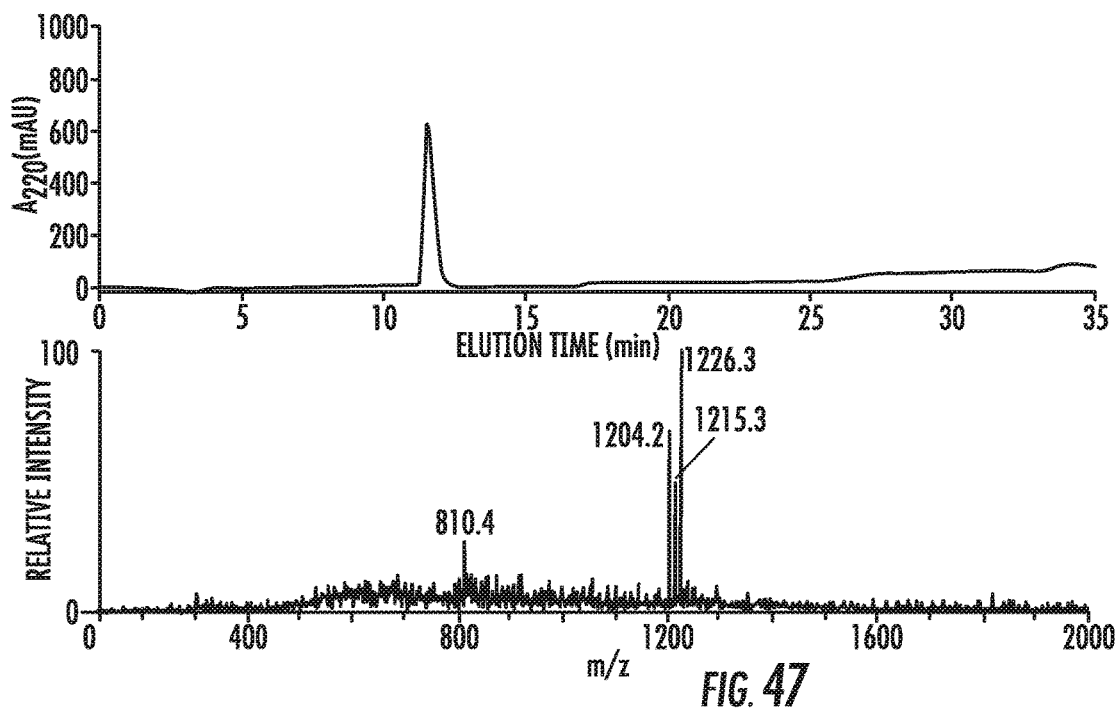
FIG. 47 depicts the HPLC (top) and ESI-MS (bottom) characterization of purified dCPT-Sup35.

The isolated dCPT-Sup35 was dissolved in 3 mL H2O. Calibration based on the CPT absorbance gave a conjugate concentration of 448 µM. Yield=3.2 mg, 10%. ESI-MS (%): 1226.3 (100) $[M+2Na]^{2+}$, 1204.2 (69) $[M+2H]^{2+}$, 1215.3 (49) $[M+H+Na]^{2+}$, 810.4 (26) $[M+2H+Na]^{3+}$ (FIG. 47).

Figure 48:
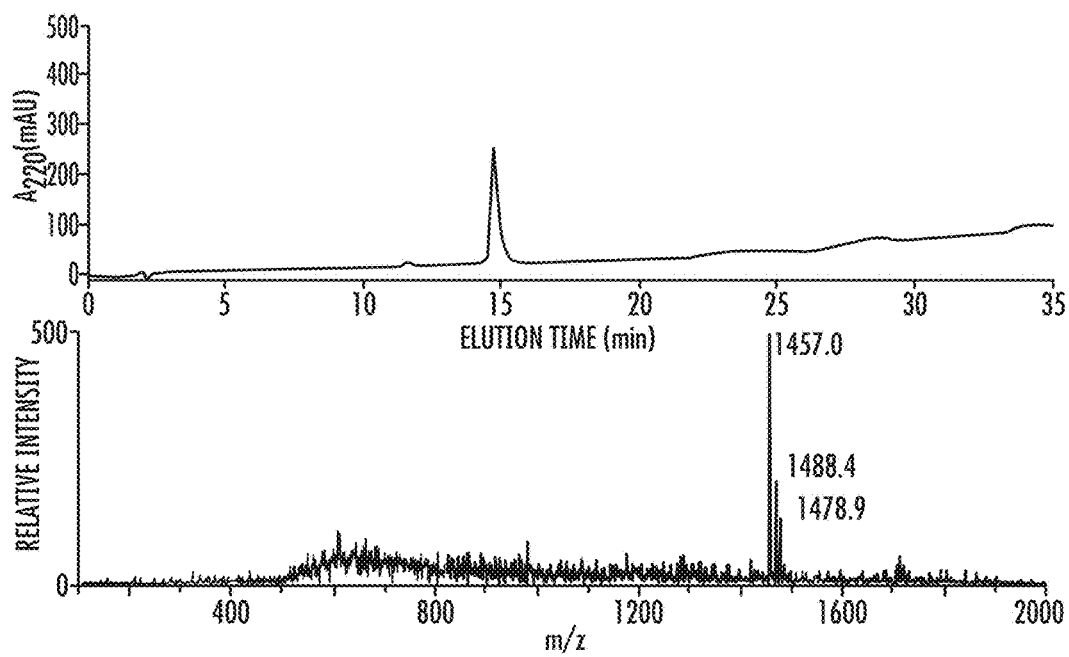
FIG. 48 depicts the HPLC (top) and ESI-MS (bottom) characterization of purified CPT-PXL-Sup35.

The isolated CPT-PXL-Sup35 was dissolved in 6 mL of 1:1 MeCN/H$_2$O. Calibration based on the CPT absorbance gave a conjugate concentration of 400 µM. Yield=7.0 mg, 17%. ESI-MS (%): 1457.0 (100) $[M+2H]^{2+}$, 1468.4 (41) $[M+H+Na]^{2+}$, 1478.9 (31) $[M+2Na]^{2+}$ (FIG. 48).

Figure 49:
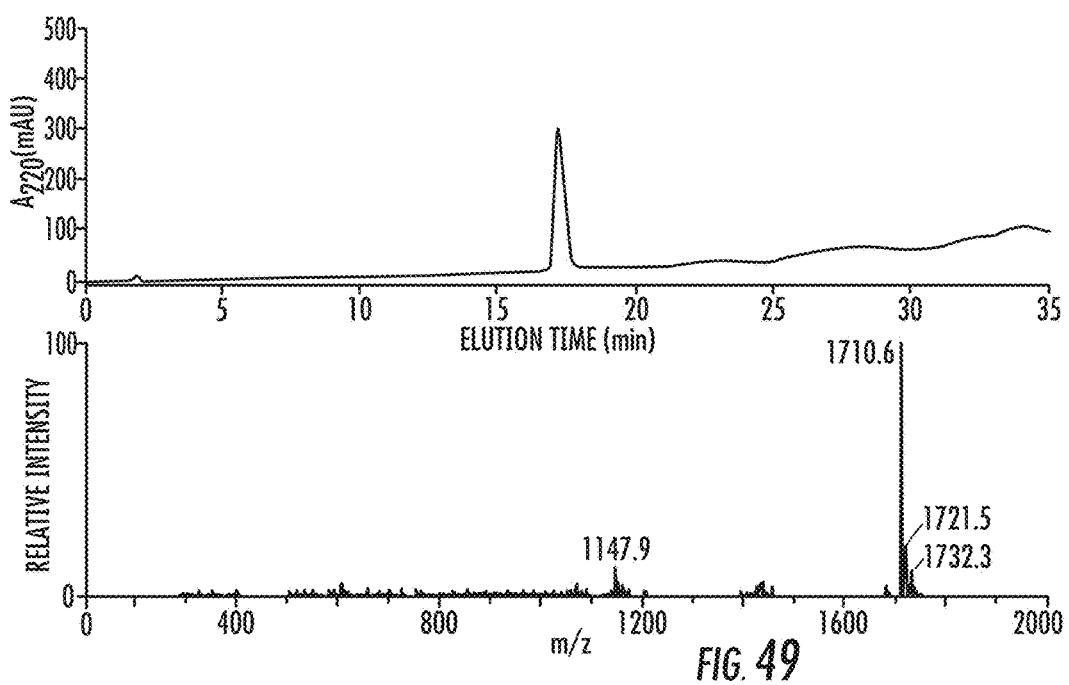
FIG. 49 depicts the HPLC (top) and ESI-MS (bottom) characterization of purified dPXL-Sup35

The isolated dPXL-Sup35 was dissolved in 3 mL of 1:2 MeCN/H$_2$O. Calibration based on the PXL absorbance gave a conjugate concentration of 204 µM. Yield=2.1 mg, 4%. ESI-MS (%): 1710.6 (100) $[M+2H]^{2+}$, 1721.5 (8) $[M+H+Na]^{2+}$, 1147.9 (6) $[M+2H+Na]^{3+}$, 1732.3 (2) $[M+2Na]^{2+}$ (FIG. 49).

Transmission Electron Microscopy. Samples were prepared by depositing 7 µL of the appropriate solution onto a carbon-coated copper grid (Electron Microscopy Services, Hatfield, Pa., USA), wicking away the excess solution with a small piece of filter paper. Next, 7 µL of a 2 wt % aqueous uranyl acetate solution was deposited and the excess solution was carefully removed as above to leave a very thin layer. The sample grid was then allowed to dry at room temperature prior to imaging. Bright-field TEM imaging was performed on a FEI Tecnai 12 TWIN Transmission Electron Microscope operated at an acceleration voltage of 100 kV. All TEM images were recorded by a SIS Megaview III wideangle CCD camera.

Cryogenic Transmission Electron Microscopy. 6 µL of sample solution was placed on a holey carbon film supported on a TEM copper grid (Electron Microscopy Services, Hatfield, Pa., USA). All the TEM grids used for cryo-TEM imaging were treated with plasma air to render the lacey carbon film hydrophilic. A thin film of the sample solution was produced using the Vitrobot with a controlled humidity chamber (FEI). After loading of the sample solution, the lacey carbon grid was blotted using preset parameters and plunged instantly into a liquid ethane reservoir pre-cooled by liquid nitrogen. The vitrified samples were then transferred to a cryo-holder and cryo-transfer stage that was cooled by liquid nitrogen. Imaging was performed using a FEI Tecnai 12 TWIN Transmission Electron Microscope (100 kV) and images were recorded by a 16 bit 2K×2K FEI Eagle bottom mount camera. To prevent sublimation of vitreous water, the cryo-holder temperature was maintained below −170° C. during the imaging process.

Circular Dichroism. CD spectra were recorded on a Jasco J-710 spectropolarimeter (JASCO, Easton, Md., USA) using a 1 mm path length quartz UV-Vis absorption cell (Thermo Fisher Scientific, Pittsburgh, Pa., USA). Background spectra of the solvents were acquired and subtracted from the sample spectra. Collected data was normalized with respect to sample concentration and β-sheet forming residues.

Drug Release Protocol. Briefly, a 100 µM solution CPT-PXLSup35 in deionized water was freshly prepared before the experiment and diluted to 50 µM with sodium phosphate buffer (pH 7.4, 20 mM) with or without GSH (20 mM). The solutions were incubated at 37° C. and sampled at 0, 0.17, 0.5, 1, 2, 4, 6, and 8 hours. The samples were acidified by the addition of 0.2 µL of 2 M HCl, flash frozen with liquid nitrogen and stored at −30° C. until analysis by RP-HPLC was performed. The degradation of CPT-PXL-Sup35 was monitored by RP-HPLC using the following conditions: 237 nm detection wavelength; 1 ml/min flow rate; mobile phase was 0.1% aqueous TFA (A) and acetonitrile containing 0.1% TFA; gradient is given in Table 1.

TABLE 1

HPLC gradient used for drug release study.

| Time (min) | Mobile Phase A (%) | Mobile Phase B (%) |
|---|---|---|
| 0 | 65 | 35 |
| 5 | 65 | 35 |
| 18 | 13 | 87 |
| 21 | 13 | 87 |
| 22 | 65 | 35 |
| 25 | 65 | 35 |

The concentrations of CPT-PXL-Sup35, CPT and PXL were determined by measuring the area of the respective peaks in the HPLC chromatogram and comparing against a calibration curve for each species.

Cell Culture. KB-3-1 and KB-V1 ovarian cancer cells were cultured in DMEM (Invitrogen) containing 10% fetal bovine serum (FBS, Invitrogen) and 1% of antibiotics (Invitrogen), and 1 µg/mL vinblastine was added for KB-V1 to maintain its multidrug resistance. The two cell types were incubated at 37° C. in an Oasis humidified incubator with a 5% CO$_2$ atmosphere (Caron, Marietta, Ohio).

Cytotoxicity Protocol. KB-3-1, KB-V1 or their co-culture (1:1) were seeded onto 96-well plate (5×10$^3$ cells/well) and allowed to attach overnight. PXL-CPT-Sup35 was diluted with fresh medium and incubated with cells immediately to achieve final conjugate concentrations of 0.01, 0.1, 1, 10, 100 and 1000 nM. Medium containing the same concentration of PXL or/and CPT in the form of free drugs or conjugates (dCPT-Sup35 or dPXL-Sup35) were also used to incubate the cells, with non-treated cells (solvent only) as the control group. After 48 hours incubation, the cell viability was determined using the SRB method according to the manufacturer's protocol (TOX-6, Sigma, St. Louis, Mo.).

Example 6

Preparation of a αv-β3 Integrin-Targeted DA, mCPT-buSS-Tau-RGD

An αv-β3 integrin-targeted DA, mCPT-buSS-Tau-RGD, was synthesized by reaction of the activated-disulfide, CPT-buSS-Pyr, with the cysteine-functionalized peptide, CGVQIVYKKGRDG (SEQ ID NO: 12) in DMSO. The peptide was synthesized using standard solid-phase Fmoc peptide synthesis techniques and purified by RP-HPLC prior to conjugation with the activated disulfide. The DA was isolated by RP-HPLC.

A folate-targeting DA was synthesized by reaction of the activated-disulfide, PXL-buSS-Pyr, with the cysteine-functionalized peptide, CGNNQQNYKKGK(folate) (SEQ ID NO: 14) in DMSO. The folate-functionalized peptide was synthesized by 1) synthesis of the protected peptide using solid-phase Fmoc synthesis techniques, employing an Mtt-protected lysine at the C-terminal to allow selective functionalization of this residue; 2) removal of the Mtt protecting group using a 4% TFA solution in DCM with 5% triisopropylsilane; 3) conjugation of a suitably-protected folate was performed using HBTU and DIEA as coupling reagents, to give the folate-peptide; 4) cleavage and deprotection was performed using standard protocols, followed by RP-HPLC purification.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition comprising a conjugate of formula: D-L-PEP;

wherein D is 1 or more hydrophobic drug molecules;
L is 1 or more biodegradable linkers; and
PEP is a hydrophilic peptide selected from the group consisting of GVQIVYKK (SEQ ID NO: 1), CGNNQQNYKK (SEQ ID NO: 5), CGVQIVYKK (SEQ ID NO: 6), GNNQQNYKK (SEQ ID NO: 7), and CCKGNNQQNYKK (SEQ ID NO: 10); and wherein the conjugate is selected from the group consisting of: camptothecin-(4-(pyridin-2-yldisulfanyl)butanoate)-GVQIVYKK (mCPT-buSS-Tau); (camptothecin)$_2$-(4-(pyridin-2-yldisulfanyl)butanoate)-GVQIVYKK (dCPT-buSS-Tau); (camptothecin)$_4$-(4-(pyridin-2-yldisulfanyl)butanoate)-GVQIVYKK (qCPT-buSS-Tau); (camptothecin)$_4$-(4-(pyridin-2-yldisulfanyl)butanoate)-CGNNQQNYKK (qCPT-buSS-Sup35); camptothecin-disulfanylcarbonate-CGVQIVYKK (mCPT-etcSS-Tau); paclitaxel-(4-(pyridin-2-yldisulfanyl)butanoate)-GVQIVYKK (PXL-buSS-Tau); camptothecin-Cys-GNNQQNYKK (CPT-Cys-Sup35); paclitaxel-Cys-GNNQQNYKK (PXL-Cys-Sup35); (camptothecin)$_2$-CCKGNNQQNYKK (dCPT-Sup35); (paclitaxel)$_2$-CCKGNNQQNYKK (dPXL-Sup35); and camptothecin-paclitaxel-CCKGNNQQNYKK (CPT-PXL-Sup35).

2. The composition of claim 1, further comprising a pharmaceutically acceptable carrier.

3. The composition of claim 2, further comprising at least one additional biologically active agent.

4. A composition comprising a conjugate of formula: D-L-PEP-T;

wherein D is 1 or more hydrophobic drug molecules;
L is 1 or more biodegradable linkers;
PEP is a hydrophilic peptide selected from the group consisting of GVQIVYKK (SEQ ID NO: 1), CGNNQQNYKK (SEQ ID NO: 5), CGVQIVYKK (SEQ ID NO: 6), GNNQQNYKK (SEQ ID NO: 7), and CCKGNNQQNYKK (SEQ ID NO: 10); and wherein the D-L-PEP in the conjugate is selected from the group consisting of: camptothecin-(4-(pyridin-2-yldisulfanyl)butanoate)-GVQIVYKK (mCPT-buSS-Tau); (camptothecin)$_2$-(4-(pyridin-2-yldisulfanyl)butanoate)-

GVQIVYKK (dCPT-buSS-Tau); (camptothecin)$_4$-(4-(pyridin-2-yldisulfanyl)butanoate)-GVQIVYKK (qCPT-buSS-Tau); (camptothecin)$_4$-(4-(pyridin-2-yldisulfanyl)butanoate)-CGNNQQNYKK (qCPT-buSS-Sup35); camptothecin-disulfanylcarbonate-CGVQIVYKK (mCPT-etcSS-Tau); paclitaxel-(4-(pyridin-2-yldisulfanyl)butanoate)-GVQIVYKK (PXL-buSS-Tau); camptothecin-Cys-GNNQQNYKK (CPT-Cys-Sup35); paclitaxel-Cys-GNNQQNYKK (PXL-Cys-Sup35); (camptothecin)$_2$-CCKGNNQQNYKK (dCPT-Sup35); (paclitaxel)$_2$-CCKGNNQQNYKK (dPXL-Sup35); and camptothecin-paclitaxel-CCKGNNQQNYKK (CPT-PXL-Sup35); and T is a targeting ligand selected from the group consisting of RGD, RGDS (SEQ ID NO: 13), folate and methotrexate.

5. The composition of claim 4, further comprising a pharmaceutically acceptable carrier.

6. The composition of claim 4, further comprising at least one additional biologically active agent.

\* \* \* \* \*

SEQUENCE LISTING

```
<160> NUMBER OF SEQ ID NOS: 14

<210> SEQ ID NO 1
<211> LENGTH: 8
<212> TYPE: PRT
<213> ORGANISM: artificial sequence
<220> FEATURE:
<223> OTHER INFORMATION: Tau protein fragment

<400> SEQUENCE: 1

Gly Val Gln Ile Val Tyr Lys Lys
1               5

<210> SEQ ID NO 2
<211> LENGTH: 6
<212> TYPE: PRT
<213> ORGANISM: artificial sequence
<220> FEATURE:
<223> OTHER INFORMATION: yeast Sup35 peptide fragment

<400> SEQUENCE: 2

Asn Asn Gln Gln Asn Tyr
1               5

<210> SEQ ID NO 3
<211> LENGTH: 13
<212> TYPE: PRT
<213> ORGANISM: artificial sequence
<220> FEATURE:
<223> OTHER INFORMATION: HIV Tat protein fragment

<400> SEQUENCE: 3

Gly Arg Lys Lys Arg Arg Gln Arg Arg Arg Pro Pro Gln
1               5                   10

<210> SEQ ID NO 4
<211> LENGTH: 14
<212> TYPE: PRT
<213> ORGANISM: artificial sequence
<220> FEATURE:
<223> OTHER INFORMATION: alpha helical peptide

<400> SEQUENCE: 4

Leu Leu Lys Lys Leu Leu Lys Leu Leu Lys Lys Leu Leu Lys
```

```
1               5                   10
```

<210> SEQ ID NO 5
<211> LENGTH: 10
<212> TYPE: PRT
<213> ORGANISM: artificial sequence
<220> FEATURE:
<223> OTHER INFORMATION: Sup35 yeast prion fragment

<400> SEQUENCE: 5

```
Cys Gly Asn Asn Gln Gln Asn Tyr Lys Lys
1               5                   10
```

<210> SEQ ID NO 6
<211> LENGTH: 9
<212> TYPE: PRT
<213> ORGANISM: artificial sequence
<220> FEATURE:
<223> OTHER INFORMATION: Sup35 yeast prion fragment

<400> SEQUENCE: 6

```
Cys Gly Val Gln Ile Val Tyr Lys Lys
1               5
```

<210> SEQ ID NO 7
<211> LENGTH: 9
<212> TYPE: PRT
<213> ORGANISM: artificial sequence
<220> FEATURE:
<223> OTHER INFORMATION: Sup35 yeast prion fragment

<400> SEQUENCE: 7

```
Gly Asn Asn Gln Gln Asn Tyr Lys Lys
1               5
```

<210> SEQ ID NO 8
<211> LENGTH: 7
<212> TYPE: PRT
<213> ORGANISM: artificial sequence
<220> FEATURE:
<223> OTHER INFORMATION: Sup35 Yeast prion fragment

<400> SEQUENCE: 8

```
Gly Asn Asn Gln Gln Asn Tyr
1               5
```

<210> SEQ ID NO 9
<211> LENGTH: 6
<212> TYPE: PRT
<213> ORGANISM: artificial sequence
<220> FEATURE:
<223> OTHER INFORMATION: Tau protein fragment

<400> SEQUENCE: 9

```
Val Gln Ile Val Tyr Lys
1               5
```

<210> SEQ ID NO 10
<211> LENGTH: 12
<212> TYPE: PRT
<213> ORGANISM: artificial sequence
<220> FEATURE:
<223> OTHER INFORMATION: Sup35 yeast prion fragment

<400> SEQUENCE: 10

```
Cys Cys Lys Gly Asn Asn Gln Gln Asn Tyr Lys Lys
1               5                   10
```

```
<210> SEQ ID NO 11
<211> LENGTH: 10
<212> TYPE: PRT
<213> ORGANISM: artificial sequence
<220> FEATURE:
<223> OTHER INFORMATION: Tau protein derived sequence

<400> SEQUENCE: 11

Cys Gly Val Gln Ile Val Tyr Lys Lys Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: synthetic sequence

<400> SEQUENCE: 12

Cys Gly Val Gln Ile Val Tyr Lys Lys Gly Arg Asp Gly
1               5                   10

<210> SEQ ID NO 13
<211> LENGTH: 4
<212> TYPE: PRT
<213> ORGANISM: Artificial Sequence
<220> FEATURE:
<223> OTHER INFORMATION: synthetic sequence

<400> SEQUENCE: 13

Arg Gly Asp Ser
1

<210> SEQ ID NO 14
<211> LENGTH: 12
<212> TYPE: PRT
<213> ORGANISM: artificial sequence
<220> FEATURE:
<223> OTHER INFORMATION: Sup35 yeast prion fragment

<400> SEQUENCE: 14

Cys Gly Asn Asn Gln Gln Asn Tyr Lys Lys Gly Lys
1               5                   10
```